US008372964B2

(12) United States Patent
Ryu et al.

(10) Patent No.: US 8,372,964 B2
(45) Date of Patent: Feb. 12, 2013

(54) HIGHLY INFECTIOUS NUCLEIC ACID MOLECULES FROM PEPPER MOTTLE VIRUS AND PLANT VIRAL VECTOR DERIVED FROM THE SAME

(75) Inventors: Ki Hyun Ryu, Namyangju-si (KR); Mi Yeon Lee, Seoul (KR); Jin Sung Hong, Seoul (KR)

(73) Assignee: Seoul Women's University Industry—University Cooperation Foundation, Seoul (KR)

( * ) Notice: Subject to any disclaimer, the term of this patent is extended or adjusted under 35 U.S.C. 154(b) by 31 days.

(21) Appl. No.: 12/739,908

(22) PCT Filed: Sep. 26, 2008

(86) PCT No.: PCT/KR2008/005716

§ 371 (c)(1), (2), (4) Date: Apr. 26, 2010

(87) PCT Pub. No.: WO2009/082085

PCT Pub. Date: Jul. 2, 2009

(65) Prior Publication Data

US 2010/0251430 A1 Sep. 30, 2010

(30) Foreign Application Priority Data

Dec. 26, 2007 (KR) ........................ 10-2007-0137270

(51) Int. Cl.
*C12N 15/40* (2006.01)
*C12N 15/82* (2006.01)
*C12N 5/10* (2006.01)

(52) U.S. Cl. .................................... 536/23.72; 800/280

(58) Field of Classification Search .................. 800/280
See application file for complete search history.

(56) References Cited

FOREIGN PATENT DOCUMENTS

WO WO 9951749 A2 * 10/1999

OTHER PUBLICATIONS

Restrepo-Hartwig et al. The tobacco etch potyvius 6-kiladalton protein is membrane associated and involved in viral replication (1994) J. of Virology 68: 2388-2397.*

Pettite Kneller et al. Cap-independent translation of plant viral RNAs (2006) Virus Res. 119: 63-75.*

Bryan et al. Nucleotide sequence of the coat protein gene of a strain of clover yellow vein virus from New Zealand: conservation of a stem-loop structure in the 3' resion of potyviruses (1992) Arch. Virol. 124: 133-146.*

Yoon et al., (2003) GenEmbl Accession No. AB126033.1.*

Atreya et al. Amino acid substitution in the coat protein result in loss of insect transmissibility of a plant virus (1991) Proc. Nat. Acad. Sci. 88: 7887-7891.*

Idris et al., "Sinaloa Tomato Leaf Curl Geminivirus: Biological and Molecular Evidence for a New Subgroup III Virus," Phytopathology 88:648-657, 1998.

Rhie et al., "Complete Genome Sequence Supports Bell Pepper Mottle Virus as a Species of the Genus *Tobamovirus*," Arch. Virol. 152:1401-1407, 2007.

Shin et al., "The Potential Use of a Viral Coat Protein Gene as a Transgene Screening Marker and Multiple Virus Resistance of Pepper Plants Coexisting Coat Proteins of Cucumber Mosaic Virus and Tomato Mosaic Virus," Transgenic Res. 11:215-219, 2002.

Vance et al., "The Complete Nucleotide Sequence of Pepper Mottle Virus Genomic RNA: Comparison of the Encoded Polyprotein with Those of Other Sequenced Potyviruses," Virology 191:19-30, 1992.

International Search Report from International Application No. PCT/KR2008/005716, dated Jul. 22, 2009.

* cited by examiner

*Primary Examiner* — Anne Grunberg
*Assistant Examiner* — Steven Bernacki
(74) *Attorney, Agent, or Firm* — Clark & Elbing LLP

(57) ABSTRACT

The present invention relates to a plant-infectious nucleic acid molecule from Pepper mottle virus, and a viral vector, a transformed cell and a transgenic plant having it. The present invention first achieves the cloning of the infectious full-length pepper mottle virus cDNA from virus-infected pepper, which enables to perform the molecular biological studies to the infectivity of pepper mottle virus in pepper and tobacco and to provide a plant virus-based vector to highly express a useful foreign protein.

6 Claims, 25 Drawing Sheets

Fig. 1

```
RNA isolation from PepMoV-Vb infected N. benthamiana
                        |
              RT-PCR & cDNA cloning
                        |
               Sequencing analysis
                        |
          ┌─────I──────┴──────II─────┐
  in vitro; SP6 promoter        in vivo; 35S promoter
          |                             |
  1st cloning; pBSSK(-)II/PepMoV-Vb1N-term    pGEM T-easy sub-cloning
          |                             |
  2nd cloning; pBSSK(-)II/PepMoV-Vb1N+C-term   35S promoter fusion & sequential cloning
          |                             |
   SP6-PepMoV-Vb1 clone            35S-PepMoV-Vb1
          |                             |
   In vitro transcripts inoculation    Plasmid DNA direct inoculation
          └──────────────┬──────────────┘
           Screening of infectious full-length cDNA clone
```

Fig. 4
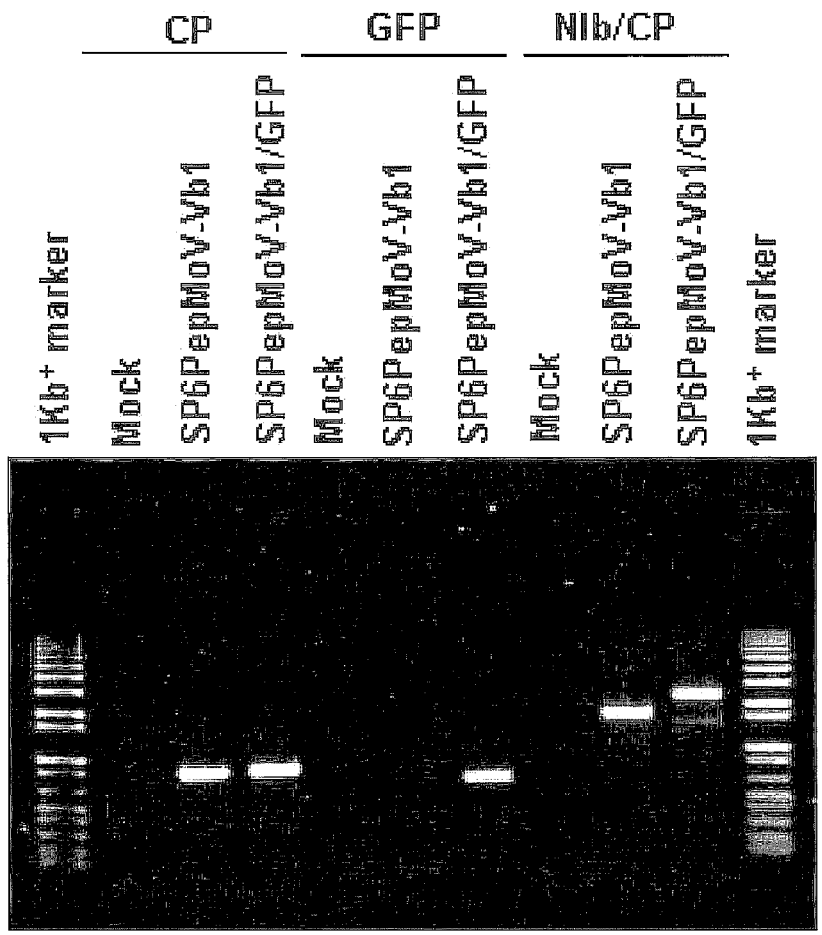
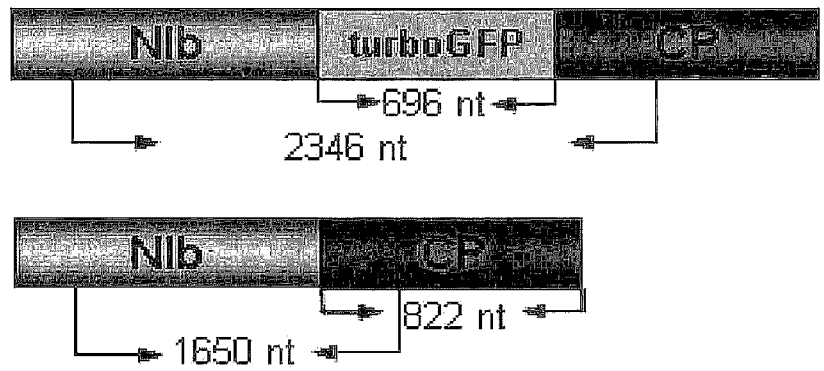

Fig. 5 pSP6PepMoV-Vb1/GFP     <u>GAC</u> <u>GCT</u> <u>GGA</u>
                                           D    A    G pSP6PepMoV-Vb1/GFP-NAT     <u>GAC</u> <u>GCT</u> G$\overset{*}{A}$A
                                             D    A    E SP6 → | P1 | HC-Pro | P3 | | 6K1 | CI | 6K2 | NIa-VPg | NIa-Pro | NIb | GFP | CP | ······ PolyA    DAG→DAE * 3'UTR

PepMoV-Vb1/GFP-NAT point mutation primer

1. NAT5'
   5' GAG CAG CTC AAG ATC AGA CAC ATT GGA CGC TGA AGA GGA GAA AAA G 3' (total 46mer)

2. NAT3'
   5' GTG GCT ACT TCT TTA TTT TTC TTT TTC TCC TCT TCA GCG TCC AAT GTG TC 3' (total 50mer)

Fig. 12
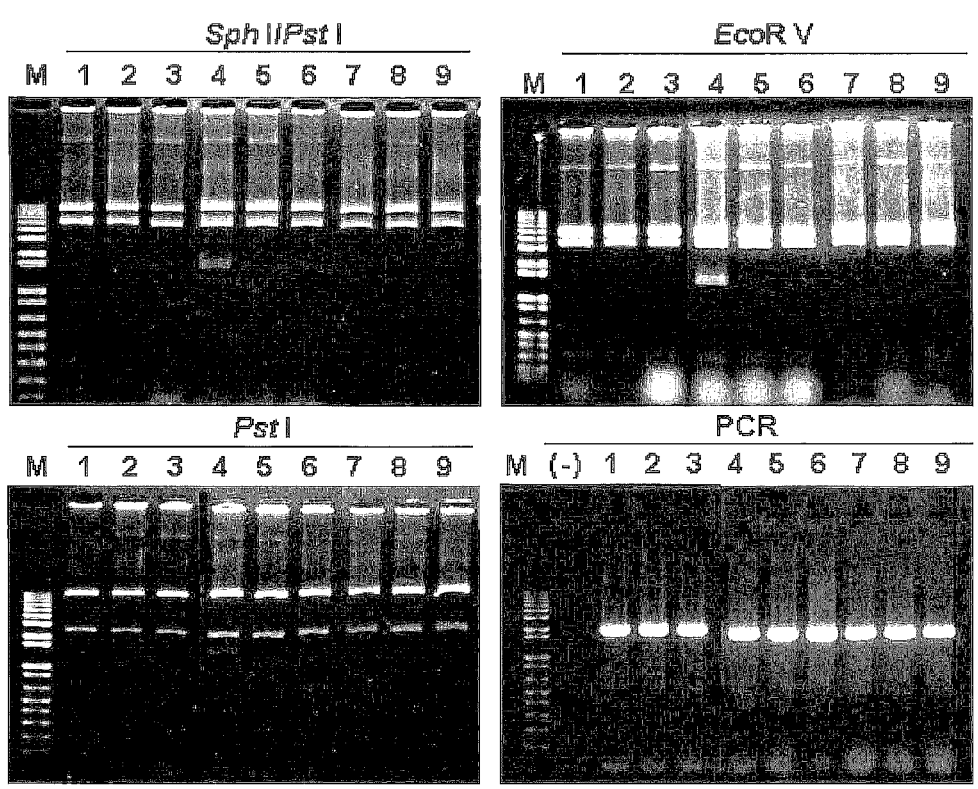
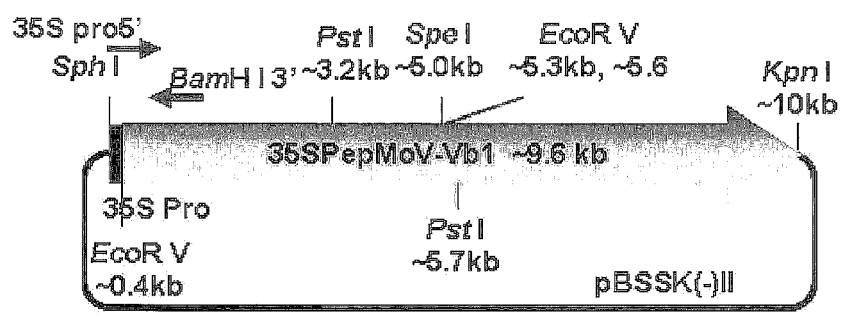

Fig. 20

Fig. 25
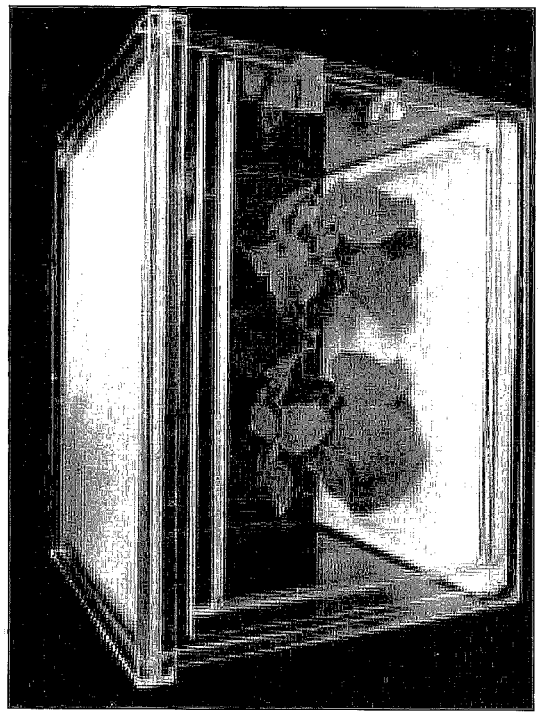
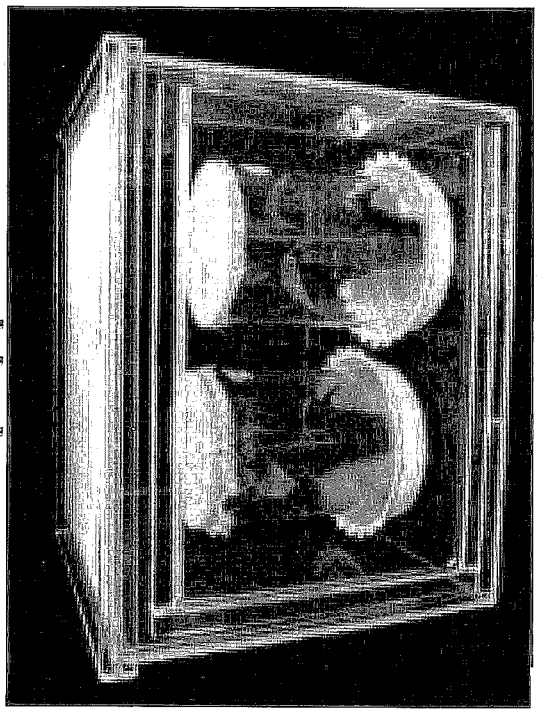

SEQUENCE LISTING

```
<160> NUMBER OF SEQ ID NOS: 44

<210> SEQ ID NO 1
<211> LENGTH: 9655
<212> TYPE: DNA
<213> ORGANISM: Pepper mottle virus

<400> SEQUENCE: 1
aaattaaaac ataacataca acataaacga aagcaatcaa attttcaagc aatttccttg      60
aactctttaa ttctcttcta caagttaagc attttgatta acactactgt cttaatttga     120
atattttaat cattttcagt ttcttctact agcactctac actagcaatg gcaattaacg     180
ttattcagtt tggttcattt gtgtgcaatc ttccaaagtt tcaatcatcg tgcacaacta     240
tgcactgccc aaagcagagc ataagcacca atgtagtgca cccaagtaac ccattcgctg     300
aactcgagga acgtctcgaa ccatacttgc aaaggaggat ggatgcaaca atacgcctaa     360 ctagaggcg gacgcttgtg tataaacaca tgagcgaagc taaacgcgcc aagaagctta     420
gaaagaagca gcgtgaggaa gaggaggtgc atttgttcat gaatgcagct ccatatattg     480
tgagtaacat cacaatagga ggaggggtgg cgccctctaa gatggaggaa gtgtctatta     540
agcgaccgct aaataaaact ccttctcaaa aggctaagaa atcattcaca ccagtgactt     600
ttagggacgg acacatggaa aagttcttga gaggacttaa gaattgtgca acccgcaaca     660
acatgacagt acacttgatt ggaaagcgga aaaccgagct tgctttcaaa aggcgcgcta     720
gttcagatgc tgtgtacgct acactgcacc acatgcgtgg agttgatcgc aagcgcgata     780
ttgtgctcga agaatggatg aatgagtatg ttcacaattt gtcaagagtt ggcacatggg     840
gttcactatt tcacgccgaa tctctaaagc gaggtgatag tgggttaata ctgaatgcga     900
gagcactgag gggtaaattc ggacgatgta gcagaggatt tttcatagtt cgcggaaaat     960
cggatggaat tgtattggat gcaagatcca agctttctat ggcaactgta cttcatatgg    1020
aacagtattc aacatctgaa gcattttgga gcggtctaga gaagaagtgg agcgtgatgc    1080
gcaagccaac cgcgcatact tgtaaaccga cgtattcggt ttcgaattgt ggggaagtag    1140
ccgctattat agcgcaagcc ttatttccgt gccacaagtt gacgtgtggt gaatgctcga    1200
aagagatttg cgatctcact tcgagtgaat gcgtgcaaga gttatacaag aatatctctt    1260
tggcactgga aaggatgaac aatctacatc ccgaatttca acacattgtt aaggtgttga    1320
gcgttgttag gcagctcact gaagcatcca atcatgggat ggaagtattc gatgaaatct    1380
tcaaaatgat tggatccaaa acacagagtc ctttcactca tttaaataag ctcaatgaat    1440
ttatgttgaa agggaacgag aatacaagtg aggaatggtt gactgctcga caacgcttaa    1500
```

```
aggagctggt gagatttcag aagaatagaa ctgataatat aaagaaaggt gacttggcat   1560
cattcagaaa taagctttct gctcgtgcac agtacaattt gtatttatca tgcgataatc   1620
agcttgacaa gaatgctagt tttctatggg gtcagcgaga ataccatgca cgtcggtttt   1680
tcctaaactt ctttcaacaa atagacccat caaaaggtta tttgtcgtat gaagatcgga   1740
ccataccaaa tggttctcga agttagcta taggcaactt aattgttcca ctcgatttag   1800
ctgaattccg aaaacgcatg aaaggcatcg acactcagca accaccaatt ggcaagtact   1860
gtacaagcca attggatggg aattttgtgt atccgtgctg ctgcacgacg cttgatgatg   1920
gccaaccaat tcgatcagct gtttacgcac cgactaagaa acatttagtt gttggtaaca   1980
caggagacac aaagtacatc aacttgccta aaggagatac agagatgcta tatattgcac   2040
tcgatggcta ttgttacatt aacatttatc tggcaatgtt ggtcaatata agcgaggaag   2100
aggccaagga cttcacaaag aaagttcggg atattttcat gccaaagctt gggaagtggc   2160
caacattgat ggatttggct acgacatgtg ctcaacttcg gatattccac cctgatgtac   2220
atgacgcaga gctgcctcgt attctagtgg atcacaacac acaaacatgt catgtggtcg   2280
attcatatgg atcaattagt actgggtatc acattctgaa agctgcaact gtttcacaat   2340
tagtgttgtt tgctgacgac aacttggagt ctgagataaa gcactataga gttggtggaa   2400
ctgtagagaa tcataaagtg aaaatagatg accaacctgg tagatgtgga gtgagcgagt   2460
ttcatgctat acgcatgtta attaaaggga tctacaggcc aagtgtcatg tatgagttac   2520
tctccgaaga gccatacttg ttagtgttct ccattctctc acccctcgata ttgatagcga   2580 tgtacaatga tagggctttc gagctagctg ttcaaatatg gttggagaag gaacagtcaa   2640
ttccattgat tgccactatt ttaacaaatt tggcagcgaa ggtttctgtg ccacacaactc   2700 tcgttcaaca attgcagttg attgaattat ctgcagatca gctactgaat gtgacttgtg   2760
atgggtttcg ggtgagtttt gcttatcaat cagctctaac tctactcaca aggatgcgag   2820
atcaagccaa agcaaatagt gagttgataa gcggagggtt caatgaatat gaccaggatt   2880
tggcgtggac cttggaaaaa aattatcaag gcctcttaca cgaccaatgg aaagaattaa   2940
gctcgctgga aaaatttcgc tactattggt cctcaagaaa gcgaaagact cgtttgcggt   3000
caaatatcaa aagcagaagt tcgcccgttg ccagcgcaat atccagttta tcaccgaaac   3060
catttatggg aaaggttttc tcccacatga agcaggtgc agtgcgcacc aagcgaggaa   3120
ctaagagttt cattgacgca aggtgtttgg gtatttcaac ctactttgta ggatcactaa   3180
tgcgcaagtt tcctagtgcg aaagtactgc ttagtagttt attcgtattg ggagcgcttc   3240
taaatataac acgtgctgcg aataggataa taattgataa tcgcatttca cgcgaacatg   3300
cagcagcatt ggaattgtat aggaaagaag atacttgcca tgagttatac accgcactcg   3360
agcggaagtt gggagaaaaa ccaacctggg acgagtactg ctcatatgtg gctaagatta   3420
atcctgcaac gctagaattc attaaggact catatgatga aaaacaggtc atccaccaaa   3480
gatcaactga agatctcaag aaagttgaac acataatagc atttgttaca ctggcaataa   3540 tgcttttttga ttctgaaagg agtgattgtg tattcaaaac tttgaacaag tttaagggtg   3600
ttgtgtgctc actaggttca gaagttagac atcagtcttt ggatgatttt gtgaatacaa   3660
tggatgagaa gaatttcgtt gttgattttg aattgaatga tagtgtccaa aggaagaatc   3720
taacaactga gatcaccttt gaaaactggt gggatgagca agttgctcgg ggtttcacaa   3780
taccacacta tagaacagag gggaggttta tggaattcac aagagcaaca gcagctaaag   3840
tcgctagtga tatatcaatc tcatctgagc gcgacttttt gattcgagga gctgtgggtt   3900
```

```
ctggtaaatc cactgggtta ccacaccatt tgagcactta cggcagggtt ttgctgatag    3960
aaccaacacg gccactagca gaaaatgttt tcaaacagtt atctggtggt ccattttttc    4020
taaaacccac aatgagaatg cgtggtaata gtgtgtttgg gtcgtcgcct atttctgtaa    4080
tgacaagtgg gtttgctttg catttctttg ctaataacat cactcaactt caagagattc    4140
agtttataat tatagacgag tgccatgtta tggatgcatc ttcaatggca tttagaagct    4200
taattcatac ataccacact aattgtaagg ttttgaaggt ttcagcaaca ccacctggca    4260
gagaggtgga gttcacaaca caattcccag tgaaattagt ggttgaagat agtctgtctt    4320
ttaagacatt tgttgagagt caaggcacag gtagcaattg tgacatgatc caatacggaa    4380
ataacttatt agtgtatgta gctagttata atgaagtaga ccaactgtca aaattactag    4440
tagctcgtga gttcaatgtc acgaaagtag atggtaggac gatgaagcat ggtgagctcg    4500
agattgtgac acgaggaaca aagagtaagc cacactttgt tgtcgccact aatattattg    4560
aaaatggagt aactttggat atagatgttg ttattgactt tggaatgaaa gttagcccat    4620
ttttagatgt agataatagg tctgtagcat acaataaggt ctccattagt tacggagaac    4680
gaattcagcg gcttggaagg gtaggtcgca tacagaaggg caccgcactt cggataggtc    4740
acactgagaa agggctaata gaaatacctc aaatgatatc aactgaagct gctttgtatt    4800
gctttgcgta caatttacca gtcatgtcta gtggcgtctc cacaagcatg attaaaaatt    4860
gtacaatacc acaagttcgc acaatgcata catttgagtt gagtccattt ttcatgtaca    4920
attttgtgtc acatgatgga acaatgcatc cggttgtcca tgaaattctc aagcgctata    4980
aactgcgtga ttcggttatt ccattaagtg agagttccat cccatacaga gcttctagcg    5040
actggatcac ggctggtgac tacaggcgta ttggagtgaa actggatatc ccagatgaaa    5100
cgcgaattgc atttcatatc aaagacattc caccacaaat tcaccaacaa ttgtgggagt    5160
cagttctcaa gtataaggca tctgcagcat tcccaacatt gcgatcatca tcgattacaa    5220
agattgcata cacactgagc actgatttat acgcaattcc gcgtacttta gcagttgtgg    5280
aaagcctgct ggaagatgag aggacaaaac aatatcaatt caaaagcttg attgacaatg    5340
gttgctcaag tatgttctca gtggttggaa tttcaaatgc actcagagct aaatattcga    5400
aagattacac cgtggagaat ataaataagc ttgaagctgt caaagcacaa ctcaaagagt    5460
tccacaatct aaatggctct ggtgatgagt taaatttgat caaaagattc gagtcgttac    5520
aatttgtgca tcaccagtcc aagtcttctc ttgcgaaggc ccttggatta agaggcgttt    5580
ggaacaaatc actcattgtt cgcgatgcga tcattgcggc cggtgttgca tgtggtggtg    5640
cgtggctatt gtatacatgg ttcactggaa agatgtctga agtgagtcat cagggacgct    5700
ctaagacgaa aagaattcag gcattgaaat tcaggaaggc acgtgataag agagctggat    5760
ttgagattga taacaatgaa gatactattg aagagtactt cggctctgct tatactaaga    5820
aaggaaaagg taaaggcaca accgttggca tgggcaaaac aaacagacga ttcatcaaca    5880
tgtatgggtt tgagcccggg caattctctt atatcaaatt tgttgatcca ctcacaggtg    5940
cacaaatgga ggaaaatgtt tacgctgata ttgtcgatgt gcaagacaaa tttggtgaga    6000
ttcggaggca aatgataatt gatgacgagt tggataaccg acaaacagaa gtccataaca    6060
ctattcatgc ttacctcata aaagattggt caaataagga attaaaagtg gacttgactc    6120
cgcataatcc tcttcgggta agcgataagg caagtgccat aatgaagttc cctgagcggg    6180
aaggagaatt gcgccaaact ggacaagcag tggaggttga tgtcagcgac ataccaaagg    6240
aagttgtgaa gcacgaagcg aaaactttaa tgagggggcct tcgtgattac aatccaatag    6300
```

```
cccaaactgt tgcaagttg actgtaaaat ccgaattggg tgaaacatca acatatggtt      6360
taggttttgg tgggttaatc attgcaaatc accatttgtt caagagcttt aatggcagtc      6420
ttgaagttaa atcgcatcat ggggttttta gagtgccaaa cctgatggct ataagcgtct      6480
taccgttgaa ggggagagat atgatcataa ttaagatgcc aaaggatttt ccagttttcc      6540
cacaacgact caaattcaga gaacctgcgt caacagacag agtgtgtctc attggttcaa      6600
acttccaaga aagatacatt tctacaacag tgtcagaaac cagtgccact cacccagtcc      6660
cacgcagcac attttggaag cattggatct ccacagatga tggtcattgt ggtttgccta      6720
ttgttagcac aacagatgga tttatcctag ggctacatag tttagcaaat aataggaaca      6780
gtgaaaatta ttacactgct ttcgattctg attttgaaat gaaaatatta aggagtggag      6840
aaaacaccga gtgggtgaag aattggaagt ataatccaga cacagttttg tggggacctc      6900
tacaactcac caagggaaca ccgagtggaa tgtttaaaac caccaagatg attgaagact      6960
tactggcatt caagagtgaa tgtgtgaggg agcaagcaca cacatcacct tggatgcttg      7020
aagtcctgaa agagaatttg aaggccgttg catatatgaa gagtcaactc gtcaccaagc      7080
atgttgtgaa gggtgagtgt acgatgttta aacagtattt gcaggaaaac tccagggcaa      7140
atgagttttt ccagcctaag atgtgggcgt atggaaagag tatgttgaat aaggaagcct      7200
atatcaagga tataatgaaa tattcaaaag tcattgatgt aggagtagtc gattgcgacg      7260
catttgagga agctatcatt agagttattg tatacatgca gatccatggc tttcgcaaat      7320
gttcttacat cacagatgaa gaggagatat tcaaggcatt gaatatgaac acagctgttg      7380
gagctatgta tgggggaaag aaaaaggagt actttgaaaa gttcacaaca gaggataagg      7440
ctgagattct ccggcaaagc tgtttgaggt tgtacacggg taaactgggt gtgtggaatg      7500
ggtctctaaa agctgaactg agaagtaagg aaaagataga ggctaataag acacggactt      7560
tcacagcagc cccaattgat actttattag gtggtaaggt gtgtagat gatttcaaca      7620 accagtttta ttcgaaaaat attgaatgtt gttggacggt tgggatgacc aaattttatg      7680
gtggatggaa taagcttttg acagcttttgc ctgatggatg gatatattgt gatgcagatg      7740
gctcgcaatt cgatagttca ttgacaccct acctcataaa tgctgtattg actatacggt      7800
atgctttcat ggaagattgg gacattgggt ataagatgtt gcaaaacttg tacacagaaa      7860
taatctacac accaatatcc acgcctgatg gaacaatcgt gaagaagttc agaggcaata      7920
acagtgggca accttccacc gttgtagaca actcacttat ggttgtactt gctatgcatt      7980
atgcatttgt acgggaaggt gtggtatttg aagaaattga ctccatatgc aagttcttcg      8040
ttaatggaga tgatttgcta atagccgtga acccagaacg tgaaaactta ttggacacac      8100
tgtcaagtca ttttttctgat ttagggctca attatgattt ctcatctcgg acgagggata      8160
aatcagaatt gtggttcatg tcacattgtg ggattcctgt tgaaggtatg tatatacccta      8220 agcttgaaga ggagcgaatt gtatcaattc tccaatggga ccgagcggag ctaccagagt      8280
acagattgga ggctatttgt gcagcaatga ttgaatcatg gggatacccA caattaactc      8340
atgagattcg aagattctat agctggttaa ttgagaagaa cccatacgct gacttggcat      8400
ctgaaggaaa agctccatat atttctgaac tagctctaaa gaagctatat ctgaatcagg      8460
atgtacaaaa tgatgagctt caggtctacc tcagatattt cgctgaagca gatgaagagt      8520
ttgaatgtgg tacatatgaa gttcatcatc agagcagctc aagatcagac acattggacg      8580
ctggagagga gaaaagaaa aataaagaag tagccactgt gtccgatgga atgaaaaaga      8640
aggaggttga atcaacacgc gattctgatg tgaatgcggg aactgttgga acattcaccg      8700
```

```
ttccaagaat caaatcaatc actgagaaga tgcgtatgcc aaaacaaaag aaaaagggtg    8760
ttctcaactt ggctcattta cttgaataca aaccaagcca agtcgacata tcgaatactc    8820
gttcaaccca ggcacaattt gacaattggt ataatgaagt tatgaaagca tacgatctac    8880
aagaggaggc aatgggtaca gtgatgaatg cttaatggt ttggtgcatt gaaaatggca     8940
cgtccccaaa tattagtgga acatggacca tgatggatgg agacgaacag gtggaattcc    9000
cattaaagcc cgtgatagag aatgctaagc cgacttttcg gcagataatg gcgcattttt    9060
ctgatgtggc tgaggcatat atagaaatgc gcaataagca agaaccatac atgccacgat    9120
atggtttggt tcgaaattta cgagacatgg gtctggctcg atacgcattt gacttctatg    9180
aagtcacatc gcgtacgtca acacgtgctc gcgaagccca tatccaaatg aaagcagcag    9240
cattgaaatc tgctcaaaca aggctatttg gattggatgg tggcatagga acacaaggag    9300
aaaacacaga gcgccatacc actgaagatg tgagccccga catgcatacc ctgcttgggg    9360
tcagaaatat gtgactgatg tggtctctgg gatgaaatat tattatatgt agtatgcaat    9420
atatagtatg gcttttctcg ttccagtctt tatattaatg agagtaactt aagtaagtaa    9480
tttgtacttc aaggattaat caaggtgact ctctgacact ctcagtgagg tgacttgttt    9540
agtctgagtt tacttattgt gagtataaag aatctctcag aaaacgagag tgacttctag    9600
acacactcta ggaggtgatc gtagttggca tgagagggcc aaaaaaaaaa aaaaa         9655
```

<210> SEQ ID NO 2
<211> LENGTH: 3068
<212> TYPE: PRT
<213> ORGANISM: Pepper mottle virus

<400> SEQUENCE: 2

```
Met Ala Ile Asn Val Ile Gln Phe Gly Ser Phe Val Cys Asn Leu Pro
1               5                   10                  15

Lys Phe Gln Ser Ser Cys Thr Thr Met His Cys Pro Lys Gln Ser Ile
            20                  25                  30

Ser Thr Asn Val Val His Pro Ser Asn Pro Phe Ala Glu Leu Glu Glu
        35                  40                  45

Arg Leu Glu Pro Tyr Leu Gln Arg Arg Met Asp Ala Thr Ile Arg Leu
    50                  55                  60

Thr Arg Gly Gly Thr Leu Val Tyr Lys His Met Ser Glu Ala Lys Arg
65                  70                  75                  80

Ala Lys Lys Leu Arg Lys Lys Gln Arg Glu Glu Glu Val His Leu
                85                  90                  95

Phe Met Asn Ala Ala Pro Tyr Ile Val Ser Asn Ile Thr Ile Gly Gly
            100                 105                 110

Gly Val Ala Pro Ser Lys Met Glu Glu Val Ser Ile Lys Arg Pro Leu
        115                 120                 125

Asn Lys Thr Pro Ser Gln Lys Ala Lys Lys Ser Phe Thr Pro Val Thr
    130                 135                 140

Phe Arg Asp Gly His Met Glu Lys Phe Leu Arg Gly Leu Lys Asn Cys
145                 150                 155                 160

Ala Thr Arg Asn Asn Met Thr Val His Leu Ile Gly Lys Arg Lys Thr
                165                 170                 175

Glu Leu Ala Phe Lys Arg Arg Ala Ser Ser Asp Ala Val Tyr Ala Thr
            180                 185                 190

Leu His His Met Arg Gly Val Asp Arg Lys Arg Asp Ile Val Leu Glu
        195                 200                 205
```

-continued

| | | | | | | | | | | | | | |
|---|---|---|---|---|---|---|---|---|---|---|---|---|---|
|Glu|Trp|Met|Asn|Glu|Tyr|Val|His|Asn|Leu|Ser|Arg|Val|Gly|Thr|Trp|
| |210| | | |215| | | |220| | | | |

Gly Ser Leu Phe His Ala Glu Ser Leu Lys Arg Gly Asp Ser Gly Leu
225                 230                 235                 240

Ile Leu Asn Ala Arg Ala Leu Arg Gly Lys Phe Gly Arg Cys Ser Arg
                245                 250                 255

Gly Phe Phe Ile Val Arg Gly Lys Ser Asp Gly Ile Val Leu Asp Ala
            260                 265                 270

Arg Ser Lys Leu Ser Met Ala Thr Val Leu His Met Glu Gln Tyr Ser
        275                 280                 285

Thr Ser Glu Ala Phe Trp Ser Gly Leu Glu Lys Lys Trp Ser Val Met
290                 295                 300

Arg Lys Pro Thr Ala His Thr Cys Lys Pro Thr Tyr Ser Val Ser Asn
305                 310                 315                 320

Cys Gly Glu Val Ala Ala Ile Ile Ala Gln Ala Leu Phe Pro Cys His
                325                 330                 335

Lys Leu Thr Cys Gly Glu Cys Ser Lys Glu Ile Cys Asp Leu Thr Ser
                340                 345                 350

Ser Glu Cys Val Gln Glu Leu Tyr Lys Asn Ile Ser Leu Ala Leu Glu
            355                 360                 365

Arg Met Asn Asn Leu His Pro Glu Phe Gln His Ile Val Lys Val Leu
        370                 375                 380

Ser Val Val Arg Gln Leu Thr Glu Ala Ser Asn His Gly Met Glu Val
385                 390                 395                 400

Phe Asp Glu Ile Phe Lys Met Ile Gly Ser Lys Thr Gln Ser Pro Phe
                405                 410                 415

Thr His Leu Asn Lys Leu Asn Glu Phe Met Leu Lys Gly Asn Glu Asn
                420                 425                 430

Thr Ser Glu Glu Trp Leu Thr Ala Arg Gln Arg Leu Lys Glu Leu Val
            435                 440                 445

Arg Phe Gln Lys Asn Arg Thr Asp Asn Ile Lys Lys Gly Asp Leu Ala
        450                 455                 460

Ser Phe Arg Asn Lys Leu Ser Arg Ala Gln Tyr Asn Leu Tyr Leu
465                 470                 475                 480

Ser Cys Asp Asn Gln Leu Asp Lys Asn Ala Ser Phe Leu Trp Gly Gln
                485                 490                 495

Arg Glu Tyr His Ala Arg Arg Phe Phe Leu Asn Phe Gln Gln Ile
            500                 505                 510

Asp Pro Ser Lys Gly Tyr Leu Ser Tyr Glu Asp Arg Thr Ile Pro Asn
        515                 520                 525

Gly Ser Arg Lys Leu Ala Ile Gly Asn Leu Ile Val Pro Leu Asp Leu
530                 535                 540

Ala Glu Phe Arg Lys Arg Met Lys Gly Ile Asp Thr Gln Gln Pro Pro
545                 550                 555                 560

Ile Gly Lys Tyr Cys Thr Ser Gln Leu Asp Gly Asn Phe Val Tyr Pro
                565                 570                 575

Cys Cys Cys Thr Thr Leu Asp Asp Gly Gln Pro Ile Arg Ser Ala Val
                580                 585                 590

Tyr Ala Pro Thr Lys Lys His Leu Val Val Gly Asn Thr Gly Asp Thr
            595                 600                 605

Lys Tyr Ile Asn Leu Pro Lys Gly Asp Thr Glu Met Leu Tyr Ile Ala
        610                 615                 620

Leu Asp Gly Tyr Cys Tyr Ile Asn Ile Tyr Leu Ala Met Leu Val Asn
625                 630                 635                 640

```
Ile Ser Glu Glu Ala Lys Asp Phe Thr Lys Lys Val Arg Asp Ile
            645                 650                 655

Phe Met Pro Lys Leu Gly Lys Trp Pro Thr Leu Met Asp Leu Ala Thr
            660                 665                 670

Thr Cys Ala Gln Leu Arg Ile Phe His Pro Asp Val His Asp Ala Glu
            675                 680                 685

Leu Pro Arg Ile Leu Val Asp His Asn Thr Gln Thr Cys His Val Val
            690                 695                 700

Asp Ser Tyr Gly Ser Ile Ser Thr Gly Tyr His Ile Leu Lys Ala Ala
705                 710                 715                 720

Thr Val Ser Gln Leu Val Leu Phe Ala Asp Asp Asn Leu Glu Ser Glu
                725                 730                 735

Ile Lys His Tyr Arg Val Gly Thr Val Glu Asn His Lys Val Lys
            740                 745                 750

Ile Asp Asp Gln Pro Gly Arg Cys Gly Val Ser Glu Phe His Ala Ile
            755                 760                 765

Arg Met Leu Ile Lys Gly Ile Tyr Arg Pro Ser Val Met Tyr Glu Leu
            770                 775                 780

Leu Ser Glu Glu Pro Tyr Leu Leu Val Phe Ser Ile Leu Ser Pro Ser
785                 790                 795                 800

Ile Leu Ile Ala Met Tyr Asn Asp Arg Ala Phe Glu Leu Ala Val Gln
            805                 810                 815

Ile Trp Leu Glu Lys Glu Gln Ser Ile Pro Leu Ile Ala Thr Ile Leu
            820                 825                 830

Thr Asn Leu Ala Ala Lys Val Ser Val Ala Thr Thr Leu Val Gln Gln
            835                 840                 845

Leu Gln Leu Ile Glu Leu Ser Ala Asp Gln Leu Leu Asn Val Thr Cys
            850                 855                 860

Asp Gly Phe Arg Val Ser Phe Ala Tyr Gln Ser Ala Leu Thr Leu Leu
865                 870                 875                 880

Thr Arg Met Arg Asp Gln Ala Lys Ala Asn Ser Glu Leu Ile Ser Gly
                885                 890                 895

Gly Phe Asn Glu Tyr Asp Gln Asp Leu Ala Trp Thr Leu Glu Lys Asn
            900                 905                 910

Tyr Gln Gly Leu Leu His Asp Gln Trp Lys Glu Leu Ser Ser Leu Glu
            915                 920                 925

Lys Phe Arg Tyr Tyr Trp Ser Ser Arg Lys Lys Thr Arg Leu Arg
            930                 935                 940

Ser Asn Ile Lys Ser Arg Ser Pro Val Ala Ser Ala Ile Ser Ser
945                 950                 955                 960

Leu Ser Pro Lys Pro Phe Met Gly Lys Val Phe Ser His Met Lys Ala
            965                 970                 975

Gly Ala Val Arg Thr Lys Arg Gly Thr Lys Ser Phe Ile Asp Ala Arg
            980                 985                 990

Cys Leu Gly Ile Ser Thr Tyr Phe Val Gly Ser Leu Met Arg Lys Phe
            995                 1000                1005

Pro Ser Ala Lys Val Leu Leu Ser Ser Leu Phe Val Leu Gly Ala
            1010                1015                1020

Leu Leu Asn Ile Thr Arg Ala Ala Asn Arg Ile Ile Asp Asn
            1025                1030                1035

Arg Ile Ser Arg Glu His Ala Ala Ala Leu Glu Leu Tyr Arg Lys
            1040                1045                1050

Glu Asp Thr Cys His Glu Leu Tyr Thr Ala Leu Glu Arg Lys Leu
```

-continued

```
              1055                1060                1065

Gly Glu Lys Pro Thr Trp Asp Glu Tyr Cys Ser Tyr Val Ala Lys
        1070                1075                1080

Ile Asn Pro Ala Thr Leu Glu Phe Ile Lys Asp Ser Tyr Asp Glu
        1085                1090                1095

Lys Gln Val Ile His Gln Arg Ser Thr Glu Asp Leu Lys Lys Val
        1100                1105                1110

Glu His Ile Ile Ala Phe Val Thr Leu Ala Ile Met Leu Phe Asp
        1115                1120                1125

Ser Glu Arg Ser Asp Cys Val Phe Lys Thr Leu Asn Lys Phe Lys
        1130                1135                1140

Gly Val Val Cys Ser Leu Gly Ser Glu Val Arg His Gln Ser Leu
        1145                1150                1155

Asp Asp Phe Val Asn Thr Met Asp Glu Lys Asn Phe Val Val Asp
        1160                1165                1170

Phe Glu Leu Asn Asp Ser Val Gln Arg Lys Asn Leu Thr Thr Glu
        1175                1180                1185

Ile Thr Phe Glu Asn Trp Trp Asp Glu Gln Val Ala Arg Gly Phe
        1190                1195                1200

Thr Ile Pro His Tyr Arg Thr Glu Gly Arg Phe Met Glu Phe Thr
        1205                1210                1215

Arg Ala Thr Ala Ala Lys Val Ala Ser Asp Ile Ser Ile Ser Ser
        1220                1225                1230

Glu Arg Asp Phe Leu Ile Arg Gly Ala Val Gly Ser Gly Lys Ser
        1235                1240                1245

Thr Gly Leu Pro His His Leu Ser Thr Tyr Gly Arg Val Leu Leu
        1250                1255                1260

Ile Glu Pro Thr Arg Pro Leu Ala Glu Asn Val Phe Lys Gln Leu
        1265                1270                1275

Ser Gly Gly Pro Phe Phe Leu Lys Pro Thr Met Arg Met Arg Gly
        1280                1285                1290

Asn Ser Val Phe Gly Ser Ser Pro Ile Ser Val Met Thr Ser Gly
        1295                1300                1305

Phe Ala Leu His Phe Phe Ala Asn Asn Ile Thr Gln Leu Gln Glu
        1310                1315                1320

Ile Gln Phe Ile Ile Ile Asp Glu Cys His Val Met Asp Ala Ser
        1325                1330                1335

Ser Met Ala Phe Arg Ser Leu Ile His Thr Tyr His Thr Asn Cys
        1340                1345                1350

Lys Val Leu Lys Val Ser Ala Thr Pro Pro Gly Arg Glu Val Glu
        1355                1360                1365

Phe Thr Thr Gln Phe Pro Val Lys Leu Val Val Glu Asp Ser Leu
        1370                1375                1380

Ser Phe Lys Thr Phe Val Glu Ser Gln Gly Thr Gly Ser Asn Cys
        1385                1390                1395

Asp Met Ile Gln Tyr Gly Asn Asn Leu Leu Val Tyr Val Ala Ser
        1400                1405                1410

Tyr Asn Glu Val Asp Gln Leu Ser Lys Leu Leu Val Ala Arg Glu
        1415                1420                1425

Phe Asn Val Thr Lys Val Asp Gly Arg Thr Met Lys His Gly Glu
        1430                1435                1440

Leu Glu Ile Val Thr Arg Gly Thr Lys Ser Lys Pro His Phe Val
        1445                1450                1455
```

-continued

Val Ala Thr Asn Ile Ile Glu Asn Gly Val Thr Leu Asp Ile Asp
1460                1465                1470

Val Val Ile Asp Phe Gly Met Lys Val Ser Pro Phe Leu Asp Val
1475                1480                1485

Asp Asn Arg Ser Val Ala Tyr Asn Lys Val Ser Ile Ser Tyr Gly
1490                1495                1500

Glu Arg Ile Gln Arg Leu Gly Arg Val Gly Arg Ile Gln Lys Gly
1505                1510                1515

Thr Ala Leu Arg Ile Gly His Thr Glu Lys Gly Leu Ile Glu Ile
1520                1525                1530

Pro Gln Met Ile Ser Thr Glu Ala Ala Leu Tyr Cys Phe Ala Tyr
1535                1540                1545

Asn Leu Pro Val Met Ser Ser Gly Val Ser Thr Ser Met Ile Lys
1550                1555                1560

Asn Cys Thr Ile Pro Gln Val Arg Thr Met His Thr Phe Glu Leu
1565                1570                1575

Ser Pro Phe Phe Met Tyr Asn Phe Val Ser His Asp Gly Thr Met
1580                1585                1590

His Pro Val Val His Glu Ile Leu Lys Arg Tyr Lys Leu Arg Asp
1595                1600                1605

Ser Val Ile Pro Leu Ser Glu Ser Ser Ile Pro Tyr Arg Ala Ser
1610                1615                1620

Ser Asp Trp Ile Thr Ala Gly Asp Tyr Arg Arg Ile Gly Val Lys
1625                1630                1635

Leu Asp Ile Pro Asp Glu Thr Arg Ile Ala Phe His Ile Lys Asp
1640                1645                1650

Ile Pro Pro Gln Ile His Gln Gln Leu Trp Glu Ser Val Leu Lys
1655                1660                1665

Tyr Lys Ala Ser Ala Ala Phe Pro Thr Leu Arg Ser Ser Ser Ile
1670                1675                1680

Thr Lys Ile Ala Tyr Thr Leu Ser Thr Asp Leu Tyr Ala Ile Pro
1685                1690                1695

Arg Thr Leu Ala Val Val Glu Ser Leu Leu Glu Asp Glu Arg Thr
1700                1705                1710

Lys Gln Tyr Gln Phe Lys Ser Leu Ile Asp Asn Gly Cys Ser Ser
1715                1720                1725

Met Phe Ser Val Val Gly Ile Ser Asn Ala Leu Arg Ala Lys Tyr
1730                1735                1740

Ser Lys Asp Tyr Thr Val Glu Asn Ile Asn Lys Leu Glu Ala Val
1745                1750                1755

Lys Ala Gln Leu Lys Glu Phe His Asn Leu Asn Gly Ser Gly Asp
1760                1765                1770

Glu Leu Asn Leu Ile Lys Arg Phe Glu Ser Leu Gln Phe Val His
1775                1780                1785

His Gln Ser Lys Ser Ser Leu Ala Lys Ala Leu Gly Leu Arg Gly
1790                1795                1800

Val Trp Asn Lys Ser Leu Ile Val Arg Asp Ala Ile Ile Ala Ala
1805                1810                1815

Gly Val Ala Cys Gly Gly Ala Trp Leu Leu Tyr Thr Trp Phe Thr
1820                1825                1830

Gly Lys Met Ser Glu Val Ser His Gln Gly Arg Ser Lys Thr Lys
1835                1840                1845

Arg Ile Gln Ala Leu Lys Phe Arg Lys Ala Arg Asp Lys Arg Ala
1850                1855                1860

```
Gly Phe Glu Ile Asp Asn Asn Glu Asp Thr Ile Glu Glu Tyr Phe
    1865            1870                1875

Gly Ser Ala Tyr Thr Lys Lys Gly Lys Gly Lys Gly Thr Thr Val
    1880            1885                1890

Gly Met Gly Lys Thr Asn Arg Arg Phe Ile Asn Met Tyr Gly Phe
    1895            1900                1905

Glu Pro Gly Gln Phe Ser Tyr Ile Lys Phe Val Asp Pro Leu Thr
    1910            1915                1920

Gly Ala Gln Met Glu Glu Asn Val Tyr Ala Asp Ile Val Asp Val
    1925            1930                1935

Gln Asp Lys Phe Gly Glu Ile Arg Arg Gln Met Ile Ile Asp Asp
    1940            1945                1950

Glu Leu Asp Asn Arg Gln Thr Glu Val His Asn Thr Ile His Ala
    1955            1960                1965

Tyr Leu Ile Lys Asp Trp Ser Asn Lys Ala Leu Lys Val Asp Leu
    1970            1975                1980

Thr Pro His Asn Pro Leu Arg Val Ser Asp Lys Ala Ser Ala Ile
    1985            1990                1995

Met Lys Phe Pro Glu Arg Glu Gly Glu Leu Arg Gln Thr Gly Gln
    2000            2005                2010

Ala Val Glu Val Asp Val Ser Asp Ile Pro Lys Glu Val Val Lys
    2015            2020                2025

His Glu Ala Lys Thr Leu Met Arg Gly Leu Arg Asp Tyr Asn Pro
    2030            2035                2040

Ile Ala Gln Thr Val Cys Lys Leu Thr Val Lys Ser Glu Leu Gly
    2045            2050                2055

Glu Thr Ser Thr Tyr Gly Leu Gly Phe Gly Gly Leu Ile Ile Ala
    2060            2065                2070

Asn His His Leu Phe Lys Ser Phe Asn Gly Ser Leu Glu Val Lys
    2075            2080                2085

Ser His His Gly Val Phe Arg Val Pro Asn Leu Met Ala Ile Ser
    2090            2095                2100

Val Leu Pro Leu Lys Gly Arg Asp Met Ile Ile Ile Lys Met Pro
    2105            2110                2115

Lys Asp Phe Pro Val Phe Pro Gln Arg Leu Lys Phe Arg Glu Pro
    2120            2125                2130

Ala Ser Thr Asp Arg Val Cys Leu Ile Gly Ser Asn Phe Gln Glu
    2135            2140                2145

Arg Tyr Ile Ser Thr Thr Val Ser Glu Thr Ser Ala Thr His Pro
    2150            2155                2160

Val Pro Arg Ser Thr Phe Trp Lys His Trp Ile Ser Thr Asp Asp
    2165            2170                2175

Gly His Cys Gly Leu Pro Ile Val Ser Thr Thr Asp Gly Phe Ile
    2180            2185                2190

Leu Gly Leu His Ser Leu Ala Asn Asn Arg Asn Ser Glu Asn Tyr
    2195            2200                2205

Tyr Thr Ala Phe Asp Ser Asp Phe Glu Met Lys Ile Leu Arg Ser
    2210            2215                2220

Gly Glu Asn Thr Glu Trp Val Lys Asn Trp Lys Tyr Asn Pro Asp
    2225            2230                2235

Thr Val Leu Trp Gly Pro Leu Gln Leu Thr Lys Gly Thr Pro Ser
    2240            2245                2250

Gly Met Phe Lys Thr Thr Lys Met Ile Glu Asp Leu Leu Ala Phe
```

```
                2255                2260                2265
Lys Ser Glu Cys Val Arg Glu Gln Ala His Thr Ser Pro Trp Met
2270                2275                2280

Leu Glu Val Leu Lys Glu Asn Leu Lys Ala Val Ala Tyr Met Lys
2285                2290                2295

Ser Gln Leu Val Thr Lys His Val Val Lys Gly Glu Cys Thr Met
2300                2305                2310

Phe Lys Gln Tyr Leu Gln Glu Asn Ser Arg Ala Asn Glu Phe Phe
2315                2320                2325

Gln Pro Lys Met Trp Ala Tyr Gly Lys Ser Met Leu Asn Lys Glu
2330                2335                2340

Ala Tyr Ile Lys Asp Ile Met Lys Tyr Ser Lys Val Ile Asp Val
2345                2350                2355

Gly Val Val Asp Cys Asp Ala Phe Glu Glu Ala Ile Ile Arg Val
2360                2365                2370

Ile Val Tyr Met Gln Ile His Gly Phe Arg Lys Cys Ser Tyr Ile
2375                2380                2385

Thr Asp Glu Glu Glu Ile Phe Lys Ala Leu Asn Met Asn Thr Ala
2390                2395                2400

Val Gly Ala Met Tyr Gly Gly Lys Lys Lys Glu Tyr Phe Glu Lys
2405                2410                2415

Phe Thr Thr Glu Asp Lys Ala Glu Ile Leu Arg Gln Ser Cys Leu
2420                2425                2430

Arg Leu Tyr Thr Gly Lys Leu Gly Val Trp Asn Gly Ser Leu Lys
2435                2440                2445

Ala Glu Leu Arg Ser Lys Glu Lys Ile Glu Ala Asn Lys Thr Arg
2450                2455                2460

Thr Phe Thr Ala Ala Pro Ile Asp Thr Leu Leu Gly Gly Lys Val
2465                2470                2475

Cys Val Asp Asp Phe Asn Asn Gln Phe Tyr Ser Lys Asn Ile Glu
2480                2485                2490

Cys Cys Trp Thr Val Gly Met Thr Lys Phe Tyr Gly Gly Trp Asn
2495                2500                2505

Lys Leu Leu Thr Ala Leu Pro Asp Gly Trp Ile Tyr Cys Asp Ala
2510                2515                2520

Asp Gly Ser Gln Phe Asp Ser Ser Leu Thr Pro Tyr Leu Ile Asn
2525                2530                2535

Ala Val Leu Thr Ile Arg Tyr Ala Phe Met Glu Asp Trp Asp Ile
2540                2545                2550

Gly Tyr Lys Met Leu Gln Asn Leu Tyr Thr Glu Ile Ile Tyr Thr
2555                2560                2565

Pro Ile Ser Thr Pro Asp Gly Thr Ile Val Lys Lys Phe Arg Gly
2570                2575                2580

Asn Asn Ser Gly Gln Pro Ser Thr Val Val Asp Asn Ser Leu Met
2585                2590                2595

Val Val Leu Ala Met His Tyr Ala Phe Val Arg Glu Gly Val Val
2600                2605                2610

Phe Glu Glu Ile Asp Ser Ile Cys Lys Phe Phe Val Asn Gly Asp
2615                2620                2625

Asp Leu Leu Ile Ala Val Asn Pro Glu Arg Glu Asn Leu Leu Asp
2630                2635                2640

Thr Leu Ser Ser His Phe Ser Asp Leu Gly Leu Asn Tyr Asp Phe
2645                2650                2655
```

```
Ser Ser Arg Thr Arg Asp Lys Ser Glu Leu Trp Phe Met Ser His
        2660                2665                2670

Cys Gly Ile Pro Val Glu Gly Met Tyr Ile Pro Lys Leu Glu Glu
        2675                2680                2685

Glu Arg Ile Val Ser Ile Leu Gln Trp Asp Arg Ala Glu Leu Pro
        2690                2695                2700

Glu Tyr Arg Leu Glu Ala Ile Cys Ala Ala Met Ile Glu Ser Trp
        2705                2710                2715

Gly Tyr Pro Gln Leu Thr His Glu Ile Arg Arg Phe Tyr Ser Trp
        2720                2725                2730

Leu Ile Glu Lys Asn Pro Tyr Ala Asp Leu Ala Ser Glu Gly Lys
        2735                2740                2745

Ala Pro Tyr Ile Ser Glu Leu Ala Leu Lys Lys Leu Tyr Leu Asn
        2750                2755                2760

Gln Asp Val Gln Asn Asp Glu Leu Gln Val Tyr Leu Arg Tyr Phe
        2765                2770                2775

Ala Glu Ala Asp Glu Glu Phe Glu Cys Gly Thr Tyr Glu Val His
        2780                2785                2790

His Gln Ser Ser Ser Arg Ser Asp Thr Leu Asp Ala Gly Glu Glu
        2795                2800                2805

Lys Lys Lys Asn Lys Glu Val Ala Thr Val Ser Asp Gly Met Lys
        2810                2815                2820

Lys Lys Glu Val Glu Ser Thr Arg Asp Ser Asp Val Asn Ala Gly
        2825                2830                2835

Thr Val Gly Thr Phe Thr Val Pro Arg Ile Lys Ser Ile Thr Glu
        2840                2845                2850

Lys Met Arg Met Pro Lys Gln Lys Lys Lys Gly Val Leu Asn Leu
        2855                2860                2865

Ala His Leu Leu Glu Tyr Lys Pro Ser Gln Val Asp Ile Ser Asn
        2870                2875                2880

Thr Arg Ser Thr Gln Ala Gln Phe Asp Asn Trp Tyr Asn Glu Val
        2885                2890                2895

Met Lys Ala Tyr Asp Leu Gln Glu Glu Ala Met Gly Thr Val Met
        2900                2905                2910

Asn Gly Leu Met Val Trp Cys Ile Glu Asn Gly Thr Ser Pro Asn
        2915                2920                2925

Ile Ser Gly Thr Trp Thr Met Met Asp Gly Asp Glu Gln Val Glu
        2930                2935                2940

Phe Pro Leu Lys Pro Val Ile Glu Asn Ala Lys Pro Thr Phe Arg
        2945                2950                2955

Gln Ile Met Ala His Phe Ser Asp Val Ala Glu Ala Tyr Ile Glu
        2960                2965                2970

Met Arg Asn Lys Gln Glu Pro Tyr Met Pro Arg Tyr Gly Leu Val
        2975                2980                2985

Arg Asn Leu Arg Asp Met Gly Leu Ala Arg Tyr Ala Phe Asp Phe
        2990                2995                3000

Tyr Glu Val Thr Ser Arg Thr Ser Thr Arg Ala Arg Glu Ala His
        3005                3010                3015

Ile Gln Met Lys Ala Ala Ala Leu Lys Ser Ala Gln Thr Arg Leu
        3020                3025                3030

Phe Gly Leu Asp Gly Gly Ile Gly Thr Gln Gly Glu Asn Thr Glu
        3035                3040                3045

Arg His Thr Thr Glu Asp Val Ser Pro Asp Met His Thr Leu Leu
        3050                3055                3060
```

-continued

```
Gly Val  Arg Asn Met
    3065

<210> SEQ ID NO 3
<211> LENGTH: 10375
<212> TYPE: DNA
<213> ORGANISM: Artificial Sequence
<220> FEATURE:
<223> OTHER INFORMATION: PoPMv-GFP

<400> SEQUENCE: 3
aaattaaaac ataacataca acataaacga aagcaatcaa attttcaagc aatttccttg     60
aactctttaa ttctcttcta caagttaagc attttgatta acactactgt cttaatttga    120
atattttaat cattttcagt ttcttctact agcactctac actagcaatg gcaattaacg    180
ttattcagtt tggttcattt gtgtgcaatc ttccaaagtt tcaatcatcg tgcacaacta    240
tgcactgccc aaagcagagc ataagcacca atgtagtgca cccaagtaac ccattcgctg    300
aactcgagga acgtctcgaa ccatacttgc aaaggaggat ggatgcaaca atacgcctaa    360
ctagaggcgg gacgcttgtg tataaacaca tgagcgaagc taaacgcgcc aagaagctta    420
gaaagaagca gcgtgaggaa gaggaggtgc atttgttcat gaatgcagct ccatatattg    480
tgagtaacat cacaatagga ggaggggtgg cgccctctaa gatggaggaa gtgtctatta    540
agcgaccgct aaataaaact ccttctcaaa aggctaagaa atcattcaca ccagtgactt    600
ttagggacgg acacatggaa aagttcttga gaggacttaa gaattgtgca acccgcaaca    660
acatgacagt acacttgatt ggaaagcgga aaaccgagct tgctttcaaa aggcgcgcta    720
gttcagatgc tgtgtacgct acactgcacc acatgcgtgg agttgatcgc aagcgcgata    780
ttgtgctcga agaatggatg aatgagtatg ttcacaattt gtcaagagtt ggcacatggg    840
gttcactatt tcacgccgaa tctctaaagc gaggtgatag tgggttaata ctgaatgcga    900
gagcactgag ggtaaattc ggacgatgta gcagaggatt tttcatagtt cgcggaaaat    960
cggatggaat tgtattggat gcaagatcca agctttctat ggcaactgta cttcatatgg   1020
aacagtattc aacatctgaa gcattttgga gcggtctaga gaagaagtgg agcgtgatgc   1080
gcaagccaac cgcgcatact tgtaaaccga cgtattcggt ttcgaattgt ggggaagtag   1140
ccgctattat agcgcaagcc ttatttccgt gccacaagtt gacgtgtggt gaatgctcga   1200
aagagatttg cgatctcact tcgagtgaat gcgtgcaaga gttatacaag aatatctctt   1260
tggcactgga aaggatgaac aatctacatc ccgaatttca acacattgtt aaggtgttga   1320
gcgttgttag gcagctcact gaagcatcca atcatgggat ggaagtattc gatgaaatct   1380
tcaaaatgat tggatccaaa acacagagtc ctttcactca tttaaataag ctcaatgaat   1440
ttatgttgaa agggaacgag aatacaagtg aggaatggtt gactgctcga caacgcttaa   1500
aggagctggt gagatttcag aagaatagaa ctgataatat aaagaaaggt gacttggcat   1560
cattcagaaa taagctttct gctcgtgcac agtacaattt gtatttatca tgcgataatc   1620
agcttgacaa gaatgctagt tttctatggg gtcagcgaga ataccatgca cgtcggtttt   1680
tcctaaactt ctttcaacaa atagacccat caaaaggtta tttgtcgtat gaagatcgga   1740
ccataccaaa tggttctcga aagttagcta taggcaactt aattgttcca ctcgatttag   1800
ctgaattccg aaaacgcatg aaaggcatcg acactcagca accaccaatt ggcaagtact   1860
gtacaagcca attggatggg aattttgtgt atccgtgctg ctgcacgacg cttgatgatg   1920
gccaaccaat tcgatcagct gtttacgcac cgactaagaa acatttagtt gttggtaaca   1980
```

-continued

```
caggagacac aaagtacatc aacttgccta aaggagatac agagatgcta tatattgcac      2040
tcgatggcta ttgttacatt aacatttatc tggcaatgtt ggtcaatata agcgaggaag      2100
aggccaagga cttcacaaag aaagttcggg atattttcat gccaaagctt gggaagtggc      2160
caacattgat ggatttggct acgacatgtg ctcaacttcg atattccac cctgatgtac       2220 atgacgcaga gctgcctcgt attctagtgg atcacaacac acaaacatgt catgtggtcg      2280
attcatatgg atcaattagt actgggtatc acattctgaa agctgcaact gtttcacaat      2340
tagtgttgtt tgctgacgac aacttggagt ctgagataaa gcactataga gttggtggaa      2400
ctgtagagaa tcataaagtg aaaatagatg accaacctgg tagatgtgga gtgagcgagt      2460
ttcatgctat acgcatgtta attaaaggga tctacaggcc aagtgtcatg tatgagttac      2520
tctccgaaga gccatacttg ttagtgttct ccattctctc accctcgata ttgatagcga      2580
tgtacaatga tagggctttc gagctagctg ttcaaatatg gttggagaag aacagtcaa      2640 ttccattgat tgccactatt ttaacaaatt tggcagcgaa ggtttctgtg gccacaactc      2700
tcgttcaaca attgcagttg attgaattat ctgcagatca gctactgaat gtgacttgtg      2760
atgggtttcg ggtgagtttt gcttatcaat cagctctaac tctactcaca aggatgcgag      2820
atcaagccaa agcaaatagt gagttgataa gcggagggtt caatgaatat gaccaggatt      2880
tggcgtggac cttggaaaaa aattatcaag gcctcttaca cgaccaatgg aaagaattaa      2940
gctcgctgga aaaatttcgc tactattggt cctcaagaaa gcgaaagact cgtttgcggt      3000
caaatatcaa aagcagaagt tcgcccgttg ccagcgcaat atccagttta tcaccgaaac      3060
catttatggg aaaggttttc tcccacatga aagcaggtgc agtgcgcacc aagcgaggaa      3120
ctaagagttt cattgacgca aggtgtttgg gtatttcaac ctactttgta ggatcactaa      3180
tgcgcaagtt tcctagtgcg aaagtactgc ttagtagttt attcgtattg ggagcgcttc      3240
taaatataac acgtgctgcg aataggataa taattgataa tcgcatttca cgcgaacatg      3300
cagcagcatt ggaattgtat aggaaagaag atacttgcca tgagttatac accgcactcg      3360
agcggaagtt gggagaaaaa ccaacctggg acgagtactg ctcatatgtg ctaagatta       3420 atcctgcaac gctagaattc attaaggact catatgatga aaaacaggtc atccaccaaa      3480
gatcaactga agatctcaag aaagttgaac acataatagc atttgttaca ctggcaataa      3540 tgcttttga ttctgaaagg agtgattgtg tattcaaaac tttgaacaag tttaagggtg       3600
ttgtgtgctc actaggttca gaagttagac atcagtcttt ggatgatttt gtgaatacaa      3660
tggatgagaa gaatttcgtt gttgattttg aattgaatga tagtgtccaa aggaagaatc      3720
taacaactga gatcaccttt gaaaactggt gggatgagca agttgctcgg ggtttcacaa      3780
taccacacta tagaacagag gggaggttta tggaattcac aagagcaaca gcagctaaag      3840
tcgctagtga tatatcaatc tcatctgagc gcgactttt gattcgagga gctgtgggtt       3900
ctggtaaatc cactgggtta ccacaccatt tgagcactta cggcagggtt ttgctgatag      3960
aaccaacacg gccactagca gaaaatgttt tcaaacagtt atctggtggt ccatttttc       4020 taaaacccac aatgagaatg cgtggtaata gtgtgtttgg gtcgtcgcct atttctgtaa      4080
tgacaagtgg gtttgctttg catttctttg ctaataacat cactcaactt caagagattc      4140
agtttataat tatagacgag tgccatgtta tggatgcatc ttcaatggca tttagaagct      4200
taattcatac ataccacact aattgtaagg ttttgaaggt ttcagcaaca ccacctggca      4260
gagaggtgga gttcacaaca caattcccag tgaaattagt ggttgaagat agtctgtctt      4320
ttaagacatt tgttgagagt caaggcacag gtagcaattg tgacatgatc caatacggaa      4380
```

```
ataacttatt agtgtatgta gctagttata atgaagtaga ccaactgtca aaattactag    4440
tagctcgtga gttcaatgtc acgaaagtag atggtaggac gatgaagcat ggtgagctcg    4500
agattgtgac acgaggaaca aagagtaagc cacactttgt tgtcgccact aatattattg    4560
aaaatggagt aactttggat atagatgttg ttattgactt tggaatgaaa gttagcccat    4620
ttttagatgt agataatagg tctgtagcat acaataaggt ctccattagt tacggagaac    4680
gaattcagcg gcttggaagg gtaggtcgca tacagaaggg caccgcactt cggataggtc    4740
acactgagaa agggctaata gaaataccte aaatgatatc aactgaagct gctttgtatt    4800
gctttgcgta caatttacca gtcatgtcta gtggcgtctc cacaagcatg attaaaaatt    4860
gtacaatacc acaagttcgc acaatgcata catttgagtt gagtccattt ttcatgtaca    4920
attttgtgtc acatgatgga acaatgcatc cggttgtcca tgaaattctc aagcgctata    4980
aactgcgtga ttcggttatt ccattaagtg agagttccat cccatacaga gcttctagcg    5040
actggatcac ggctggtgac tacaggcgta ttggagtgaa actggatatc ccagatgaaa    5100
cgcgaattgc atttcatatc aaagacattc caccacaaat tcaccaacaa ttgtgggagt    5160
cagttctcaa gtataaggca tctgcagcat tcccaacatt gcgatcatca tcgattacaa    5220
agattgcata cacactgagc actgatttat acgcaattcc gcgtacttta gcagttgtgg    5280
aaagcctgct ggaagatgag aggacaaaac aatatcaatt caaaagcttg attgacaatg    5340
gttgctcaag tatgttctca gtggttggaa tttcaaatgc actcagagct aaatattcga    5400
aagattacac cgtggagaat ataaataagc ttgaagctgt caaagcacaa ctcaaagagt    5460
tccacaatct aaatggctct ggtgatgagt taaatttgat caaaagattc gagtcgttac    5520
aatttgtgca tcaccagtcc aagtcttctc ttgcgaaggc ccttggatta agaggcgttt    5580
ggaacaaatc actcattgtt cgcgatgcga tcattgcggc cggtgttgca tgtggtggtg    5640
cgtggctatt gtatacatgg ttcactggaa agatgtctga agtgagtcat cagggacgct    5700
ctaagacgaa aagaattcag gcattgaaat tcaggaaggc acgtgataag agagctggat    5760
ttgagattga taacaatgaa gatactattg aagagtactt cggctctgct tatactaaga    5820
aaggaaaagg taaaggcaca accgttggca tgggcaaaac aaacagacga ttcatcaaca    5880
tgtatgggtt tgagcccggg caattctctt atatcaaatt tgttgatcca ctcacaggtg    5940
cacaaatgga ggaaaatgtt tacgctgata ttgtcgatgt gcaagacaaa tttggtgaga    6000
ttcggaggca aatgataatt gatgacgagt tggataaccg acaaacagaa gtccataaca    6060
ctattcatgc ttacctcata aaagattggt caaataaggc attaaaagtg gacttgactc    6120
cgcataatcc tcttcgggta agcgataagg caagtgccat aatgaagttc cctgagcggg    6180
aaggagaatt gcgccaaact ggacaagcag tggaggttga tgtcagcgac ataccaaagg    6240
aagttgtgaa gcacgaagcg aaaactttaa tgaggggcct tcgtgattac aatccaatag    6300
cccaaactgt ttgcaagttg actgtaaaat ccgaattggg tgaaacatca acatatggtt    6360
taggttttgg tgggttaatc attgcaaatc accatttgtt caagagcttt aatggcagtc    6420
ttgaagttaa atcgcatcat ggggttttta gagtgccaaa cctgatggct ataagcgtct    6480
taccgttgaa ggggagagat atgatcataa ttaagatgcc aaaggatttt ccagttttcc    6540
cacaacgact caaattcaga gaacctgcgt caacagacag agtgtgtctc attggttcaa    6600
acttccaaga aagatacatt tctacaacag tgtcagaaac cagtgccact cacccagtcc    6660
cacgcagcac attttggaag cattggatct ccacagatga tggtcattgt ggtttgccta    6720
ttgttagcac aacagatgga tttatcctag ggctacatag tttagcaaat aataggaaca    6780
```

```
gtgaaaatta ttacactgct ttcgattctg attttgaaat gaaaatatta aggagtggag      6840
aaaacaccga gtgggtgaag aattggaagt ataatccaga cacagttttg tggggacctc      6900
tacaactcac caagggaaca ccgagtggaa tgtttaaaac caccaagatg attgaagact      6960
tactggcatt caagagtgaa tgtgtgaggg agcaagcaca cacatcacct tggatgcttg      7020
aagtcctgaa agagaatttg aaggccgttg catatatgaa gagtcaactc gtcaccaagc      7080
atgttgtgaa gggtgagtgt acgatgttta aacagtattt gcaggaaaac tccagggcaa      7140
atgagttttt ccagcctaag atgtgggcgt atggaaagag tatgttgaat aaggaagcct      7200
atatcaagga tataatgaaa tattcaaaag tcattgatgt aggagtagtc gattgcgacg      7260
catttgagga agctatcatt agagttattg tatacatgca gatccatggc tttcgcaaat      7320
gttcttacat cacagatgaa gaggagatat tcaaggcatt gaatatgaac acagctgttg      7380
gagctatgta tgggggaaag aaaaaggagt actttgaaaa gttcacaaca gaggataagg      7440
ctgagattct ccggcaaagc tgtttgaggt tgtacacggg taaactgggt gtgtggaatg      7500
ggtctctaaa agctgaactg aggagtaagg aaaagataga ggctaataag acacggactt      7560
tcacagcagc cccaattgat actttattag gtggtaaggt gtgtagat gatttcaaca      7620 accagtttta ttcgaaaaat attgaatgtt gttggacggt tgggatgacc aaatttatg      7680 gtggatggaa taagcttttg acagcttttgc ctgatggatg gatatattgt gatgcagatg      7740
gctcgcaatt cgatagttca ttgacacctt acctcataaa tgctgtattg actatacggt      7800
atgctttcat ggaagattgg gacattgggt ataagatgtt gcaaaacttg tacacagaaa      7860
taatctacac accaatatcc acgcctgatg gaacaatcgt gaagaagttc agaggcaata      7920 acagтggggca accttccacc gttgtagaca actcacttat ggttgtactt gctatgcatt      7980
atgcatttgt acgggaaggt gtggtatttg aagaaattga ctccatatgc aagttcttcg      8040

ttaatggaga tgatttgcta atagccgtga acccaggacg tgaaaactta ttggacacac      8100

tgtcaagtca ттттттcтgaт ttagggctca attatgattt ctcatctcgg acgagggata      8160
aatcagaatt gtggttcatg tcacattgtg ggattcctgt tgaaggtatg tata taccta      8220 agcttgaaga ggagcgaatt gtatcaattc tccaatggga ccgagcggag ctaccagagt      8280
acagattgga ggctatttgt gcagcaatga ttgaatcatg gggataccca caattaactc      8340

atgagattcg aagattctat agctggttaa ttgagaagaa cccatacgct gacttggcat      8400
ctgaaggaaa agctccatat atttctgaac tagctctaaa gaagctatat ctgaatcagg      8460

atgtacaaaa tgatgagctt caggtctacc tcagatattt cgctgaagca gatgaagagt      8520

ttgaatgtgg tacatatgaa gtccatcatc agagcagcat ggagagcgac gagagcggcc      8580

tgcccgccat ggagatcgag tgccgcatca ccggcaccct gaacggcgtg gagttcgagc      8640

tggtgggcgg cggagagggc acccccgagc agggccgcat gaccaacaag atgaagagca      8700
ccaaaggcgc cctgaccttc agcccctacc tgctgagcca cgtgatgggc tacggcttct      8760
accacttcgg cacctacccc agcggctacg agaacccctt cctgcacgcc atcaacaacg      8820
gcggctacac caacgcccgc atcgagaagt acgaggacgg cggcgtgctg cacgtgagct      8880

tcagctaccg ctacgaggcc ggccgcgtga tcggcgactt caaggtgatg ggcaccggct      8940

tccccgagga cagcgtgatc ttcaccgaca aatcatccg cagcaacgcc accgtggagc      9000
acctgcaccc catgggcgat aacgatctgg atggcagcttcacccgcacc ttcagcctgc      9060 gcgacgcgg ctactacagc tccgtggtgg acagccacat gcacttcaag agcgccatcc      9120
accccagcat cctgcagaac ggggccccca tgttcgccttccgccgcgtg gaggaggatc      9180
```

-continued

```
acagcaacac cgagctgggc atcgtggagt accagcacgc cttcaagacc ccggatgcag    9240
atgccggtga agaatatgaa gttcatcatc agagcagctc aagatcagac acattggacg    9300
ctggagagga gaaaagaaa aataaagaag tagccactgt gtccgatgga atgaaaaaga    9360
aggaggttga atcaacacgc gattctgatg tgaatgcggg aactgttgga acattcaccg    9420
ttccaagaat caaatcaatc actgaggaga tgcgtatgcc aaaacaaaag aaaaagggtg    9480
ttctcaactt ggctcattta cttgaataca aaccaagcca agtcgacata tcgaatactc    9540
gttcaaccca ggcacaattt gacaattggt ataatgaagt tatgaaagca tacgatctac    9600
aagaggaggc aatgggtaca gtgatgaatg gcttaatggt ttggtgcatt gaaaatggca    9660
cgtccccaaa tattagtgga acatggacca tgatggatgg agacgaacag gtggaattcc    9720
cattaaagcc cgtgatagag aatgctaagc cgacttttcg gcagataatg gcgcattttt    9780
ctgatgtggc tgaggcatat atagaaatgc gcaataagca agaaccatac atgccacgat    9840
atggtttggt tcgaaattta cgagacatgg gtctggctcg atacgcattt gacttctatg    9900
aagtcacatc gcgtacgtca acacgtgctc gcgaagccca tatccaaatg aaagcagcag    9960
cattgaaatc tgctcaaaca aggctatttg gattggatgg tggcatagga acacaaggag   10020
aaaacacaga gcgccatacc actgaagatg tgagccccga catgcatacc ctgcttgggg   10080
tcagaaatat gtgactgatg tggtctctgg gatgaaatat tattatatgt agtatgcaat   10140
atatagtatg gcttttctcg ttccagtctt tatattaatg agagtaactt aagtaagtaa   10200
tttgtacttc aaggattaat caaggtgact ctttgacact ctcagtgagg tgacttgttt   10260
agtctgagtt tacttatcgt gagtataaag aatctctcag aaaacgagag tgacttctag   10320
acacactcta ggaggtgacc gtagttggca tgagagagac aaaaaaaaaa aaaaa        10375
```

<210> SEQ ID NO 4
<211> LENGTH: 3308
<212> TYPE: PRT
<213> ORGANISM: Artificial Sequence
<220> FEATURE:
<223> OTHER INFORMATION: PoPMv-GFP

<400> SEQUENCE: 4

```
Met Ala Ile Asn Val Ile Gln Phe Gly Ser Phe Val Cys Asn Leu Pro
1               5                   10                  15

Lys Phe Gln Ser Ser Cys Thr Thr Met His Cys Pro Lys Gln Ser Ile
            20                  25                  30

Ser Thr Asn Val Val His Pro Ser Asn Pro Phe Ala Glu Leu Glu Glu
        35                  40                  45

Arg Leu Glu Pro Tyr Leu Gln Arg Arg Met Asp Ala Thr Ile Arg Leu
    50                  55                  60

Thr Arg Gly Gly Thr Leu Val Tyr Lys His Met Ser Glu Ala Lys Arg
65                  70                  75                  80

Ala Lys Lys Leu Arg Lys Gln Arg Glu Glu Glu Val His Leu
                85                  90                  95

Phe Met Asn Ala Ala Pro Tyr Ile Val Ser Asn Ile Thr Ile Gly Gly
                100                 105                 110

Gly Val Ala Pro Ser Lys Met Glu Glu Val Ser Ile Lys Arg Pro Leu
            115                 120                 125

Asn Lys Thr Pro Ser Gln Lys Ala Lys Lys Ser Phe Thr Pro Val Thr
        130                 135                 140

Phe Arg Asp Gly His Met Glu Lys Phe Leu Arg Gly Leu Lys Asn Cys
145                 150                 155                 160
```

```
Ala Thr Arg Asn Asn Met Thr Val His Leu Ile Gly Lys Arg Lys Thr
            165                 170                 175

Glu Leu Ala Phe Lys Arg Arg Ala Ser Ser Asp Ala Val Tyr Ala Thr
            180                 185                 190

Leu His His Met Arg Gly Val Asp Arg Lys Arg Asp Ile Val Leu Glu
            195                 200                 205

Glu Trp Met Asn Glu Tyr Val His Asn Leu Ser Arg Val Gly Thr Trp
            210                 215                 220

Gly Ser Leu Phe His Ala Glu Ser Leu Lys Arg Gly Asp Ser Gly Leu
225                 230                 235                 240

Ile Leu Asn Ala Arg Ala Leu Arg Gly Lys Phe Gly Arg Cys Ser Arg
            245                 250                 255

Gly Phe Phe Ile Val Arg Gly Lys Ser Asp Gly Ile Val Leu Asp Ala
            260                 265                 270

Arg Ser Lys Leu Ser Met Ala Thr Val Leu His Met Glu Gln Tyr Ser
            275                 280                 285

Thr Ser Glu Ala Phe Trp Ser Gly Leu Glu Lys Lys Trp Ser Val Met
            290                 295                 300

Arg Lys Pro Thr Ala His Thr Cys Lys Pro Thr Tyr Ser Val Ser Asn
305                 310                 315                 320

Cys Gly Glu Val Ala Ala Ile Ile Ala Gln Ala Leu Phe Pro Cys His
            325                 330                 335

Lys Leu Thr Cys Gly Glu Cys Ser Lys Glu Ile Cys Asp Leu Thr Ser
            340                 345                 350

Ser Glu Cys Val Gln Glu Leu Tyr Lys Asn Ile Ser Leu Ala Leu Glu
            355                 360                 365

Arg Met Asn Asn Leu His Pro Glu Phe Gln His Ile Val Lys Val Leu
            370                 375                 380

Ser Val Val Arg Gln Leu Thr Glu Ala Ser Asn His Gly Met Glu Val
385                 390                 395                 400

Phe Asp Glu Ile Phe Lys Met Ile Gly Ser Lys Thr Gln Ser Pro Phe
            405                 410                 415

Thr His Leu Asn Lys Leu Asn Glu Phe Met Leu Lys Gly Asn Glu Asn
            420                 425                 430

Thr Ser Glu Glu Trp Leu Thr Ala Arg Gln Arg Leu Lys Glu Leu Val
            435                 440                 445

Arg Phe Gln Lys Asn Arg Thr Asp Asn Ile Lys Lys Gly Asp Leu Ala
450                 455                 460

Ser Phe Arg Asn Lys Leu Ser Ala Arg Ala Gln Tyr Asn Leu Tyr Leu
465                 470                 475                 480

Ser Cys Asp Asn Gln Leu Asp Lys Asn Ala Ser Phe Leu Trp Gly Gln
            485                 490                 495

Arg Glu Tyr His Ala Arg Arg Phe Phe Leu Asn Phe Gln Gln Ile
            500                 505                 510

Asp Pro Ser Lys Gly Tyr Leu Ser Tyr Glu Asp Arg Thr Ile Pro Asn
            515                 520                 525

Gly Ser Arg Lys Leu Ala Ile Gly Asn Leu Ile Val Pro Leu Asp Leu
            530                 535                 540

Ala Glu Phe Arg Lys Arg Met Lys Gly Ile Asp Thr Gln Gln Pro Pro
545                 550                 555                 560

Ile Gly Lys Tyr Cys Thr Ser Gln Leu Asp Gly Asn Phe Val Tyr Pro
            565                 570                 575

Cys Cys Cys Thr Thr Leu Asp Asp Gly Gln Pro Ile Arg Ser Ala Val
            580                 585                 590
```

```
Tyr Ala Pro Thr Lys Lys His Leu Val Val Gly Asn Thr Gly Asp Thr
            595                 600                 605
Lys Tyr Ile Asn Leu Pro Lys Gly Asp Thr Glu Met Leu Tyr Ile Ala
            610                 615                 620
Leu Asp Gly Tyr Cys Tyr Ile Asn Ile Tyr Leu Ala Met Leu Val Asn
625                 630                 635                 640
Ile Ser Glu Glu Glu Ala Lys Asp Phe Thr Lys Lys Val Arg Asp Ile
                645                 650                 655
Phe Met Pro Lys Leu Gly Lys Trp Pro Thr Leu Met Asp Leu Ala Thr
            660                 665                 670
Thr Cys Ala Gln Leu Arg Ile Phe His Pro Asp Val His Asp Ala Glu
            675                 680                 685
Leu Pro Arg Ile Leu Val Asp His Asn Thr Gln Thr Cys His Val Val
            690                 695                 700
Asp Ser Tyr Gly Ser Ile Ser Thr Gly Tyr His Ile Leu Lys Ala Ala
705                 710                 715                 720
Thr Val Ser Gln Leu Val Leu Phe Ala Asp Asp Asn Leu Glu Ser Glu
                725                 730                 735
Ile Lys His Tyr Arg Val Gly Gly Thr Val Glu Asn His Lys Val Lys
            740                 745                 750
Ile Asp Asp Gln Pro Gly Arg Cys Gly Val Ser Glu Phe His Ala Ile
            755                 760                 765
Arg Met Leu Ile Lys Gly Ile Tyr Arg Pro Ser Val Met Tyr Glu Leu
            770                 775                 780
Leu Ser Glu Glu Pro Tyr Leu Leu Val Phe Ser Ile Leu Ser Pro Ser
785                 790                 795                 800
Ile Leu Ile Ala Met Tyr Asn Asp Arg Ala Phe Glu Leu Ala Val Gln
                805                 810                 815
Ile Trp Leu Glu Lys Glu Gln Ser Ile Pro Leu Ile Ala Thr Ile Leu
            820                 825                 830
Thr Asn Leu Ala Ala Lys Val Ser Val Ala Thr Thr Leu Val Gln Gln
            835                 840                 845
Leu Gln Leu Ile Glu Leu Ser Ala Asp Gln Leu Leu Asn Val Thr Cys
            850                 855                 860
Asp Gly Phe Arg Val Ser Phe Ala Tyr Gln Ser Ala Leu Thr Leu Leu
865                 870                 875                 880
Thr Arg Met Arg Asp Gln Ala Lys Ala Asn Ser Glu Leu Ile Ser Gly
                885                 890                 895
Gly Phe Asn Glu Tyr Asp Gln Asp Leu Ala Trp Thr Leu Glu Lys Asn
            900                 905                 910
Tyr Gln Gly Leu Leu His Asp Gln Trp Lys Glu Leu Ser Ser Leu Glu
            915                 920                 925
Lys Phe Arg Tyr Tyr Trp Ser Ser Arg Lys Thr Arg Leu Arg
            930                 935                 940
Ser Asn Ile Lys Ser Arg Ser Ser Pro Val Ala Ser Ala Ile Ser Ser
945                 950                 955                 960
Leu Ser Pro Lys Pro Phe Met Gly Lys Val Phe Ser His Met Lys Ala
                965                 970                 975
Gly Ala Val Arg Thr Lys Arg Gly Thr Lys Ser Phe Ile Asp Ala Arg
            980                 985                 990
Cys Leu Gly Ile Ser Thr Tyr Phe  Val Gly Ser Leu Met Arg Lys Phe
            995                 1000                1005
Pro Ser  Ala Lys Val Leu Leu  Ser Ser Leu Phe Val  Leu Gly Ala
```

-continued

```
                1010                1015                1020

Leu Leu Asn Ile Thr Arg Ala Ala Asn Arg Ile Ile Ile Asp Asn
    1025                1030                1035

Arg Ile Ser Arg Glu His Ala Ala Ala Leu Glu Leu Tyr Arg Lys
    1040                1045                1050

Glu Asp Thr Cys His Glu Leu Tyr Thr Ala Leu Glu Arg Lys Leu
    1055                1060                1065

Gly Glu Lys Pro Thr Trp Asp Glu Tyr Cys Ser Tyr Val Ala Lys
    1070                1075                1080

Ile Asn Pro Ala Thr Leu Glu Phe Ile Lys Asp Ser Tyr Asp Glu
    1085                1090                1095

Lys Gln Val Ile His Gln Arg Ser Thr Glu Asp Leu Lys Lys Val
    1100                1105                1110

Glu His Ile Ile Ala Phe Val Thr Leu Ala Ile Met Leu Phe Asp
    1115                1120                1125

Ser Glu Arg Ser Asp Cys Val Phe Lys Thr Leu Asn Lys Phe Lys
    1130                1135                1140

Gly Val Val Cys Ser Leu Gly Ser Glu Val Arg His Gln Ser Leu
    1145                1150                1155

Asp Asp Phe Val Asn Thr Met Asp Glu Lys Asn Phe Val Val Asp
    1160                1165                1170

Phe Glu Leu Asn Asp Ser Val Gln Arg Lys Asn Leu Thr Thr Glu
    1175                1180                1185

Ile Thr Phe Glu Asn Trp Trp Asp Glu Gln Val Ala Arg Gly Phe
    1190                1195                1200

Thr Ile Pro His Tyr Arg Thr Glu Gly Arg Phe Met Glu Phe Thr
    1205                1210                1215

Arg Ala Thr Ala Ala Lys Val Ala Ser Asp Ile Ser Ile Ser Ser
    1220                1225                1230

Glu Arg Asp Phe Leu Ile Arg Gly Ala Val Gly Ser Gly Lys Ser
    1235                1240                1245

Thr Gly Leu Pro His His Leu Ser Thr Tyr Gly Arg Val Leu Leu
    1250                1255                1260

Ile Glu Pro Thr Arg Pro Leu Ala Glu Asn Val Phe Lys Gln Leu
    1265                1270                1275

Ser Gly Gly Pro Phe Phe Leu Lys Pro Thr Met Arg Met Arg Gly
    1280                1285                1290

Asn Ser Val Phe Gly Ser Ser Pro Ile Ser Val Met Thr Ser Gly
    1295                1300                1305

Phe Ala Leu His Phe Phe Ala Asn Asn Ile Thr Gln Leu Gln Glu
    1310                1315                1320

Ile Gln Phe Ile Ile Ile Asp Glu Cys His Val Met Asp Ala Ser
    1325                1330                1335

Ser Met Ala Phe Arg Ser Leu Ile His Thr Tyr His Thr Asn Cys
    1340                1345                1350

Lys Val Leu Lys Val Ser Ala Thr Pro Pro Gly Arg Glu Val Glu
    1355                1360                1365

Phe Thr Thr Gln Phe Pro Val Lys Leu Val Val Glu Asp Ser Leu
    1370                1375                1380

Ser Phe Lys Thr Phe Val Glu Ser Gln Gly Thr Gly Ser Asn Cys
    1385                1390                1395

Asp Met Ile Gln Tyr Gly Asn Asn Leu Leu Val Tyr Val Ala Ser
    1400                1405                1410
```

```
Tyr Asn Glu Val Asp Gln Leu Ser Lys Leu Leu Val Ala Arg Glu
1415                1420                1425

Phe Asn Val Thr Lys Val Asp Gly Arg Thr Met Lys His Gly Glu
1430                1435                1440

Leu Glu Ile Val Thr Arg Gly Thr Lys Ser Lys Pro His Phe Val
1445                1450                1455

Val Ala Thr Asn Ile Ile Glu Asn Gly Val Thr Leu Asp Ile Asp
1460                1465                1470

Val Val Ile Asp Phe Gly Met Lys Val Ser Pro Phe Leu Asp Val
1475                1480                1485

Asp Asn Arg Ser Val Ala Tyr Asn Lys Val Ser Ile Ser Tyr Gly
1490                1495                1500

Glu Arg Ile Gln Arg Leu Gly Arg Val Gly Arg Ile Gln Lys Gly
1505                1510                1515

Thr Ala Leu Arg Ile Gly His Thr Glu Lys Gly Leu Ile Glu Ile
1520                1525                1530

Pro Gln Met Ile Ser Thr Glu Ala Ala Leu Tyr Cys Phe Ala Tyr
1535                1540                1545

Asn Leu Pro Val Met Ser Ser Gly Val Ser Thr Ser Met Ile Lys
1550                1555                1560

Asn Cys Thr Ile Pro Gln Val Arg Thr Met His Thr Phe Glu Leu
1565                1570                1575

Ser Pro Phe Phe Met Tyr Asn Phe Val Ser His Asp Gly Thr Met
1580                1585                1590

His Pro Val Val His Glu Ile Leu Lys Arg Tyr Lys Leu Arg Asp
1595                1600                1605

Ser Val Ile Pro Leu Ser Glu Ser Ser Ile Pro Tyr Arg Ala Ser
1610                1615                1620

Ser Asp Trp Ile Thr Ala Gly Asp Tyr Arg Arg Ile Gly Val Lys
1625                1630                1635

Leu Asp Ile Pro Asp Glu Thr Arg Ile Ala Phe His Ile Lys Asp
1640                1645                1650

Ile Pro Pro Gln Ile His Gln Leu Trp Glu Ser Val Leu Lys
1655                1660                1665

Tyr Lys Ala Ser Ala Ala Phe Pro Thr Leu Arg Ser Ser Ser Ile
1670                1675                1680

Thr Lys Ile Ala Tyr Thr Leu Ser Thr Asp Leu Tyr Ala Ile Pro
1685                1690                1695

Arg Thr Leu Ala Val Val Glu Ser Leu Leu Glu Asp Glu Arg Thr
1700                1705                1710

Lys Gln Tyr Gln Phe Lys Ser Leu Ile Asp Asn Gly Cys Ser Ser
1715                1720                1725

Met Phe Ser Val Val Gly Ile Ser Asn Ala Leu Arg Ala Lys Tyr
1730                1735                1740

Ser Lys Asp Tyr Thr Val Glu Asn Ile Asn Lys Leu Glu Ala Val
1745                1750                1755

Lys Ala Gln Leu Lys Glu Phe His Asn Leu Asn Gly Ser Gly Asp
1760                1765                1770

Glu Leu Asn Leu Ile Lys Arg Phe Glu Ser Leu Gln Phe Val His
1775                1780                1785

His Gln Ser Lys Ser Ser Leu Ala Lys Ala Leu Gly Leu Arg Gly
1790                1795                1800

Val Trp Asn Lys Ser Leu Ile Val Arg Asp Ala Ile Ile Ala Ala
1805                1810                1815
```

-continued

```
Gly Val Ala Cys Gly Gly Ala Trp Leu Leu Tyr Thr Trp Phe Thr
    1820            1825                1830

Gly Lys Met Ser Glu Val Ser His Gln Gly Arg Ser Lys Thr Lys
    1835            1840                1845

Arg Ile Gln Ala Leu Lys Phe Arg Lys Ala Arg Asp Lys Arg Ala
    1850            1855                1860

Gly Phe Glu Ile Asp Asn Asn Glu Asp Thr Ile Glu Glu Tyr Phe
    1865            1870                1875

Gly Ser Ala Tyr Thr Lys Lys Gly Lys Gly Lys Gly Thr Thr Val
    1880            1885                1890

Gly Met Gly Lys Thr Asn Arg Arg Phe Ile Asn Met Tyr Gly Phe
    1895            1900                1905

Glu Pro Gly Gln Phe Ser Tyr Ile Lys Phe Val Asp Pro Leu Thr
    1910            1915                1920

Gly Ala Gln Met Glu Glu Asn Val Tyr Ala Asp Ile Val Asp Val
    1925            1930                1935

Gln Asp Lys Phe Gly Glu Ile Arg Arg Gln Met Ile Ile Asp Asp
    1940            1945                1950

Glu Leu Asp Asn Arg Gln Thr Glu Val His Asn Thr Ile His Ala
    1955            1960                1965

Tyr Leu Ile Lys Asp Trp Ser Asn Lys Ala Leu Lys Val Asp Leu
    1970            1975                1980

Thr Pro His Asn Pro Leu Arg Val Ser Asp Lys Ala Ser Ala Ile
    1985            1990                1995

Met Lys Phe Pro Glu Arg Glu Gly Glu Leu Arg Gln Thr Gly Gln
    2000            2005                2010

Ala Val Glu Val Asp Val Ser Asp Ile Pro Lys Glu Val Val Lys
    2015            2020                2025

His Glu Ala Lys Thr Leu Met Arg Gly Leu Arg Asp Tyr Asn Pro
    2030            2035                2040

Ile Ala Gln Thr Val Cys Lys Leu Thr Val Lys Ser Glu Leu Gly
    2045            2050                2055

Glu Thr Ser Thr Tyr Gly Leu Gly Phe Gly Gly Leu Ile Ile Ala
    2060            2065                2070

Asn His His Leu Phe Lys Ser Phe Asn Gly Ser Leu Glu Val Lys
    2075            2080                2085

Ser His His Gly Val Phe Arg Val Pro Asn Leu Met Ala Ile Ser
    2090            2095                2100

Val Leu Pro Leu Lys Gly Arg Asp Met Ile Ile Ile Lys Met Pro
    2105            2110                2115

Lys Asp Phe Pro Val Phe Pro Gln Arg Leu Lys Phe Arg Glu Pro
    2120            2125                2130

Ala Ser Thr Asp Arg Val Cys Leu Ile Gly Ser Asn Phe Gln Glu
    2135            2140                2145

Arg Tyr Ile Ser Thr Thr Val Ser Glu Thr Ser Ala Thr His Pro
    2150            2155                2160

Val Pro Arg Ser Thr Phe Trp Lys His Trp Ile Ser Thr Asp Asp
    2165            2170                2175

Gly His Cys Gly Leu Pro Ile Val Ser Thr Thr Asp Gly Phe Ile
    2180            2185                2190

Leu Gly Leu His Ser Leu Ala Asn Asn Arg Asn Ser Glu Asn Tyr
    2195            2200                2205

Tyr Thr Ala Phe Asp Ser Asp Phe Glu Met Lys Ile Leu Arg Ser
```

```
                2210                2215                2220

Gly Glu Asn Thr Glu Trp Val Lys Asn Trp Lys Tyr Asn Pro Asp
        2225                2230                2235

Thr Val Leu Trp Gly Pro Leu Gln Leu Thr Lys Gly Thr Pro Ser
        2240                2245                2250

Gly Met Phe Lys Thr Thr Lys Met Ile Glu Asp Leu Leu Ala Phe
        2255                2260                2265

Lys Ser Glu Cys Val Arg Glu Gln Ala His Thr Ser Pro Trp Met
        2270                2275                2280

Leu Glu Val Leu Lys Glu Asn Leu Lys Ala Val Ala Tyr Met Lys
        2285                2290                2295

Ser Gln Leu Val Thr Lys His Val Val Lys Gly Glu Cys Thr Met
        2300                2305                2310

Phe Lys Gln Tyr Leu Gln Glu Asn Ser Arg Ala Asn Glu Phe Phe
        2315                2320                2325

Gln Pro Lys Met Trp Ala Tyr Gly Lys Ser Met Leu Asn Lys Glu
        2330                2335                2340

Ala Tyr Ile Lys Asp Ile Met Lys Tyr Ser Lys Val Ile Asp Val
        2345                2350                2355

Gly Val Val Asp Cys Asp Ala Phe Glu Glu Ala Ile Ile Arg Val
        2360                2365                2370

Ile Val Tyr Met Gln Ile His Gly Phe Arg Lys Cys Ser Tyr Ile
        2375                2380                2385

Thr Asp Glu Glu Glu Ile Phe Lys Ala Leu Asn Met Asn Thr Ala
        2390                2395                2400

Val Gly Ala Met Tyr Gly Gly Lys Lys Lys Glu Tyr Phe Glu Lys
        2405                2410                2415

Phe Thr Thr Glu Asp Lys Ala Glu Ile Leu Arg Gln Ser Cys Leu
        2420                2425                2430

Arg Leu Tyr Thr Gly Lys Leu Gly Val Trp Asn Gly Ser Leu Lys
        2435                2440                2445

Ala Glu Leu Arg Ser Lys Glu Lys Ile Glu Ala Asn Lys Thr Arg
        2450                2455                2460

Thr Phe Thr Ala Ala Pro Ile Asp Thr Leu Leu Gly Gly Lys Val
        2465                2470                2475

Cys Val Asp Asp Phe Asn Asn Gln Phe Tyr Ser Lys Asn Ile Glu
        2480                2485                2490

Cys Cys Trp Thr Val Gly Met Thr Lys Phe Tyr Gly Gly Trp Asn
        2495                2500                2505

Lys Leu Leu Thr Ala Leu Pro Asp Gly Trp Ile Tyr Cys Asp Ala
        2510                2515                2520

Asp Gly Ser Gln Phe Asp Ser Ser Leu Thr Pro Tyr Leu Ile Asn
        2525                2530                2535

Ala Val Leu Thr Ile Arg Tyr Ala Phe Met Glu Asp Trp Asp Ile
        2540                2545                2550

Gly Tyr Lys Met Leu Gln Asn Leu Tyr Thr Glu Ile Ile Tyr Thr
        2555                2560                2565

Pro Ile Ser Thr Pro Asp Gly Thr Ile Val Lys Lys Phe Arg Gly
        2570                2575                2580

Asn Asn Ser Gly Gln Pro Ser Thr Val Val Asp Asn Ser Leu Met
        2585                2590                2595

Val Val Leu Ala Met His Tyr Ala Phe Val Arg Glu Gly Val Val
        2600                2605                2610
```

-continued

Phe Glu Glu Ile Asp Ser Ile Cys Lys Phe Val Asn Gly Asp
2615                2620                2625

Asp Leu Leu Ile Ala Val Asn Pro Gly Arg Glu Asn Leu Leu Asp
2630                2635                2640

Thr Leu Ser Ser His Phe Ser Asp Leu Gly Leu Asn Tyr Asp Phe
2645                2650                2655

Ser Ser Arg Thr Arg Asp Lys Ser Glu Leu Trp Phe Met Ser His
2660                2665                2670

Cys Gly Ile Pro Val Glu Gly Met Tyr Ile Pro Lys Leu Glu Glu
2675                2680                2685

Glu Arg Ile Val Ser Ile Leu Gln Trp Asp Arg Ala Glu Leu Pro
2690                2695                2700

Glu Tyr Arg Leu Glu Ala Ile Cys Ala Ala Met Ile Glu Ser Trp
2705                2710                2715

Gly Tyr Pro Gln Leu Thr His Glu Ile Arg Arg Phe Tyr Ser Trp
2720                2725                2730

Leu Ile Glu Lys Asn Pro Tyr Ala Asp Leu Ala Ser Glu Gly Lys
2735                2740                2745

Ala Pro Tyr Ile Ser Glu Leu Ala Leu Lys Lys Leu Tyr Leu Asn
2750                2755                2760

Gln Asp Val Gln Asn Asp Glu Leu Gln Val Tyr Leu Arg Tyr Phe
2765                2770                2775

Ala Glu Ala Asp Glu Glu Phe Glu Cys Gly Thr Tyr Glu Val His
2780                2785                2790

His Gln Ser Ser Met Glu Ser Asp Glu Ser Gly Leu Pro Ala Met
2795                2800                2805

Glu Ile Glu Cys Arg Ile Thr Gly Thr Leu Asn Gly Val Glu Phe
2810                2815                2820

Glu Leu Val Gly Gly Gly Glu Gly Thr Pro Glu Gln Gly Arg Met
2825                2830                2835

Thr Asn Lys Met Lys Ser Thr Lys Gly Ala Leu Thr Phe Ser Pro
2840                2845                2850

Tyr Leu Leu Ser His Val Met Gly Tyr Gly Phe Tyr His Phe Gly
2855                2860                2865

Thr Tyr Pro Ser Gly Tyr Glu Asn Pro Phe Leu His Ala Ile Asn
2870                2875                2880

Asn Gly Gly Tyr Thr Asn Ala Arg Ile Glu Lys Tyr Glu Asp Gly
2885                2890                2895

Gly Val Leu His Val Ser Phe Ser Tyr Arg Tyr Glu Ala Gly Arg
2900                2905                2910

Val Ile Gly Asp Phe Lys Val Met Gly Thr Gly Phe Pro Glu Asp
2915                2920                2925

Ser Val Ile Phe Thr Asp Lys Ile Ile Arg Ser Asn Ala Thr Val
2930                2935                2940

Glu His Leu His Pro Met Gly Asp Asn Asp Leu Asp Gly Ser Phe
2945                2950                2955

Thr Arg Thr Phe Ser Leu Arg Asp Gly Gly Tyr Tyr Ser Ser Val
2960                2965                2970

Val Asp Ser His Met His Phe Lys Ser Ala Ile His Pro Ser Ile
2975                2980                2985

Leu Gln Asn Gly Gly Pro Met Phe Ala Phe Arg Arg Val Glu Glu
2990                2995                3000

Asp His Ser Asn Thr Glu Leu Gly Ile Val Glu Tyr Gln His Ala
3005                3010                3015

```
Phe Lys Thr Pro Asp Ala Asp Ala Gly Glu Glu Tyr Glu Val His
    3020              3025                3030

His Gln Ser Ser Ser Arg Ser Asp Thr Leu Asp Ala Gly Glu Glu
    3035              3040                3045

Lys Lys Lys Asn Lys Glu Val Ala Thr Val Ser Asp Gly Met Lys
    3050              3055                3060

Lys Lys Glu Val Glu Ser Thr Arg Asp Ser Asp Val Asn Ala Gly
    3065              3070                3075

Thr Val Gly Thr Phe Thr Val Pro Arg Ile Lys Ser Ile Thr Glu
    3080              3085                3090

Glu Met Arg Met Pro Lys Gln Lys Lys Lys Gly Val Leu Asn Leu
    3095              3100                3105

Ala His Leu Leu Glu Tyr Lys Pro Ser Gln Val Asp Ile Ser Asn
    3110              3115                3120

Thr Arg Ser Thr Gln Ala Gln Phe Asp Asn Trp Tyr Asn Glu Val
    3125              3130                3135

Met Lys Ala Tyr Asp Leu Gln Glu Ala Met Gly Thr Val Met
    3140              3145                3150

Asn Gly Leu Met Val Trp Cys Ile Glu Asn Gly Thr Ser Pro Asn
    3155              3160                3165

Ile Ser Gly Thr Trp Thr Met Met Asp Gly Asp Glu Gln Val Glu
    3170              3175                3180

Phe Pro Leu Lys Pro Val Ile Glu Asn Ala Lys Pro Thr Phe Arg
    3185              3190                3195

Gln Ile Met Ala His Phe Ser Asp Val Ala Glu Ala Tyr Ile Glu
    3200              3205                3210

Met Arg Asn Lys Gln Glu Pro Tyr Met Pro Arg Tyr Gly Leu Val
    3215              3220                3225

Arg Asn Leu Arg Asp Met Gly Leu Ala Arg Tyr Ala Phe Asp Phe
    3230              3235                3240

Tyr Glu Val Thr Ser Arg Thr Ser Thr Arg Ala Arg Glu Ala His
    3245              3250                3255

Ile Gln Met Lys Ala Ala Ala Leu Lys Ser Ala Gln Thr Arg Leu
    3260              3265                3270

Phe Gly Leu Asp Gly Gly Ile Gly Thr Gln Gly Glu Asn Thr Glu
    3275              3280                3285

Arg His Thr Thr Glu Asp Val Ser Pro Asp Met His Thr Leu Leu
    3290              3295                3300

Gly Val Arg Asn Met
    3305

<210> SEQ ID NO 5
<211> LENGTH: 20
<212> TYPE: DNA
<213> ORGANISM: Bacteriophage SP6

<400> SEQUENCE: 5
atttaggtga cactatagaa                                              20

<210> SEQ ID NO 6
<211> LENGTH: 49
<212> TYPE: DNA
<213> ORGANISM: Artificial Sequence
<220> FEATURE:
<223> OTHER INFORMATION: KpnI-SP6 5' primer

<400> SEQUENCE: 6
```

```
gagaggtacc atttaggtga cactatagaa attaaaacat aacatacaa        49
```

<210> SEQ ID NO 7
<211> LENGTH: 18
<212> TYPE: DNA
<213> ORGANISM: Artificial Sequence
<220> FEATURE:
<223> OTHER INFORMATION: BamHI 3' primer

<400> SEQUENCE: 7

```
cccttaaatg ttgtcgag                                          18
```

<210> SEQ ID NO 8
<211> LENGTH: 18
<212> TYPE: DNA
<213> ORGANISM: Artificial Sequence
<220> FEATURE:
<223> OTHER INFORMATION: BamHI 5' primer

<400> SEQUENCE: 8

```
cttcaaaatg attggatc                                          18
```

<210> SEQ ID NO 9
<211> LENGTH: 18
<212> TYPE: DNA
<213> ORGANISM: Artificial Sequence
<220> FEATURE:
<223> OTHER INFORMATION: PacI 3' primer

<400> SEQUENCE: 9

```
atcgagggtg agagaatg                                          18
```

<210> SEQ ID NO 10
<211> LENGTH: 18
<212> TYPE: DNA
<213> ORGANISM: Artificial Sequence
<220> FEATURE:
<223> OTHER INFORMATION: PacI 5' primer

<400> SEQUENCE: 10

```
agtgagcgag tttcatgc                                          18
```

<210> SEQ ID NO 11
<211> LENGTH: 18
<212> TYPE: DNA
<213> ORGANISM: Artificial Sequence
<220> FEATURE:
<223> OTHER INFORMATION: BglII 3' primer

<400> SEQUENCE: 11

```
agtgagcaca caacaccc                                          18
```

<210> SEQ ID NO 12
<211> LENGTH: 18
<212> TYPE: DNA
<213> ORGANISM: Artificial Sequence
<220> FEATURE:
<223> OTHER INFORMATION: BglII 5' primer

<400> SEQUENCE: 12

```
aactgaagat ctcaagaa                                          18
```

<210> SEQ ID NO 13
<211> LENGTH: 21
<212> TYPE: DNA
<213> ORGANISM: Artificial Sequence
<220> FEATURE:
<223> OTHER INFORMATION: SpeI 3' primer

<400> SEQUENCE: 13
ccacctggca gagaggtgga g                                           21

<210> SEQ ID NO 14
<211> LENGTH: 22
<212> TYPE: DNA
<213> ORGANISM: Artificial Sequence
<220> FEATURE:
<223> OTHER INFORMATION: SpeI 5' primer

<400> SEQUENCE: 14
ggcttactct ttgttcctcg tg                                          22

<210> SEQ ID NO 15
<211> LENGTH: 18
<212> TYPE: DNA
<213> ORGANISM: Artificial Sequence
<220> FEATURE:
<223> OTHER INFORMATION: ClaI 3' primer

<400> SEQUENCE: 15
tagctctgag tgcatttg                                               18

<210> SEQ ID NO 16
<211> LENGTH: 18
<212> TYPE: DNA
<213> ORGANISM: Artificial Sequence
<220> FEATURE:
<223> OTHER INFORMATION: ClaI 5' primer

<400> SEQUENCE: 16
ttgcgatcat catcgatt                                               18

<210> SEQ ID NO 17
<211> LENGTH: 18
<212> TYPE: DNA
<213> ORGANISM: Artificial Sequence
<220> FEATURE:
<223> OTHER INFORMATION: NcoI 3' primer

<400> SEQUENCE: 17
ctcaaacagc tttgccgg                                               18

<210> SEQ ID NO 18
<211> LENGTH: 18
<212> TYPE: DNA
<213> ORGANISM: Artificial Sequence
<220> FEATURE:
<223> OTHER INFORMATION: NcoI 5' primer

<400> SEQUENCE: 18
catgcagatc catggctt                                               18

<210> SEQ ID NO 19
<211> LENGTH: 18
<212> TYPE: DNA
<213> ORGANISM: Artificial Sequence
<220> FEATURE:
<223> OTHER INFORMATION: SalI 3' primer

<400> SEQUENCE: 19
aatatttggg gacgtgcc                                               18

```
<210> SEQ ID NO 20
<211> LENGTH: 18
<212> TYPE: DNA
<213> ORGANISM: Artificial Sequence
<220> FEATURE:
<223> OTHER INFORMATION: SalI 5' primer

<400> SEQUENCE: 20
cttgaataca aaccaagc                                                 18

<210> SEQ ID NO 21
<211> LENGTH: 55
<212> TYPE: DNA
<213> ORGANISM: Artificial Sequence
<220> FEATURE:
<223> OTHER INFORMATION: polyA-KpnI 3' primer

<400> SEQUENCE: 21
ggggtacctt tttttttttt tttttttttt tttttttttgt ctctctcatg ccaac       55

<210> SEQ ID NO 22
<211> LENGTH: 36
<212> TYPE: DNA
<213> ORGANISM: Artificial Sequence
<220> FEATURE:
<223> OTHER INFORMATION: NIbGFP3' primer

<400> SEQUENCE: 22
ctcgtcgctc tccatgctgc tctgatgatg aacttc                             36

<210> SEQ ID NO 23
<211> LENGTH: 35
<212> TYPE: DNA
<213> ORGANISM: Artificial Sequence
<220> FEATURE:
<223> OTHER INFORMATION: NIbGFP5' primer

<400> SEQUENCE: 23
gttcatcaga gcagcatgga gagcgacgag agcgg                              35

<210> SEQ ID NO 24
<211> LENGTH: 37
<212> TYPE: DNA
<213> ORGANISM: Artificial Sequence
<220> FEATURE:
<223> OTHER INFORMATION: CPGFP3' primer

<400> SEQUENCE: 24
gatgaacttc atattcttca ccggcatctg catcccg                            37

<210> SEQ ID NO 25
<211> LENGTH: 38
<212> TYPE: DNA
<213> ORGANISM: Artificial Sequence
<220> FEATURE:
<223> OTHER INFORMATION: GFPCP5' primer

<400> SEQUENCE: 25
gatgccggtg aagaatatga agttcatcat cagagcag                           38

<210> SEQ ID NO 26
<211> LENGTH: 46
<212> TYPE: DNA
<213> ORGANISM: Artificial Sequence
<220> FEATURE:
<223> OTHER INFORMATION: polyA-SacII3' primer

<400> SEQUENCE: 26
```

```
gagaccgcgg tttttttttt ttttgtctc tctcatgcca actacg          46
```

<210> SEQ ID NO 27
<211> LENGTH: 18
<212> TYPE: DNA
<213> ORGANISM: Artificial Sequence
<220> FEATURE:
<223> OTHER INFORMATION: TurboGFP5' primer

<400> SEQUENCE: 27

```
atggagagcg acgagagc                                        18
```

<210> SEQ ID NO 28
<211> LENGTH: 18
<212> TYPE: DNA
<213> ORGANISM: Artificial Sequence
<220> FEATURE:
<223> OTHER INFORMATION: TurboGFP3' primer

<400> SEQUENCE: 28

```
ttcttcaccg gcatctgc                                        18
```

<210> SEQ ID NO 29
<211> LENGTH: 19
<212> TYPE: DNA
<213> ORGANISM: Artificial Sequence
<220> FEATURE:
<223> OTHER INFORMATION: PepMoV-CP5' primer

<400> SEQUENCE: 29

```
agcgctcaag ctcagacac                                       19
```

<210> SEQ ID NO 30
<211> LENGTH: 21
<212> TYPE: DNA
<213> ORGANISM: Artificial Sequence
<220> FEATURE:
<223> OTHER INFORMATION: PepMoV-CP3' primer

<400> SEQUENCE: 30

```
catatttctg accccaagca g                                    21
```

<210> SEQ ID NO 31
<211> LENGTH: 23
<212> TYPE: DNA
<213> ORGANISM: Artificial Sequence
<220> FEATURE:
<223> OTHER INFORMATION: PepMoV-VPg5' primer

<400> SEQUENCE: 31

```
gctctagagg acgctctaag acg                                  23
```

<210> SEQ ID NO 32
<211> LENGTH: 23
<212> TYPE: DNA
<213> ORGANISM: Artificial Sequence
<220> FEATURE:
<223> OTHER INFORMATION: PepMoV-VPg3' primer

<400> SEQUENCE: 32

```
ggggtacctt cgtgcttcac aac                                  23
```

<210> SEQ ID NO 33
<211> LENGTH: 46
<212> TYPE: DNA
<213> ORGANISM: Artificial Sequence

```
<220> FEATURE:
<223> OTHER INFORMATION: NAT5' primer

<400> SEQUENCE: 33
gagcagctca agatcagaca cattggacgc tgaagaggag aaaaag           46

<210> SEQ ID NO 34
<211> LENGTH: 50
<212> TYPE: DNA
<213> ORGANISM: Artificial Sequence
<220> FEATURE:
<223> OTHER INFORMATION: NAT3' primer

<400> SEQUENCE: 34
gtggctactt ctttattttt cttttctcc tcttcagcgt ccaatgtgtc         50

<210> SEQ ID NO 35
<211> LENGTH: 5
<212> TYPE: PRT
<213> ORGANISM: Artificial Sequence
<220> FEATURE:
<223> OTHER INFORMATION: FIVRG motif

<400> SEQUENCE: 35

Phe Ile Val Arg Gly
1               5

<210> SEQ ID NO 36
<211> LENGTH: 5
<212> TYPE: PRT
<213> ORGANISM: Artificial Sequence
<220> FEATURE:
<223> OTHER INFORMATION: CCCTT motif

<400> SEQUENCE: 36

Cys Cys Cys Thr Thr
1               5

<210> SEQ ID NO 37
<211> LENGTH: 5
<212> TYPE: PRT
<213> ORGANISM: Artificial Sequence
<220> FEATURE:
<223> OTHER INFORMATION: LAIGN motif

<400> SEQUENCE: 37

Leu Ala Ile Gly Asn
1               5

<210> SEQ ID NO 38
<211> LENGTH: 7
<212> TYPE: PRT
<213> ORGANISM: Artificial Sequence
<220> FEATURE:
<223> OTHER INFORMATION: VGSGKST motif

<400> SEQUENCE: 38

Val Gly Ser Gly Lys Ser Thr
1               5

<210> SEQ ID NO 39
<211> LENGTH: 4
<212> TYPE: PRT
<213> ORGANISM: Artificial Sequence
<220> FEATURE:
<223> OTHER INFORMATION: DECH motif

<400> SEQUENCE: 39
```

Asp Glu Cys His
1

<210> SEQ ID NO 40
<211> LENGTH: 6
<212> TYPE: PRT
<213> ORGANISM: Artificial Sequence
<220> FEATURE:
<223> OTHER INFORMATION: CDADGS motif

<400> SEQUENCE: 40

Cys Asp Ala Asp Gly Ser
1               5

<210> SEQ ID NO 41
<211> LENGTH: 44
<212> TYPE: PRT
<213> ORGANISM: Artificial Sequence
<220> FEATURE:
<223> OTHER INFORMATION: SGC35X3NTX30GDD motif

<400> SEQUENCE: 41

Ser Gly Gln Pro Ser Thr Val Val Asp Asn Ser Leu Met Val Val Leu
1               5                   10                  15

Ala Met His Tyr Ala Phe Val Arg Glu Gly Val Val Phe Glu Glu Ile
            20                  25                  30

Asp Ser Ile Cys Lys Phe Phe Val Asn Gly Asp Asp
        35                  40

<210> SEQ ID NO 42
<211> LENGTH: 4
<212> TYPE: PRT
<213> ORGANISM: Artificial Sequence
<220> FEATURE:
<223> OTHER INFORMATION: KLTC motif

<400> SEQUENCE: 42

Lys Leu Thr Cys
1

<210> SEQ ID NO 43
<211> LENGTH: 4
<212> TYPE: PRT
<213> ORGANISM: Artificial Sequence
<220> FEATURE:
<223> OTHER INFORMATION: FRNK motif

<400> SEQUENCE: 43

Phe Arg Asn Lys
1

<210> SEQ ID NO 44
<211> LENGTH: 45
<212> TYPE: PRT
<213> ORGANISM: Artificial Sequence
<220> FEATURE:
<223> OTHER INFORMATION: RX43D motif

<400> SEQUENCE: 44

Arg Gln Ile Met Ala His Phe Ser Asp Val Ala Glu Ala Tyr Ile Glu
1               5                   10                  15

Met Arg Asn Lys Gln Glu Pro Tyr Met Pro Arg Tyr Gly Leu Val Arg
            20                  25                  30

```
Asn Leu Arg Asp Met Gly Leu Ala Arg Tyr Ala Phe Asp
     35              40                  45
```

HIGHLY INFECTIOUS NUCLEIC ACID MOLECULES FROM PEPPER MOTTLE VIRUS AND PLANT VIRAL VECTOR DERIVED FROM THE SAME

CROSS-REFERENCE TO RELATED APPLICATIONS

This application is the U.S. national stage filing under 35 U.S.C. §371 of international application PCT/KR2008/005716, filed Sep. 26, 2008, which claims priority from Korean Patent Application 10-2007-0137270, filed Dec. 26, 2007.

BACKGROUND OF THE INVENTION

1. Field of the Invention

The present invention relates to a plant-infectious nucleic acid molecule from Pepper mottle virus, and a viral vector a transformed cell and a transgenic plant having it.

2. Background of Technique

Various aspects of virus pathogenicity have been studied using in vitro- or in vivo-transcribed infectious RNA derived from full-length cDNA clones. It is not known how virus proteins are expressed from full-length clones, since the vector sequences do not contain promoters expected to transcribe the virus RNA in bacterial cells. Fakhfakh and their colleagues suggested that viral RNA is transcribed from cryptic promoters and protein synthesis initiated at cryptic ribosomal binding sites present in the virus cDNA sequences (Fakhfakh et al., 1996).

However, manipulation and amplification of full-length clones may prove difficult due to instability or toxicity of some virus sequences in bacteria (Chen and Hruening, 1992; Boyer and Haenni, 1994; Fakhfakh et al., 1996). Expression of virus proteins in *E. coli* has been reported to have toxic effects on the host cells (Lama and Carrasco, 1992; Rodriguez and Shaw, 1991). The toxic effects from undesired protein expression can be relieved by cloning in *E. coli* strains that reduce the plasmid copy number (Greener, 1993) or using low copy number cloning vectors (Schweizer, 2008).

Among potyviruses, the in vitro synthesis of biologically active RNAs from full-length cDNA clone with bacterial phage promoters have been reported; Tobacco vein mottling virus (TVMV) (Domier et al., 1989; Nicolas et al., 1996), Plum pox virus (PPV) (Riechmann et al., 1990), Zucchini yellow mosaic virus (ZYMV) (Gal-On et al., 1991; Lin et al., 2002), Tobacco etch virus (TEV) (Dolja et al., 1992), Peanut stripe virus (PStV) (Flasinski et al., 1995), Pea seed-borne mosaic virus (PSbMV) (Johansen et al, 1996), Potato virus A (PVA) (Puurand et al., 1996), Papaya ringspot virus (PRSV) (Chiang and Yeh, 1997), Potato virus Y (PVY) (Jakab et al., 1997), Papaya ringspot virus (PRSV) (Chiang and Yeh, 1997), Turnip mosaic virus (TuMV) (Sanchez et al, 1998) and Johnsongrass mosaic virus (JGMV-Jg)(Kim et al., 2003) and so on.

Another system is based on the delivery of particles coated with cDNA or the plasmids directly introduced of a virus into the plant cell to induce infection. In vivo infectious transcripts, which are driven by a Cauliflower mosaic virus (CaMV) 35S promoter that can be transcribed by an endogenous host RNA polymerase, have been reported for PPV-NAT (Maiss et al., 1992), ZYMV (Gal-On et al., 1995), PVY-NTN (Fakhfakh et al., 1996), PSbMV (Johansen, 1996), Clover yellow vein virus (CIYVV) (Takahashi et al, 1997), PRSV (Chiang and Yeh, 1997), PVY-N605 (Jakab et al, 1997), TuMV (Sanchez et al., 1998), Lettuce mosaic virus (LMV) (Yang et al., 1998) and PSbMV-L1 (Olsen and Johansen, 2001). In vitro- or in vivo-transcribed infectious RNA derived from full-length cDNA clones are an important tool in the study of RNA viruses. These clones are possible to facilitated studies of non-destructive monitoring of virus infection without by tagging reporter genes, such as green fluorescence protein gene (GFP) or β-glucuronidase gene (GUS).

Among the potyviruses, TEV was first developed to express reporter gene (Dolja et al., 1992; Carrington et al., 1993). Later, many potyviruses such as PPV (Guo et al., 1998; Fernandez-Fernandez et al., 2001), LMV (German-Retana et al., 2000), CIYVV (Masuta et al., 2000), Wheat streak mosaic virus (WSMV) (Choi et al., 2000), Tobacco vein mottling virus vector (TVMV) (Dietrich and Maiss, 2003), ZYMV (Arazi et al., 2001; Hsu et al., 2004), PVA (Ivanov et al., 2003) and TuMV (Beauchemin et al., 2005) have been engineered into effective expression of reporter gene at different insertion site of virus genome.

Potyviral proteins are expressed by proteolytic processing of the large precursor polyprotein by three virus-encoded proteases, P1, HC-pro and NIa. P1 and HC-pro automatically cleave at their respective C termini, and NIa cleave the remains (Uyeda, 1997). Most of the foreign ORFs are constructed adjacent to the junction between P1 and HC-Pro or NIb and CP by directional insertion. A plant virus-based vector is a useful tool for efficient expression of target foreign proteins in plants. Plant expression systems have a significant advantage compared to other methods of recombinant protein production since plants are much cheaper and easier in cultivation than cell cultures. This system provides rapid and transient expression of heterogonous genes systemically in plants. These virus-based vectors have been used to express genes of pharmaceutical, agronomic value, elicit genetically dominant, gene-silencing phenotypes in plants to determine the functions of unknown genes (Donson et al., 1991; Kumagai et al., 1993, 1995; Masuta et al., 2000; Arazi et al., 2001; Fitzmaurice et at., 2002). They have also been used to produce proteins applicable to various therapeutic interventions and vaccine components that are applicable as therapeutic cancer vaccines (McCormick et al., 1999) Further, expression of sequences in plants by virus expression vectors can result in reprogramming specific metabolic pathways in plants through virus-induced gene-silencing (VIGS) effects (Baulcombe et al., 1999) or protein expression (Fitzmaurice et al., 2002). Heterologous expression of a cDNA for capsanthin-capsorubin synthase (ccs) in *N. benthamiana* resulted in an orange-red phenotype and the accumulation of novel carotenoids capsanthin and capsorubin (Kumagai et al., 1998).

Throughout this application, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THE INVENTION

The present inventors have made intensive studies to provide a clue to the infectivity of pepper mottle virus (PepMoV) which has pathogenicity to plants, particular pepper and tobacco, and to develop a plant virus vector. As results, we have discovered that the plant virus vector could be constructed, with isolation of highly infectious cDNA of pepper mottle virus and analysis of its base sequence.

Accordingly, it is an object of this invention to provide a pepper mottle virus-derived plant infectious nucleic acid molecule.

It is another object of this invention to provide a recombinant vector including the pepper mottle virus-derived plant infectious nucleic acid molecule.

It is still another object of this invention to provide a cell or a plant transformed by the pepper mottle virus-derived plant infectious nucleic acid molecule.

Other objects and advantages of the present invention will become apparent from the following detailed description together with the appended claims and drawings.

In one aspect of this invention, there is provided a pepper mottle virus-derived plant infectious nucleic acid molecule comprising the nucleotide sequence spanning nucleotides 168 to 9371 of SEQ ID NO:1.

The present inventors have made intensive studies to provide a clue to the infectivity of pepper mottle virus (PepMoV) which has pathogenicity to plants, particular pepper and tobacco, and to develop a plant virus vector. As results, we have discovered that the plant virus vector could be constructed, with isolation of highly infectious cDNA of pepper mottle virus and analysis of its nucleotide sequence and an aphid-uninfected pepper mottle virus vector is newly prepared for blocking a virus infection transfer via aphids using the same.

The present invention first achieves the cloning of the infectious full-length pepper mottle virus cDNA from pepper, which enables to perform the molecular studies to the infectivity of pepper mottle virus and to be used in the preparation of the plant virus-based vector. In addition, the present invention prepares the aphid-uninfected pepper mottle virus-based vector to exclude the transition of virus invasion, contributing to obtaining the plants with highly environmental safety under restricted environments.

The present pepper mottle virus-derived plant infectious nucleic acid molecule includes the nucleotide sequence of SEQ ID NO:1.

The term "nucleic acid molecule" as used herein refers to a deoxyribonucleotide or ribonucleotide polymer (including gDNA, cDNA and mRNA) in either single or double-stranded form, including known analogs of natural nucleotides unless otherwise indicated (Scheit, *Nucleotide Analogs*, John Wiley, New York (1980); Uhlman and Peyman, *Chemical Reviews*, 90:543-584 (1990)).

The pepper mottle virus-derived plant highly infectious nucleic acid molecule of this invention has pathogenicity to various plants. Preferably, the present highly infectious nucleic acid molecule exhibits pathogenicity to the genus *Nicotiana* and *Capsicum*. More preferably, the present highly infectious nucleic acid molecule exhibits infectivity to *Nicotiana benthamiana, Nicotiana tabacum* and *Capsicum annum*.

According to a preferable embodiment, the present nucleic acid molecule further comprises the nucleotide sequence spanning nucleotides 1 to 167 of SEQ ID NO:1.

According to a preferable embodiment, the present nucleic acid molecule further comprises the nucleotide sequence spanning nucleotides 9372 to 9655 of SEQ ID NO:1.

According to a preferable embodiment, the nucleic acid molecule has a substituted nucleotide at nucleotide 8584 of SEQ ID NO:1, in which the substituted nucleotide at nucleotide 8584 is a nucleotide containing A, C or T base.

The term "site-directed mutagenesis" used herein refers to a technique to induce an altered form of one or more specific amino acids by changing one or more specific nucleotides in a cloned gene. The site-directed mutagenesis method is described in Ling et al, "Approaches to DNA mutagenesis: an overview", *Anal Biochem.*, 254 (2): 157-178 (1997); Dale et al., "Oligonucleotide-directed random mutagenesis using the phosphorothioate method", *Methods Mol. Biol.*, 57: 369-374 (1996); Smith, "In vitro mutagenesis" *Ann. Rev. Genet.*, 19: 423-462 (1985); Botstein & Shortie, "Strategies and applications of in vitro mutagenesis", *Science*, 229: 1193-1201 (1985); Carter, "Site-directed mutagenesis", *Biochem. J.*, 237: 1-7 (1986); and Kunkel, "The efficiency of oligonucleotide directed mutagenesis", *Nucleic Acids & Molecular Biology* (Eckstein, F. and Lilley, D. M. J. eds., Springer Verlag, Berlin (1987)), which are herein incorporated by references. It is also preferable to carry out the present site-directed mutagenesis by PCR method (Ausubel et al., *Current Protocols in Molecular Biology*, Greene/Wiley Interscience (1987)).

The amino acid substituted by the site-directed mutagenesis in this invention is a portion involved in the aphid infectivity.

According to a conventional study, the aphids missed its infectivity by deleting the amino acids at the N-terminal region of coat protein or by substituting them through site-directed mutagenesis in potyvirus. Particularly, the deletion of Asp-Ala-Gly (DAG) sequence which is a conserved amino acid sequence in potyvirus resulted in the loss of the aphid infectivity (P. L. Atreya et al, *Proc. Natl. Acad. Sci.*, 88: 7887-7891 (1991)).

In another aspect of this invention, there is provided a recombinant vector, comprising (i) the nucleotide sequence as described above, and (ii) a promoter operatively linked to the nucleotide sequence.

The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The vector system of this invention may be performed by various methods known to those skilled in the art and its practical method is described in Sambrook et al., Molecular Cloning, A Laboratory Manual, Cold Spring Harbor Laboratory Press (2001), which is herein incorporated by reference.

The nucleotide sequences involved in the present vector possessed the most preferable utility since they were isolated from a plant virus and had infectivities to plants. Therefore, the vector of this invention provides a plant expression vector including (i) the pepper mottle virus-derived plant infectious nucleic acid molecule; (ii) a promoter which is operatively linked to the nucleotide sequence of (i) and generates a RNA molecule in plant cells; and (iii) 3'-untranslated region responsible of 3'-terminal polyadenylation of the RNA molecule.

According to a preferable embodiment, the suitable promoter of this invention might include any one commonly used by one ordinarily skilled in the art, for example SP6 promoter, T7 promoter, T3 promoter, PM promoter, maize-ubiquitin promoter, Cauliflower mosaic virus (CaMV)-35S promoter, Nopalin synthase (nos) promoter, Figwort mosaic virus 35S promoter, Sugarcane baciliform virus promoter, commelina yellow mottle virus promoter, photo-inducible promoter of small subunit of Ribulose-1,5-bis-phosphate carboxylase (ss-RUBISCO), cytosolic triosphosphate isomerase (TPI) promoter in rice, adenine phosphoribosyltransferase (APRT) or octopine synthase promoter in *Arabidopsis*.

Most preferably, the promoter used in the present invention is a bactriophage SP6 promoter. The sequence of bactriophage SP6 promoter is illustrated in SEQ ID NO:5.

According to a preferable embodiment, the suitable 3'-untranslated region responsible of 3'-terminal polyadenylation includes nos 3'-end of nopaline synthase gene of *Agrobacterium tumefeciens* (Bevan et al., *Nucleic Acids Research*, 11(2):369-385 (1983)), 3'-end of protease I or II of *Agrobacterium tumefeciens*, CaMV 35S terminator and the sequence spanning nucleotides 9372 to 9655 of SEQ ID NO:1.

Most preferably, the suitable 3'-untranslated region responsible of 3'-terminal polyadenylation is the sequence spanning nucleotides 9372 to 9655 of SEQ ID NO:1.

Alternatively, the present vector further includes a gene encoding a reporter molecule (example: green fluorescent protein (GFP), yellow fluorescent protein (YFP), red fluorescent protein (RFP), GFP-derived variant protein, luciferase, β-glucuronidase). Most preferably, the present vector further includes a GFP-encoding nucleotide sequence.

Preferably, the GFP-encoding nucleotide sequence is located between NIb and CP cistron of the pepper mottle virus cDNA of this invention. The present pepper mottle virus plant infectious nucleic acid molecule containing the GFP-encoding nucleotide sequence is illustrated in SEQ ID NO:3.

As described in the Examples below, the invention presents a first success of a pepper mottle virus vector enabling to observe the expression of reporter molecule (e.g., GFP) in plants.

Additionally, the vector of this invention may further deliver a foreign gene instead of gene encoding the reporter molecule.

The term “foreign gene” means a gene to be not present in nature plants. The foreign gene may be a modified form of a gene or genes present in other nature plants, an artificially-synthesized form or a fused form of two or more genes. The plants containing these foreign genes may express gene products not to be produced in nature.

To prepare artificially-synthesized genes, DNA synthesis technique and nucleic acid chemical method are used. For instance, the methods described in Gait, M. J. (1985) Oligonucleotide Synthesis: A Practical Approach, IRL Press; Gait, M. J. (1990) Oligonucleotide Synthesis: A Practical Approach, IRL Press; Eckstein, F. (1991) Oligonucleotides and Analogues: A Practical Approach, IRL Press; Adams, R. L. et al., (1992) The Biochemistry of the Nucleic Acids, Chapman & Hall; Shabarova, Z. et al., (1994) Advanced Organic Chemistry of Nucleic Acids, Weinheim; Blackburn, G. M. et al., (1996) Nucleic Acids in Chemistry and Biology, Oxford University Press; and Hermanson, G. T. (1996) Bioconjugate Techniques, Academic Press are utilized, the disclosure of which is herein incorporated by references.

The foreign gene of this invention includes any gene encoding a suitable protein to be massively expressed in plants, for example, peptides with pharmacological efficacies (e.g., interleukin, chemokine, granulocyte macrophage-colony stimulating factor (GM-CSF), macrophage-colony stimulating factor (M-CSF), granulocyte-colony stimulating factor (G-CSF), multi-CSF (IL-3), erythropoietin (EPO), leukemia inhibitory factor (LIF), tumor necrosis factor, interferon, platelet-derived growth factor (PDGF), epithelial growth factor (EGF), fibroblast growth factor (FGF), hematocyte growth factor (HGF) or vascular endothelial growth factor (VEGF)), hormones (e.g., insulin, growth hormone or thyroid-stimulating hormone), vaccine antibodies, blood products, peptides useful in agriculture such as anti-bacteria protein, various enzymes synthesizing secondary metabolites, inhibitors regulating enzyme activity, glycidin of bean lowering blood pressure or enzymes required for process of bioethanol production (e.g., cellulase, hemicellulase or pectinase), but not limited to.

In addition, the present vector includes antibiotics (example: neomycin, carbenicillin, kanamycin, spectinomycin, hygromycin, etc.)-resistant genes (example: neomycin phosphotransferase (nptII), hygromycin phosphotransferase (hpt), etc.) as a selection marker.

In another aspect of this invention, there is provided a cell transformed or infected with the plant infectious nucleic acid molecule or its transcripts, the recombinant vector or its gene as described above.

In still another aspect of this invention, there is provided a plant transformed or infected with the plant infectious nucleic acid molecule or its transcripts, the recombinant vector or its gene as described above.

The preparation of transformed cells and plants of this invention may be carried out using wild-type and mutated pepper mottle virus-derived plant infectious nucleic acid molecule excluded aphid infectivity through site-directed mutagenesis.

To prepare the transformed cells and transgenic plants of this invention, cDNA sequence and its transcripts, preferably cDNA gene may be used.

The method to prepare the transcripts may be carried out according to the methods known to those skilled in the art. Using the recombinant vector, it is preferable to linealize the vector in preparation of transcripts.

To introduce a foreign nucleotide sequence into plants may be performed by the methods (Methods of Enzymology, Vol. 153, 1987, Wu and Grossman Edition, Academic Press; the disclosure is herein incorporated by reference) known to those skilled in the art. The plant may be transformed by using the foreign nucleotide inserted into a carrier (e.g., vectors such as plasmid or virus) or *Agrobacterium tumefeciens* as a mediator (Chilton et al., *Cell,* 11: 263-271 (1977); the disclosure is herein incorporated by reference), and by directly inserting the foreign nucleotide into plant cells (Lorz et al., *Mol, Genet.,* 199: 178-182 (1985); the disclosure is herein incorporated by reference). For example, electroporation, microparticle bombardment, polyethylene glycol-mediated uptake may be used in the vector containing no T-DNA region.

The term “plant(s)” is understood by a meaning including a plant cell, a plant tissue and a plant seed as well as a mature plant.

The present transgenic plants preferably comprise the genus *Nicotiana* and *Capsicum* and more preferably *Nicotiana benthamiana, Nicotiana tabacum* and *Capsicum annuum.*

BRIEF DESCRIPTION OF THE DRAWINGS

FIG. 1 schematically represents a flowchart for cloning a full-length PepMoV-Vb1 and screening infectious clones.

FIG. 2 schematically represents a procedure to construct the full-length cDNA copy of PepMoV-Vb1 RNA in the downstream of CaMV 35S promoter. The final plasmid was designated as “p35SPepMoV-Vb1”, representing the complete DNA copy of PepMoV-Vb1 genome.

FIG. 3 represents a procedure to construct pSP6PepMoV-Vb1/GFP. GFP gene was inserted between NIb and CP cistron of pSP6PepMoV-Vb1. A NIb/CP recognition peptide was introduced between NIb and CP.

FIG. 4 represents RT-PCR analysis (A) of mRNA from *N. benthamiana* infected with pSP6PepMoV-Vb1/GFP and primer positions (B) on viral genome. Specific primers were used to amplify PepMoV-Vb1-CP (~820 bp) and GFP (~700 bp). Primers were designed for producing each different PCR fragments in size.

FIG. 5 schematically represents a method to prepare pSP6PepMoV-Vb1/GFP-NAT vector. The base sequences represent sense (NAT5'; SEQ ID NO:33) and antisense (NAT3'; SEQ ID NO:34) primers used in a vector preparation.

FIG. 6 schematically represents a strategy to completely sequence PepMoV-Vb1 genome.

Figure 9:
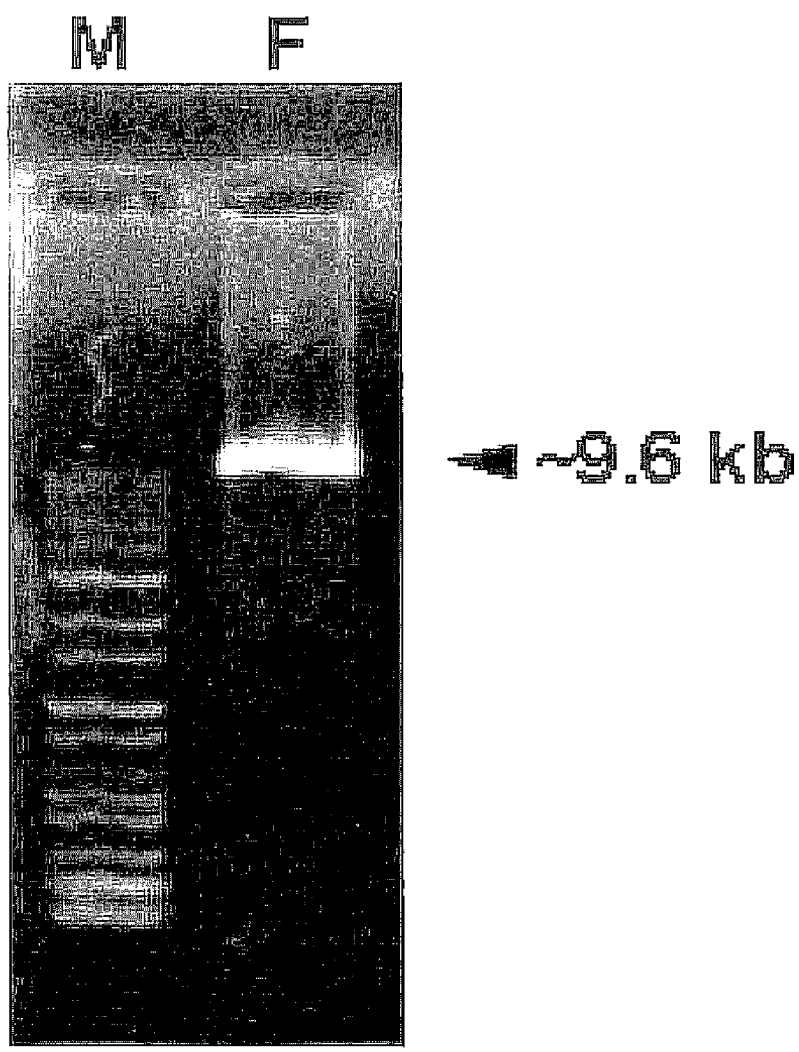

FIG. 9 is a putative full-length RT-PCR product of PepMoV-Vb1 cDNA. Lane M is a ladder; Lane F and arrowhead represent PCR products.

Figure 10:
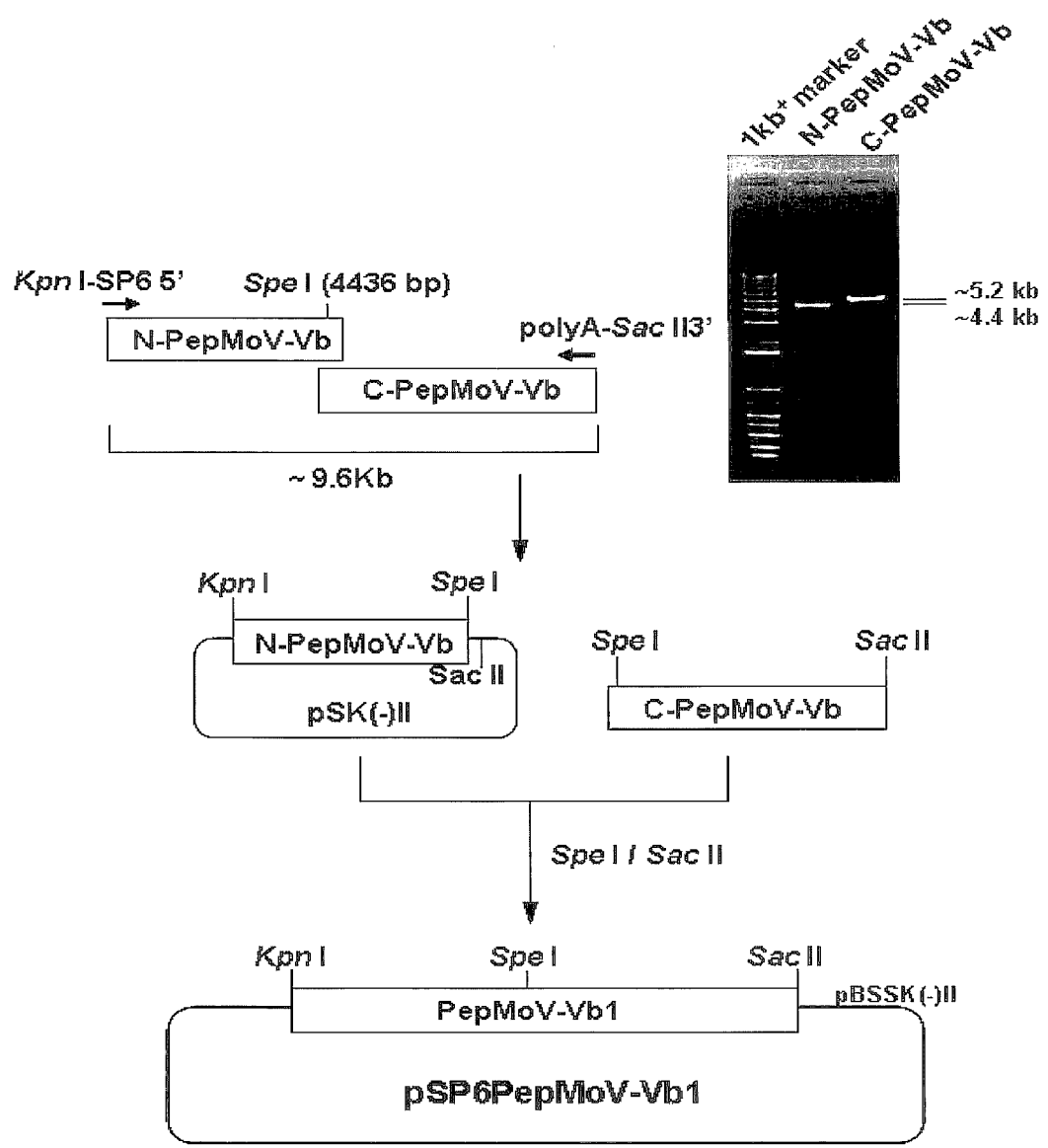

FIG. 10 shows a procedure to construct pSP6PepMoV-Vb1 vector containing a bacteriophage SP6 RNA promoter and RT-PCR products of PepMoV-Vb1. N-PepMoV-Vb, N-terminal RT-PCR products (~4.4 kb); C-PepMoV-Vb, C-terminal RT-PCR products (~5.2 kb).

Figure 11:
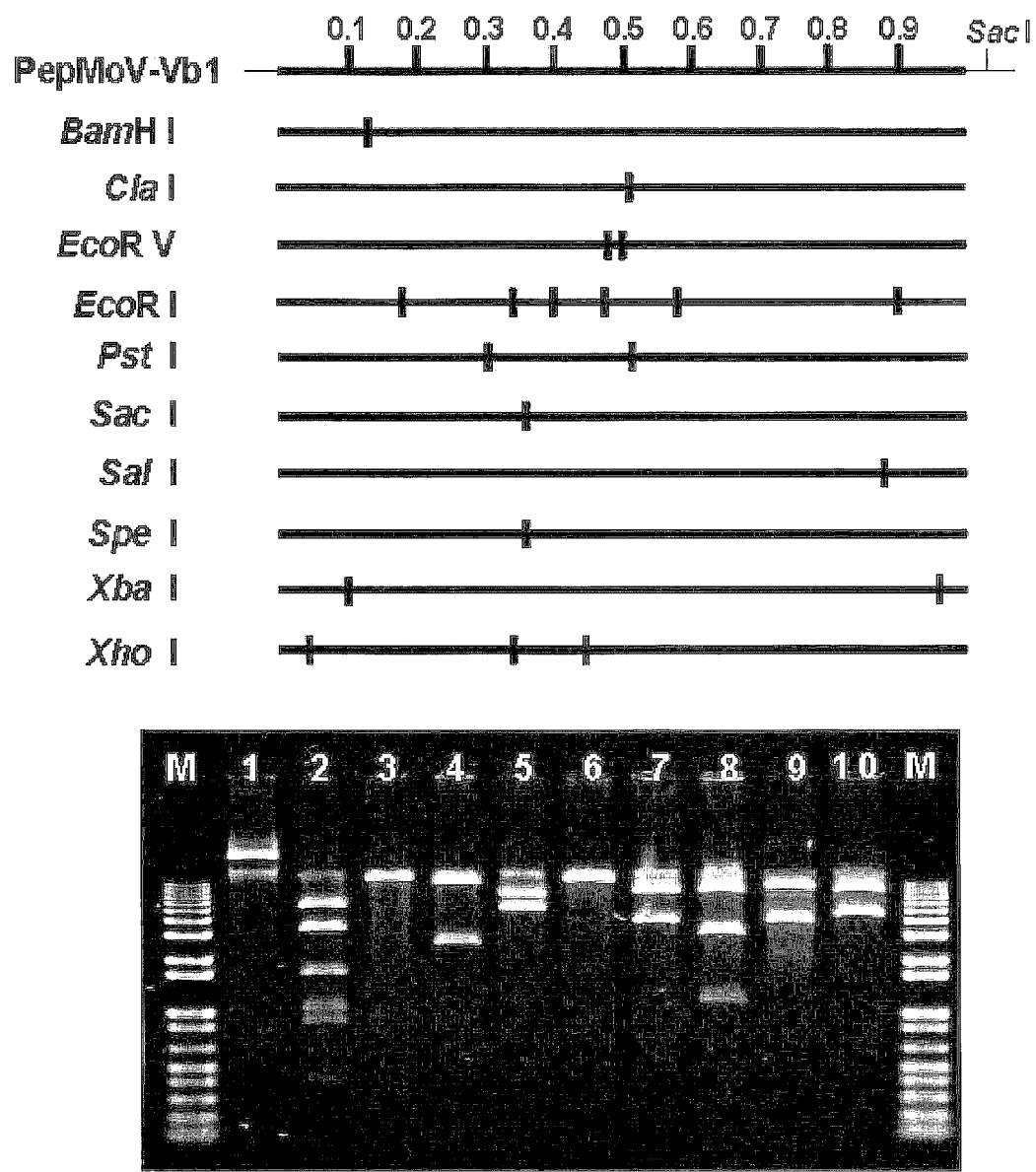

FIG. 11 represents a comparison of RFLP (restriction fragment length polymorphism) patterns of the full-length DNA of pSP6PepMoV-Vb1 based on the nucleotide sequence of PepMoV-Vb1. Upper panel: restriction map, bold horizontal line, full-length cDNA of pSP6PepMoV-Vb1, thin line, pBSSK (–) II vector. Lower panel: RFLP pattern of pSP6PepMoV-Vb1; Lane M, 1 kb+ DNA ladder; lane 1, no cut; lane 2, EcoR I; lane3, EcoR V; lane 4, PstI; lane 5, Sac I; lane 6, SalI; lane 7, Xba I; lane 8, XhoI; lane 9, BamH I/Cla I; lane 10, Spe I/SalI.

FIG. 12 represents the comparison of RFLP (restriction fragment length polymorphism) patterns of the putative full-length DNA of p35SPepMoV-Vb1. RT-PCR analysis (A) and primer positions (B) used in restriction mapping or PCR analysis.

FIG. 13 is the photograph of 1% agarose gel representing in vitro transcript product of pSP6PepMoV-Vb1. Lane M, 1 kb$^+$ DNA ladder; lane 1, transcripts of SP6PepMoV-Vb1; lane 2, transcripts from putative full-length RT-PCR products.

FIG. 14 shows photographs representing the symptoms in *N. benthamiana* infected with in vitro transcripts of wild-type PepMoV-Vb and pSP6PepMoV-Vb1 by mechanical inoculation. At 5-14 days post-inoculation, the photographs were taken: A (5 dpi), C and E (10 dpi), PepMoV-Vb/Sap-infected plants; B (5 dpi), D and F (10 dpi), pSP6PepMoV-Vb1-infected plants.

FIG. 15 represents RT-PCR (A) and Western blotting (B) analysis in *N. benthamiana* infected with pSP6PepMoV-Vb1 clone. Lane 1, leaf extract of plants infected with wild-type PepMoV-Vb; lane 2, healthy plants as negative control; lane 3-9, leaves extracts of plants infected with in vitro transcripts of pSP6PepMoV-Vb1 by mechanical inoculation; lane M, 1 kb$^+$ DNA ladder and protein size marker. The experiments were carried out two times.

FIG. 16 shows photographs representing the symptoms in *C. annum* ECW inoculated with pSP6PepMoV-Vb1. Photographs: A, C, E and G, wild-type PepMoV-Vb/Sap; B, D, F and H, pSP6PepMoV-Vb1/sap.

FIG. 17 represents the results to detect virus-specific genes or proteins in *N. benthamiana* inoculated with in vitro transcripts of pSP6PepMoV-Vb1. The infectivity of pSP6PepMoV-Vb1 to *N. benthamiana* were analyzed by RT-PCR using CT primer (A) and VPg-specific primer (B) and by Western blotting with anti-serum against PepMoV-CP. Lane 1, inoculated leaves of plants infected with pSP6PepMoV-Vb1; lane 2, systemic upper leaves of plants infected with pSP6PepMoV-Vb1; lane 3, inoculated leaves of plants infected with PepMoV-Vb/Sap; lane 4, systemic upper leaves of plants infected with PepMoV-Vb/Sap; lane 5, healthy leaves as negative control; lane M, 1 kb$^+$ ladder and protein size marker.

FIG. 18 is the photograph of 1% agarose gel representing in vitro transcription products of pSP6PepMoV-Vb1/GFP. Lane M1, 1 kb$^+$ ladder (~100 ng); lane M2, 1 kb$^+$ ladder (~300 ng); i-T, Sac II-linealized pSP6PepMoV-Vb1 templates; i-I, in vitro transcripts of pSP6PepMoV-Vb1; ii-T, Sac II-linealized pSP6PepMoV-Vb1/GFP templates; ii-I, in vitro transcripts of pSP6PepMoV-Vb1/GFP.

FIG. 19 is the photograph visualizing green fluorescent protein (GFP) under UV light in *N. benthamiana* infected with pSP6PepMoV-Vb1/GFP. The photographs were taken at 4, 5, 7, 10 and 14 days post-inoculation (dpi), respectively.

FIG. 20 is the photograph exhibiting green fluorescence illuminated by GFP under UV light in flower (A) and root (B) of *N. benthamiana* infected with pSP6PepMoV-Vb1/GFP at 30 dpi.

FIG. 21 represents Western blotting for PepMoV-Vb coat protein of systemically-infected tobacco leaves at 14 dpi. Lane M, protein size marker; lane 1, healthy plants; lane 2, pSP6PepMoV-Vb1-infected plants; lane 3, Ls-CMV-inoculated plant. The position of PepMoV-Vb coat protein is indicated by the arrowhead.

FIG. 22 is the photograph exhibiting green fluorescence in the systemic leaves of pepper infected with pSP6PepMoV-Vb1/GFP. The first true leaves of pepper were inoculated with progeny viruses obtained from *N. benthamiana* infected with pSP6PepMoV-Vb1/GFP. The photographs in all leaves were taken under UV light at 5 (a, a', b, b'), 12 (c, c') and 30 (d, d', e, e') dpi, respectively. The photograph (e') is to magnify the circle-indicated region of d'.

FIG. 23 represents the stability analysis of pPepMoV-Vb1/GFP through passage (P) in the systemically-infected leaves of *N. benthamiana*. The primers were used in RT-PCR amplification of PepMoV-Vb1-CP and GFP. Lane 1, pSP6PepMoV-Vb1-infected plants at 30 dpi (P0); lane 2, pSP6PepMoV-Vb1/GFP-infected plants at 30 dpi (P0); lane 3-5, pSP6PepMoV-Vb1/GFP-infected plants at 7, 14 and 21 dpi (P1), respectively; lane 6-7, pSP6PepMoV-Vb1/GFP-infected plants at 7 and 14 dpi (P2), respectively.

FIG. 24 is the result to analyze the infectivity of SP6PepMoV-Vb1/GFP-NAT. By analyzing the expression patterns of GFP induced by inoculating the transcripts of SP6PepMoV-Vb1/GFP-NAT and SP6PepMoV-Vb1/GFP into pepper, the infectivity of SP6PepMoV-Vb1/GFP-NAT is similar to that of SP6PepMoV-Vb1/GFP in whole pepper plant as well as leaves and stems of pepper plant.

FIG. 25 represents a system to examine the aphid infectivity of pSP6PepMoV-Vb1/GFP-NAT constructed as a vector for blocking aphid transition. The contamination caused by aphids and inaccuracy of the results were excluded by analyzing an aphid-mediated infectivity in pepper and tobacco plants using a separated cultivation system prepared to determine the exact aphid mediation infectivity.

The present invention will now be described in further detail by examples. It would be obvious to those skilled in the art that these examples are intended to be more concretely illustrative and the scope of the present invention as set forth in the appended claims is not limited to or by the examples.

EXAMPLES

Experimental Materials and Methods

1. Sources of Plants

*Nicotiana benthamiana* was generally used for propagation of PepMoV-Vb1. It could be easily infected with virus sap by mechanical inoculation and full-length clone. For the host range study of pSP6PepMoV-Vb1/GFP, the following plant species were inoculated with progenies of SP6PepMoV-Vb1/GFP, *Nicotiana tabacum* cv. Xanthi-nc, Samsun NN, Samsun nn, *Solanum lycopersicon, Chenopodium amaranticolor*, zucchini squash (C. pepo cv. Black Beauty) and pepper plants were grown in a greenhouse of Seoul Women's University in Seoul, Korea. *N. benthamiana* infected with the SP6PepMoV-Vb1/GFP was ground in 0.01 M phosphate buffer, pH 7.2. The inoculum was applied to leaves of healthy plants dusted with carborundum.

2. Virus Sources

Pepper mottle virus (PepMoV-Vb) used throughout this work was originally isolated from *Capsicum annuum* L. var. grossum in Hwasung, Kyungki province in Korea. The isolate is available from Plant Virus GenBank, Seoul, Korea (PVGB accession No. PV-0170).

3. Bacterial Strains and Plasmids

Competent *Escherichia coli* strains were used ABLE K, SURE, XL10-Gold (Stratagene, USA), DH5α and JM109. A full-length clone amplified and maintained in XL10-Gold. The plasmids of pBluescript SK 2(−) (Stratagene, USA) and pGEM T-Easy (Promega, USA) were used for full-length construction and sub-cloning of cDNAs of PepMoV-Vb1.

4. Construction of Full-Length cDNA of PepMoV-Vb1

The work flow for the construction of in vitro- and in vivo infectious full-length cDNA clone of PepMoV-Vb1 was outlined in FIG. 1.

4-1. A Full-Length cDNA Copy of PepMoV-Vb1 RNA with SP6 Promoter

A full-length cDNA copy of PepMoV-Vb1 RNA was synthesized by long template RT-PCR with a primer set of Kpn I-SP6 5' and polyA-Sac II 3'. Primer used synthesis of cDNAs of PepMoV-Vb1 were listed in Table 1. Reverse transcription PCR(RT-PCR) was performed in 50 μl of reaction volume containing total RNA template, 1× buffer, 0.5 mM dNTP, 1 μM downstream primer, and 10 U SuperScriptII reverse transcriptase. PCR was performed in 50 μl of reaction volume consisting of 1 μl of first strand cDNAs, 1× buffer, 0.5 mM dNTP, 0.75 mM $MgCl_2$, 0.5 μM of the upstream and the downstream primers, and Expand long template DNA polymerase (Roche). RT-PCR was performed along to cycles of five different annealing temperatures. PCR was performed 4 min at 94° C. followed by five cycle of 20 sec at 94° C., 40 sec at 55° C. and 10 min at 68° C., ten cycles of 20 sec at 94° C., 40 sec at 56° C. and 9 min at 68° C., ten cycles of 20 sec at 94° C., 40 sec at 57° C. and 10 min at 68° C., five cycles of 20 sec at 94° C., 40 sec at 58° C. and 10 min at 68° C. Finally, the mixtures were incubated at 68° C. for 15 min for extension.

TABLE 1

Primer sequences for constructing a full-length PepMoV-Vb1 and Sequencing.

| Fragment | Primers | Primer sequence (5' → 3') |
|---|---|---|
| 1 | KpnI-SP6 5' | 5'-GAGAGGTACCATTTAGGTGACACTATAG AAATTAAAACATAACATACAA-3' (SEQ ID NO: 6) |

TABLE 1-continued

Primer sequences for constructing a full-length PepMoV-Vb1 and Sequencing.

| Fragment | Primers | Primer sequence (5' → 3') |
|---|---|---|
| | BamHI 3' | 5'-CCCTTAAATGTTGTCGAG-3' (SEQ ID NO: 7) |
| 2 | BamHI 5' | 5'-CTTCAAAATGATTGGATC-3' (SEQ ID NO: 8) |
| | PacI 3' | 5'-ATCGAGGGTGAGAGAATG-3' (SEQ ID NO: 9) |
| 3 | PacI 5' | 5'-AGTGAGCGAGTTTCATGC-3' (SEQ ID NO: 10) |
| | BgIII 3' | 5'-AGTGAGCACACAACACCC-3' (SEQ ID NO: 11) |
| 4 | BglII 5' | 5'-AACTGAAGATCTCAAGAA-3' (SEQ ID NO: 12) |
| | SpeI 3' | 5'-CCACCTGGCAGAGAGGTGGAG-3' (SEQ ID NO: 13) |
| 5 | SpeI 5' | 5'-GGCTTACTCTTTGTTCCTCGTG-3' (SEQ ID NO: 14) |
| | ClaI 3' | 5'-TAGCTCTGAGTGCATTTG-3' (SEQ ID NO: 15) |
| 6 | ClaI 5' | 5'-TTGCGATCATCATCGATT-3' (SEQ ID NO: 16) |
| | NcoI 3' | 5'-CTCAAACAGCTTTGCCGG-3' (SEQ ID NO: 17) |
| 7 | NcoI 5' | 5'-CATGCAGATCCATGGCTT-3' (SEQ ID NO: 18) |
| | SalI 3' | 5'AATATTTGGGGACGTGCC-3' (SEQ ID NO: 19) |
| 8 | SalI 5' | 5'-CTTGAATACAAACCAAGC-3' (SEQ ID NO: 20) |
| | polyA-KpnI 3' | 5'-GGGGTACCT(30)GTCTCTCTCATGC CAAC-3' (SEQ ID NO: 21) |

4-2. A Full-Length cDNA Copies of PepMoV-Vb1 RNA with CaMV 35S Promoter

The plasmid p35SPepMoV-Vb1 contained the CaMV 35S promoter, the complete PepMoV-Vb1 DNA and poly (A) 30 tract. First, CaMV 35S promoter and 5' region of PepMoV-Vb1 (1-1393 nt) was fused by PCR with primer sets of Sph I 35S pro 5' and 35S pro3' or 35S pro-end 5' and BamH I PepMoV 3', and then fusion PCR product (PepMoV-Vb1/5'SphI-BamHI) was dehydrolyzed by Sph I-BamH I. The plasmid pBS/SK2 (−) was modified for use as the backbone in the construction of the 35SPepMoV-Vb1 vector by deletion of the multiple-cloning site except BamH I and Sph I (provided by Prof. I. Uyeda in Hokkaido University; See, Reference). Subsequently, this fragment was introduced into modified pBS/SK2 (−). Next, Kpn I-Nco I-Pst I linker was inserted into BamH I site of pPepMoV-Vb1/SphI-BamHI and the region of Kpn I-Nco I PepMoV-Vb1 (7305-9670 nt contained poly-(A)30) was introduced into pPepMoV-Vb1/5'SphIBamHI-NcoIKpnI3'. Finally, a full-length construct of PepMoV-Vb1 was completed by BamH I-Nco I (1393-7305 nt) region of PepMoV-Vb1 insertion to pPepMoV-Vb1/5'SphIBamHI-NcoIKpnI3'. This clone hereafter referred to as "p35SPepMoV-Vb1" (FIG. 2).

5. Construction of GFP Expression Vector Base on pSP6PepMoV-Vb1

The GFP cDNA was PCR-amplified from turboGFP vector (Evrogen, Russia) and introduced into pSP6PepMoV-Vb1 so that the open reading frame for GFP was placed in-frame between the sequences coding for NIb and CP, generating a recombinant plasmid, pSP6PepMoV-Vb1/GFP. GFP was cloned using primer set of 5' turboGFP (5'-ATGGAGAGC-GACGAGAGC-3'; SEQ ID NO:27) and 3' turboGFP (5'-TTCTTCACCGGCATCTGC-3'; SEQ ID NO:28). A NIa protease cleavage site was introduced between GFP and CP. The primers to construct the pSP6PepMoV-Vb1/GFP are summarized in Table 2.

Figure 2:
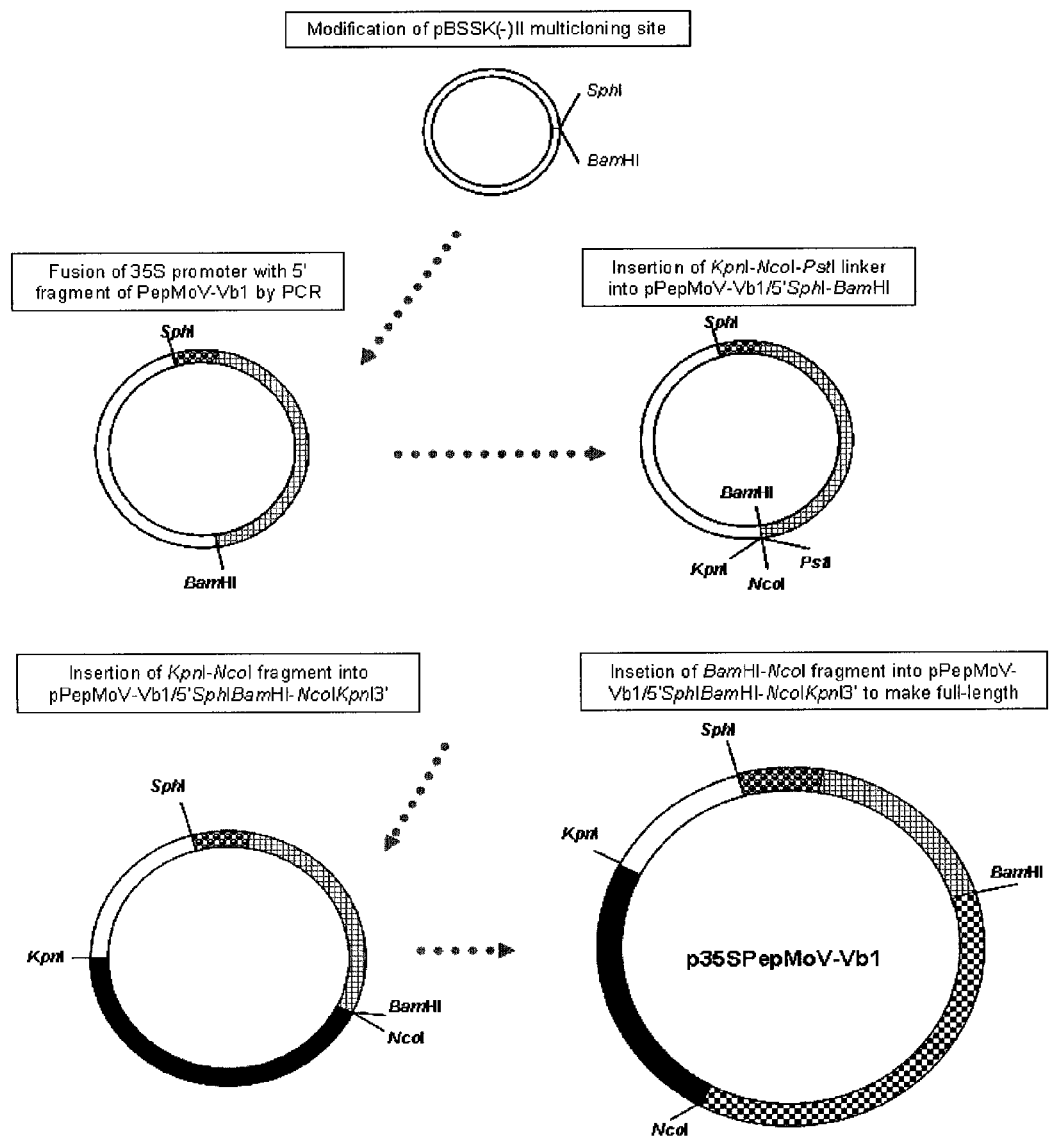
Figure 3:
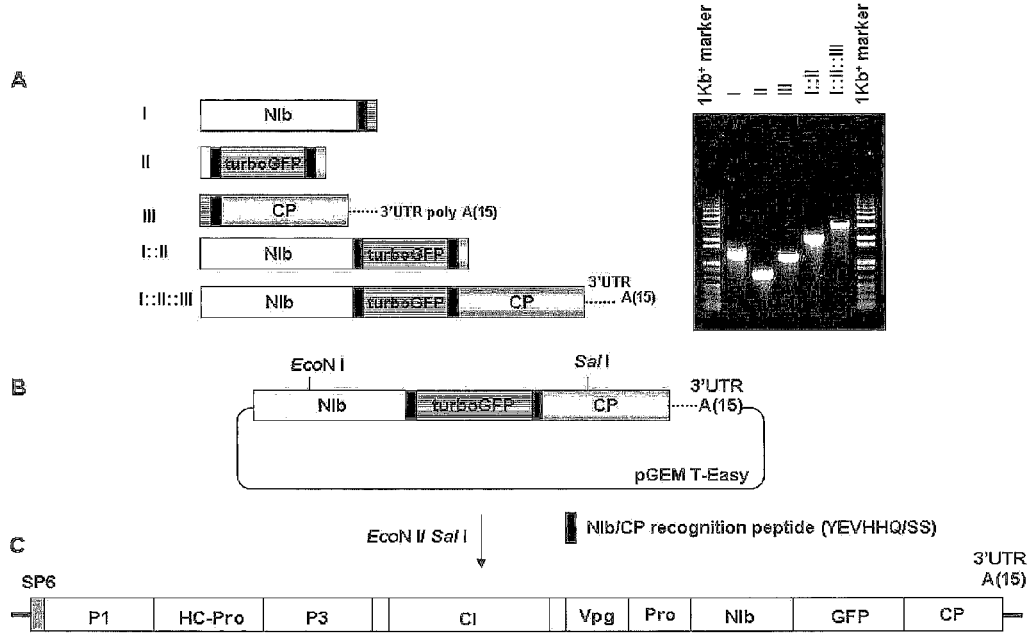

For pSP6PepMoV-Vb1/GFP, PCR fragments were obtained NIb-GFP, GFP and GFP-CP. The PCR fragments NIb-GFP and GFP-CP are designed overlapped 3' region of NIb and 5' region of GFP or overlapped 3' region of CP and 5' region of CP, respectively. The DNA fragment of the 3' region of NIb fused to turboGFP was first amplified with the primer NcoI-5' and NIbGFP3' (FIG. 3, A-I) and then, the DNA fragment of the 5' region of CP fused to NIb::GFP was amplified with the primer pairs of GFPCP 5' and PepMoV-Sac II 3' (FIG. 3, A-III). The NIb-GFP and GFP-CP gene were amplified with the primer NcoI-5' and CP-GFP3' (FIG. 3, A-I::II) or NcoI-5' and polyA-SacII3' (FIG. 3, A-I::II::III), respectively. The GFP gene was amplified with NIbGFP 5' and GFP-CP3' (FIG. 3, A-III). Finally, the fusion PCR product was cloned pGEM T-Easy vector (FIG. 3, B). The junctions and the inserted sequences were confirmed by sequencing. The NIb::GFP::CP fragment was cut with EcoN I-Sal I and ligated into EcoN I-Sal I treated pSP6PepMoV-Vb1, creating the recombinant plasmid pSP6PepMoV-Vb1/GFP. The plasmid construct was amplified and maintained in *E. coli* XL10-Gold as pSP6 PepMoV-Vb1 and hereafter referred to as "PepMoV-Vb1/GFP" (FIG. 3, C).

TABLE 2

Fusion PCR primers to construct SP6PepMoV-Vb1/GFP

| Fragment | Primer | Primer sequence |
|---|---|---|
| I | NcoI-5' | 5'-CATGCAGATCCATGGCTT-3' (SEQ ID NO: 18) |
| | NIbGFP3' | 5'-CTCGTCGCTCTCCATGCTGCTCTG ATGATGAACTTC-3' (SEQ ID NO: 22) |
| II | NIbGFP5' | 5'-GTTCATCAGAGCAGCATGGAGAGC GACGAGAGCGG-3' (SEQ ID NO: 23) |
| | CPGFP3' | 5'-GATGAACTTCATATTCTTCACCGG CATCTGCATCCCG-3' (SEQ ID NO: 24) |
| III | GFPCP5' | 5'-GATGCCGGTGAAGAATATGAAGTT CATCATCAGAGCAG-3' (SEQ ID NO: 25) |
| | polyA-SacII3' | 5'-GAGACCGCGGT15GTCTCTCTCAT GCCAACTACG-3' (SEQ ID NO: 26) |
| I::II | Nco I-5' | 5'-CATGCAGATCCATGGCTT-3' (SEQ ID NO: 18) |
| | CPGFP3' | 5'-GATGAACTTCATATTCTTCACCGG CATCTGCATCCCG-3' (SEQ ID NO: 24) |

TABLE 2-continued

Fusion PCR primers to construct SP6PepMoV-Vb1/GFP

| Fragment | Primer | Primer sequence |
|---|---|---|
| I::II::III | Nco I-5' | 5'-CATGCAGATCCATGGCTT-3' (SEQ ID NO: 18) |
| | polyA-SacII3' | 5'-GAGACCGCGG T15GTCTCTCTCA TGCCAACTACG-3' (SEQ ID NO: 26) |
| GFP | TurboGFP 5' | 5'-ATGGAGAGCGACGAGAGC-3' (SEQ ID NO: 27) |
| | TurboGFP 3' | 5'-TTCTTCACCGGCATCTGC-3' (SEQ ID NO: 28) |
| CP | PepMoV-CP5' | 5'-AGCGCTCAAGCTCAGACAC-3' (SEQ ID NO: 29) |
| | PepMoV-CP3' | 5'-CATATTTCTGACCCCAAGCAG-3' (SEQ ID NO: 30) |
| VPg | PepMoV-VPg5' | 5'-GCTCTAGAGGACGCTCTAAGAC G-3' (SEQ ID NO: 31) |
| | PepMoV-VPg5' | 5'-GGGGTACCTTCGTGCTTCACAA C-3' (SEQ ID NO: 32) |
| NAT1 | NAT5' | 5'-GAGCAGCTCAAGATCAGACACATTGGA CGCTGAAGAGGAGAAAAAG-3' (SEQ ID NO: 33) |
| NAT2 | NAT3' | 5'-GTGGCTACTTCTTTATTTTCTTTTTC TCCTCTTCAGCGTCCAATGTGTC-3' (SEQ ID NO: 34) |

6. Assessments of Infectivity of pSP6PepMoV-Vb1 and pSP6PepMoV-Vb1/GFP

6-1. In vitro Transcription and Infectivity Test

Full-length cDNA clones of the pSP6PepMoV-Vb1 and pSP6PepMoV-Vb1/GFP were used as template for in vitro transcription reaction following plasmid linearization with Sac II. In vitro transcription reactions were carried out in a volume of 50 μl containing 10 mM DTT, 5 mM rATP, 5 mM rCTP, 5 mM rUTP, 0.5 mM rGTP, 0.5 mM cap analog (m7 GpppG), 20 unit of SP6 RNA polymerase, 1 unit RNase inhibitor (TAKARA, Japan) and 1 μg of plasmid DNA linearized with Sac II. After incubation for 15 min at 37° C., 5 μl of 5 mM rGTP was added and incubation was continued for an additional 1 hour. For infectivity test of pSP6PepMoV-Vb1 and pSP6PepMoV-Vb1/GFP, *N. benthamiana* plants were inoculated in the first expanded leaf when they were 5 weeks old. Inoculations with the in vitro transcripts were derived from pSP6PepMoV-Vb1 and pSP6PepMoV-Vb1/GFP that Sac II linearized plasmid with SP6 RNA polymerase. More than 5 independent experiments were carried out under the same experimental conditions. Those that developed symptoms were analyzed for accumulation of PepMoV-Vb1-encoded RNA or protein and GFP by RT-PCR, western blot and GFP fluorescent monitoring.

6-2. Reverse Transcription-Polymerase Chain Reaction (RT-PCR)

RT-PCR was performed to confirm PepMoV-Vb1 infection in tested hosts. Total nucleic acids were extracted from infected plant using a phenol/chloroform method were used as templates. RT was performed in a reaction mixture (20 μl) containing 2.5 mM MgCl$_2$, 0.5 mM of each dNTPs, 1 μl of 50 μM reverse primer, 1× buffer, 1 unit RNase inhibitor, and 2.5 units MuLV reverse transcriptase (Qbiogene, France) at 42° C. for 60 minutes. PCR was performed in a 50 μl of the synthesized cDNA, 1× buffer, 2.5 mM MgCl$_2$, 0.04 unit Ex-Taq polymerase (TAKARA, Japan), 1 μl of 50 μM reverse and forward primers. To detect the CP, VPg, and inserted entire GFP we used specific primers listed in Table 2, respectively.

To distinguish GFP sequence in the recombinant PepMoV-Vb1 RNA or not, we used the primer pair Nco I 5' and Sal I 3' (Table 1). This corresponds to the 3' region of the NIb cistron (nucleotide 7295-7312) and the 5' region of the CP cistron (nucleotide 8937-8954) as shown in FIG. 4.

6-3. Western Blot Analysis

For western blot analyses, protein samples were separated on SDS-polyacrylamide gel and transferred onto NC membrane by electro-blotting using an electro transfer unit (Bio-Rad, USA). Membrane was washed three times with TBST buffer (20 mM Tris (pH 7.5), 150 mM NaCl, and 0.1% Tween 20) and blocked for 1 hours with 5% nonfat dried milk. Membrane was probed with antibody (1:1,000 dilutions; immunoglobulin G (IgG) fraction; 1 mg/ml) against Pep-MoV-CP or turboGFP. Membrane was washed three times in TBS-T buffer and incubated with an alkaline phosphatase (AP)-conjugated secondary antibody (1:7,500 dilution; Promega, USA). Membrane was washed three times with TBST buffer and rinsed once in AP-substrate buffer (0.1 M Tris (pH 9.5), 100 mM NaCl, and 50 mM MgCl$_2$). To visualize antibody-specific proteins, membrane was reacted with AP-substrate solution (Western Blue Stabilized Substrate Solution, Promega, USA) and the color reaction was terminated with 0.05 M EDTA solution.

6-4. Detection of GFP Fluorescence

Expression of GFP in the inoculated and the upper noninoculated leaves was monitored under illumination with a UV-light and by epifluorescent microscopy (Leica, epifluorescence microscope; Leica, Solms, Germany). The GPF-expressed plants were photographed with a Nikon distal camera (D-70).

7. Analysis of Stability and Passage Experiments of pSP6PepMoV-Vb1/GFP

The stability of pSP6PepMoV-Vb1/GFP was assessed by successive passages of recombinant from systemically infected plant tissues. Recombinant progeny virus in the infected plants of N. benthamiana was mechanically transferred to healthy plants at 7 days intervals. After several passages, the leaves collected from the tested host plants were analyzed by western blotting and RT-PCR with GFP or CP antisera and appropriate primer pairs, respectively. To further monitoring, the possible deletion of viral genome or escape of GFP from pSP6PepMoV-Vb1/GFP and RT-PCR analysis from its progeny-infected hosts was performed by PCR with specific primers.

8. Construction of NAT (Non-Aphid Transmission) Vector based on pSP6PepMoV-Vb1/GFP For pSP6PepMoV-Vb1/GFP-NAT, the induction of mutation in the particular region was performed according to mutagenesis induction kit (Stratagene, USA). After PCR using NAT5' and NAT3' primers, and pSP6PepMoV-Vb1/GFP as a template, the PCR products were digested with Dpn I. Non-mutated templates were removed and then transformed into *E. coli* strain, XL1-Blue. By sequence analysis, it is confirmed to substitute E for G in the DAG region and then the region amplified with NcoI-5' and polyA-Sac 113' primers was cloned into pGEM T-Easy vector to exclude infectivity loss or other problems caused from PCR errors in the resulting pSP6PepMoV-Vb1/GFP-NAT. The clone was sequenced and then inserted into pSP6PepMoV-Vb1/GFP restricted with EcoN I-Sal I, generating a pSP6PepMoV-Vb1/GFP-NAT. The plasmid construct was amplified and maintained in *E. coli* XL10-Gold and hereafter designated as a "PepMoV-Vb1/GFP-NAT" (FIG. 5).

9. Aphid Infectivity Analysis

The procedures to grow and manipulate aphids and to analyze the plants were performed according to a conventional method (Atreya, D. D., Raccah, B. and Pirone, T. P. Virology 178:161-165 (1990)). Virus-mediated infectivity experiments were carried out using wingless adult insects of *Aphis gossypii* and *Myzus persicae*. To compare aphid-mediated invasion, the aphids were separated from the plants for 2 hrs before inoculation and suck juices for 15 min in pepper and tabacum plants infected with pSP6PepMoV-Vb1/GFP-NAT transcripts (acquisition access period). Thus, the aphids were collected and transferred to the healthy plants, following the inoculation for 1 hr (inoculation access period). A separated cultivation system was used to obtain the contamination of the aphids and exact results and plants were observed in the incubation room (FIG. 25).

Results

1. Complete Nucleotide Sequencing of PepMoV-Vb1

To construct infectious full-length cDNA clone of PepMoV-Vb, the PepMoV-Vb genome divided into overlapped segments contained unique restriction enzyme site by RT-PCR as shown in FIG. 6. Eight PCR products were synthesized representing essentially the entire genome and each PCR product subsequently cloned into the pGEM-T Easy vector system (Promega, U.S.A.) (FIG. 7). Each clone was sequenced and full genome RNA sequences of PepMoV-Vb was assembled based on PepMoV-Vb sequence. All primers were also designed based on PepMoV-Vb sequence (GenBank/EMBL/DDBJ accession No.AB126033). The complete nucleotide sequence of PCR fragments was not identical to PepMoV-Vb. Hereafter we renamed assembled full-length PepMoV-Vb to PepMoV-Vb1. The oligonucleotide primers used to synthesize the PCR products and sequencing of cDNA clones were listed in Table 1.

The genome of PepMoV-Vb1 consists of 9,640 nucleotides long contained an extra guanosine residue at the 5' terminus and 3' end following a poly (A) 15 tract. The genome RNA encodes a single large ORF coding for polyprotein of 349 kDa (3068 aa), which is the typical genome structure of the potyviruses. The ORF start with an AUG start codon at position 168 to 170 and end with the termination codon UGA at position 9372 to 9374. The 5'- and 3' NTR was consisted of 168 nucleotides and 267 nucleotides, respectively. The 5'NTR of PepMoV-Vb1 was present two conserved blocks of sequences which are referred to as box 'a' and 'b' in potyvirus. Box a (AUACAACAU) and b (UCAAGCAU) was detected from the 5' end in PepMoV-Vb1. These sequences and their secondary structure may be important for processes such as encapsidation, translation or replication (Riechmann et al., 1992)

PepMoV-Vb1 has nine sequences of the potential cleavage site and the genome organizations of PepMoV-Vb1 are shown in Table 3.

TABLE 3

Amino acid sequences present in the amino acid residue of the potential cleavage site of PepMoV-Vb1 polyprotein and adjacent to the cleavage site

| Connection | Amino acid position | | | | | | | | |
|---|---|---|---|---|---|---|---|---|---|
| site | P6 | P5 | P4 | P3 | P2 | P1 | P'1 | P'2 | P'3 | Protease |
| P1/HC-Pro | L | H | M | E | Q | Y | S | T | S | P1-Pro |
| HC-Pro/P3 | K | H | Y | R | V | G | G | T | V | HC-Pro |

TABLE 3-continued Amino acid sequences present in the amino acid residue of the potential cleavage site of PepMoV-Vb1 polyprotein and adjacent to the cleavage site

| Connection site | Amino acid position | | | | | | | | | Protease |
|---|---|---|---|---|---|---|---|---|---|---|
| | P6 | P5 | P4 | P3 | P2 | P1 | P'1 | P'2 | P'3 | |
| P3/6K1 | K | Q | V | I | H | Q | R | S | T | NIa-Pro |
| 6K1/CI | S | E | V | R | H | Q | S | L | D | NIa-Pro |
| CI/6K2 | Q | F | V | H | H | Q | S | K | S | NIa-Pro |
| 6K2/VPg | S | E | V | S | H | Q | G | R | S | NIa-Pro |
| VPg/NIa | E | V | V | K | H | E | A | K | T | NIa-Pro |
| NIa/NIb | E | C | V | R | E | Q | A | H | T | NIa-Pro |
| NIb/CP | Y | E | V | H | H | Q | S | S | S | NIa-Pro |

The cleavage site at C-terminal of P1 occurs probably at the dipeptide Y/S (287-288 aa) and HC-Pro/P3 cleavage site also occurs at G/G dipeptide (743-744 aa). The remaining seven protease recognition sites are putatively cleaved by the NIa-Pro at dipeptide Q/R (1104-1105 aa), Q/S (1156-1157, 1790-1791, 2795-2796 aa), E/A (2030-2031 aa), Q/G (1842-1843 aa) and Q/A (2276-2277 aa), which are also found in other potyvirus genomes. All of these cleavage sites for PepMoV-Vb1 showed identical to those of other known PepMoV isolates.

In addition, several conserved amino acid residues organized in functional motif of potyviruses were detected in the PepMoV-Vb1 polyprotein. The FIVRG motif (259-263 aa; (SEQ ID NO:35)) of PI genome was reported proteolytic domain. The CCCTT motif (577-581 aa; (SEQ ID NO:36)) and LAIGN motif (533-537 aa; (SEQ ID NO:37)) were present in HC-Pro of PepMoV-Vb1 probably involved in the viral long distance movement and cell to cell movement respectively. The conserved nucleotide-binding motif VGS-GKST (1243-1249 aa; (SEQ ID NO:38)) and the RNA helicase motif DECH (1330-1333 aa; (SEQ ID NO:39)) were found in the CI of the genome. The conserved RNA-dependent RNA polymerase motif of positive-stranded viruses, CDADGS (2521-2526 aa; (SEQ ID NO:40)) and SGC35X3NTX3OGDD (2586-2629 aa; (SEQ ID NO:41)), were found in the NIb of the genome. Motifs known to be involved in the aphid transmission KLTC (337-340 aa; (SEQ ID NO:42)), PTK (595-597 aa), FRNK (466-469 aa; (SEQ ID NO:43)) and DAG (2804-2896 aa) could be found in the HC-Pro and CP of PepMoV-Vb1. The CP cistron also contained an amino acid motif, RX43D (2958-3002 aa; (SEQ ID NO:44)) that was required for viral long distance movement.

2. Sequence Alignments and Phylogenetic Analyses of PepMoV-Vb1

The complete sequence of PepMoV-Vb1 showed high sequence identity with other PepMoV isolates, PepMoV-Vb (99.3%), PepMoV-C (94.9%) and PepMoV-FL (94.0%), at the nucleotide level. PepMoV-Vb1 polyprotein amino acid sequence identity with PepMoV-Vb (98.7%), PepMoV-C (95.8%) and PepMoV-FL (95.9%) isolate. Table 4 shows percentages amino acid identity of PepMoV-Vb1 functional proteins compared to the corresponding proteins of some potyvirus members infecting *Solanaceous* species. Amino acid identity of the entire PepMoV-Vb with PepMoV isolates ranged from 98.7% (Vb1) to 95.8% (PepMoV-C), and with other some potyvirus, from 66.8% (PTV) to 44.1% (ChiVMV and PSbMV).

The multiple alignments of the deduced amino acid sequences showed that P1 is highly variable. The highest identity was found within isolates of PepMoV, Vb (93.7%), C (87.8%) and FL (85.0%), while the percentage identity with other potyviruses range from 13.5% with PSbMV to 35.1% with PTV. PepMoV-Vb1 CP revealed the highest identity on the amino acid with the isolate Vb (99.3%), C (98.2%), FL (97.1%) followed by ChiVMV, PTV and PVY. The overall identity between PepMoV-Vb1-CP was lowest with the CP of TVMV (55.9%). P1 and N-terminal region of the CP protein is variable potyviral protein, both in length and amino acid sequence.

TABLE 4

Sequence homology between PepMoV-Vb1 and Solanaceae plant-infectious potyviruses

| Virus | P1 | HC-Pro | P3 | 6K1 | CI | 6K2 | VPg | NIa-Pro | NIb | CP | Poly protein |
|---|---|---|---|---|---|---|---|---|---|---|---|
| ChiVMV | 14.7 | 46.9 | 19.4 | 38.5 | 49.6 | 52.0 | 50.0 | 46.9 | 58.5 | 73.4 | 44.1 |
| PepMoV-Vb | 93.7 | 98.2 | 99.2 | 100.0 | 98.9 | 100 | 99.5 | 98.8 | 99.2 | 99.3 | 98.7 |
| PepMoV-C | 87.8 | 97.4 | 96.6 | 98.1 | 97.3 | 98.0 | 96.3 | 97.6 | 91.8 | 98.2 | 95.8 |
| PepMoV-FL | 85.0 | 94.2 | 96.4 | 98.1 | 98.4 | 100.0 | 94.1 | 97.6 | 97.1 | 97.1 | 95.9 |
| PepSMV | 25.4 | 61.6 | 32.8 | 63.5 | 68.1 | 62.7 | 71.3 | 70.0 | 75.5 | 72.0 | 60.6 |
| PSbMV | 13.5 | 45.6 | 18.2 | 34.6 | 52.9 | 37.3 | 48.6 | 43.8 | 59.4 | 57.4 | 44.1 |
| PTV | 35.1 | 66.1 | 40.7 | 76.9 | 76.5 | 66.7 | 79.8 | 75.1 | 78.4 | 73.4 | 66.8 |
| PVA | 24.4 | 47.6 | 25.5 | 38.5 | 53.3 | 39.2 | 48.7 | 51.2 | 58.0 | 57.9 | 46.6 |
| PVMV | 17.5 | 47.9 | 20.0 | 40.4 | 51.3 | 52.9 | 49.5 | 50.6 | 59.9 | 60.5 | 45.6 |
| PVV | 34.4 | 59.3 | 42.4 | 78.8 | 76.7 | 68.6 | 78.7 | 71.4 | 77.9 | 69.7 | 65.5 |
| PVY | 32.7 | 63.7 | 34.4 | 67.3 | 69.8 | 54.9 | 69.1 | 65.0 | 73.4 | 74.3 | 61.4 |
| TEV | 18.7 | 47.0 | 27.3 | 48.1 | 55.1 | 49.0 | 53.2 | 47.4 | 60.0 | 60.2 | 46.8 |
| TVMV | 22.9 | 46.7 | 24.1 | 51.9 | 52.9 | 39.2 | 45.3 | 43.8 | 63.7 | 55.9 | 46.3 |
| WPMV | 40.0 | 65.2 | 43.8 | 76.9 | 74.4 | 68.6 | 80.3 | 71.8 | 77.9 | 73.4 | 66.7 |

Figure 8:
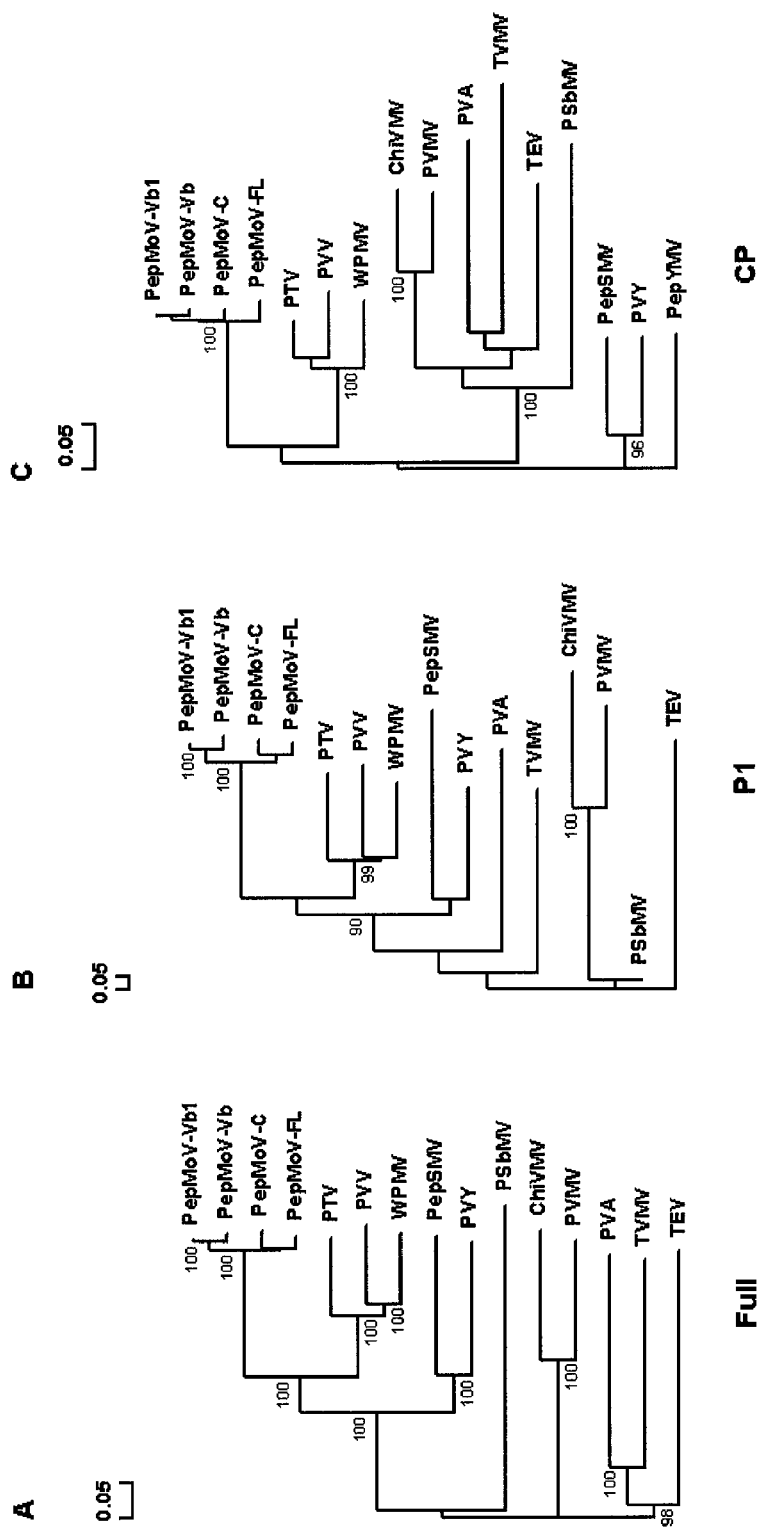
FIG. 8 represents phylogenic trees of 15 species of Solanaceae-infectious potyvirus, which is based on the multiple alignments of complete polyprotein (A), P1 (B) and CP sequences (C).

To understand evolution trees and a phylogenetic relationship of PepMoV-Vb1, the amino acid sequences of the ten mature functional proteins of P1, CP and entire polyportein were compared with other potyviruses infecting Solanaceae plants. PepMoV-Vb1 showed high homology with previously reported other strains of PepMoV-Vb, PepMoV-C and PepMoV-FL. Therefore, PepMoV-Vb1 isolate was grouped with PepMoV-Vb, PepMoV-C and PepMoV-FL (FIG. 8).

3. Cloning of Full-Length cDNA of PepMoV-Vb1

To generate infectious full-length cDNA clone, we performed RT-PCR using primer set of KpnI-SP6 5' and polyA-Sac II 3'. Although we was amplified a full-length cDNA copy of PepMoV-Vb about 9.6 kb by long template RT-PCR system successfully (FIG. 9), directed cloning of putative full-length PCR product was laborious. Hence, strategy was designed to avoid toxicity of the viral genome. The procedure of the construction of a full-length cDNA clone of PepMoV-Vb1 with the SP6 RNA promoter is outlined in FIG. 4. The pSP6PepMoV-Vb1 was based on the genome of PepMoV-Vb1. The PepMoV-Vb1 genome was split in two parts using unique enzyme site within the CI cistron. The unique Spe I restriction enzyme site in the CI region permitted the joining of overlapped two parts of PepMoV-Vb1 by sub-cloning. The former researchers of the present inventors already obtained the partial clone (pPepMoV-Vb1-N) from the 5' region included the SP6 RNA promoter extended to position 4531 in viral genome. The overlapping C-terminus PepMoV-Vb1 fragment was amplified from the first strand cDNA with primer pair of Spe 15' and polyA-Sac II 3' (Table 1). The C-terminal RT-PCR fragment of PepMoV-Vb1 introduced into pPepMoV-Vb1-N using Spe I and Sac II restriction enzyme sites. Finally, a full-length cDNA clone of PepMoV-Vb1 with a poly (A) tail of 15 residues was constructed by ligating the Spe I-Sac II RT-PCR fragment (4437-9640 nt of PepMoV-Vb1) with Spe I-Sac II digested pSKPepMoV-Vb-N containing 1-4437 of PepMoV-Vb genome preceded by SP6 RNA promoter (FIG. 10). The present inventors hereafter designated the full-length cDNA clone of PepMoV-Vb1 regulated by SP6 RNA promoter as "pSP6PepMoV-Vb1". RFLP analysis was performed with pPepMoV-Vb1 by restriction enzymes, BamH I, Cla I, EcoR V, Pst I, Sac I, Sal I, Spe I, Xba I and Xho I. The RFLP patterns of full-length clone were identical to those complete nucleotide sequence for PepMoV-Vb1 (FIG. 11).

Figure 6:
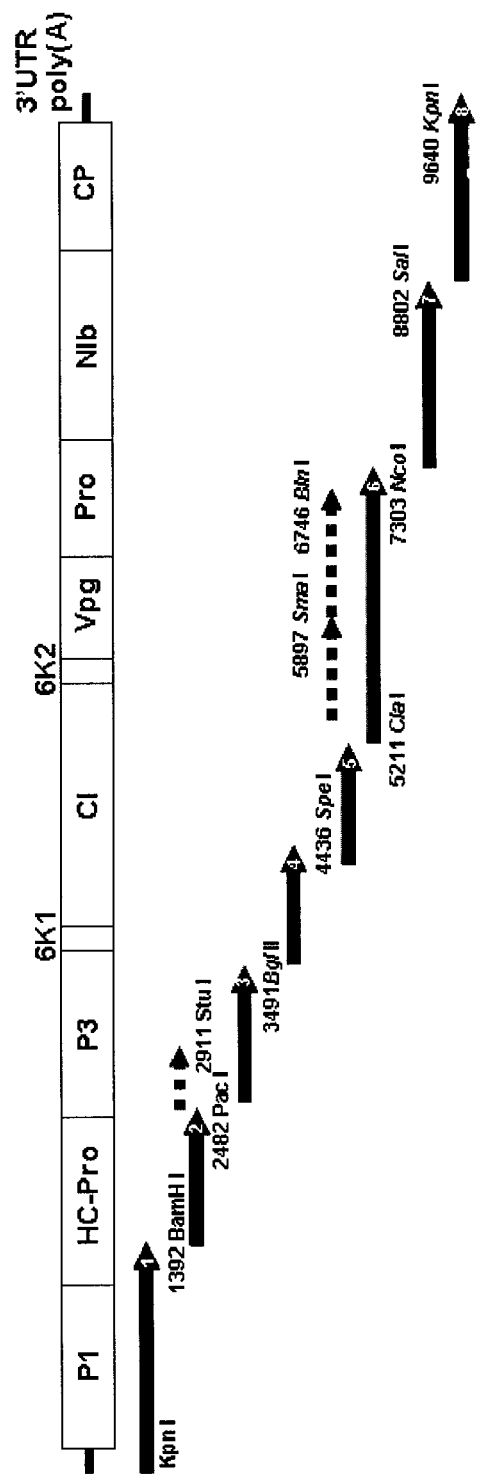
Figure 7:
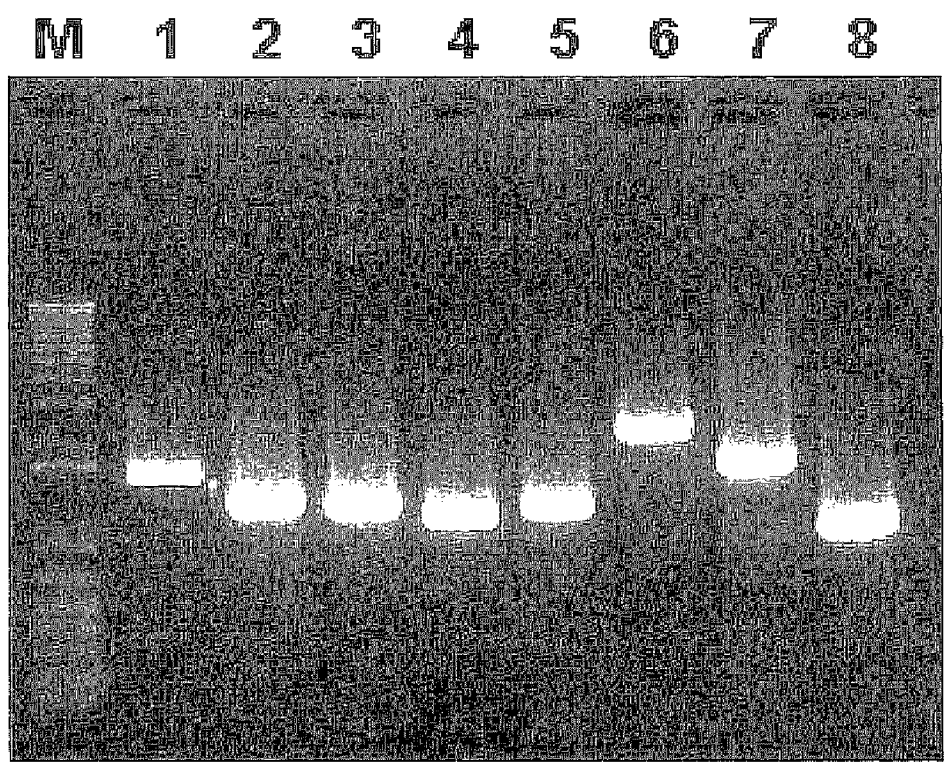
FIG. 7 shows RT-PCR products of PepMoV-Vb1.

Based on the sequence information a strategy was made for assembly of a clone under 35S promoter (FIG. 6). FIG. 6 shows the construction of the plasmid containing the full-length cDNA clone was placed under the control of the CaMV 35S promoter. We hereafter full-length cDNA clone of PepMoV-Vb1 regulate by CaMV 35S promoter referred to p35SPepMoV-Vb1. RFLP analysis was also performed with p35SPepMoV-Vb1 by restriction enzymes, SphI/Pst I, EcoR V and Pst I. The RFLP patterns of full-length clone was identical to those complete nucleotide sequence for PepMoV-Vb1. And RT-PCR was conducted to confirm of p35SPepMoV-Vb1 with specific pair of primer 35S pro 5' and BamH 13' (FIG. 12). The infectivity of the putative ten selected constructs was tested in N. benthamiana by mechanical inoculation. The plasmid p35SpepMoV-Vb1 did not infect any of N. benthamiana plants by manual mechanical inoculation. It was repeated the manual inoculation ten times on more than 20 N. benthamiana plants, but still no infectivity was noticed.

4. Infectivity Assay of In Vitro Infectious SP6PepMoV-Vb1 Clone

Figure 13:
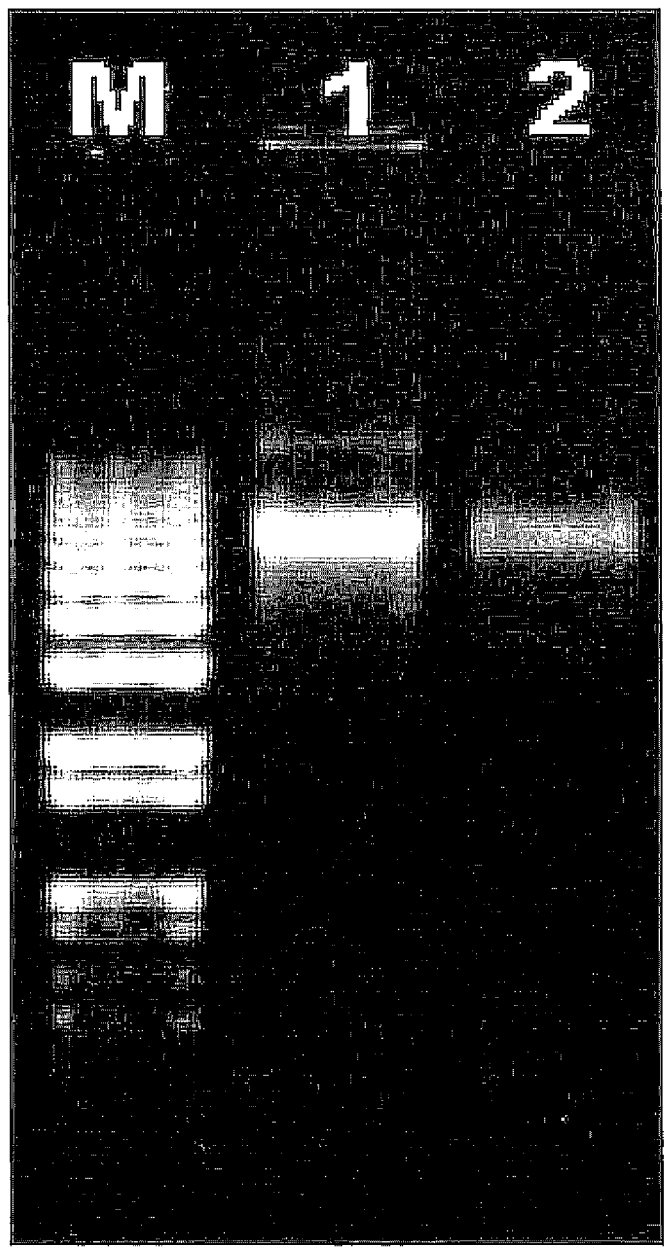
Figure 14:
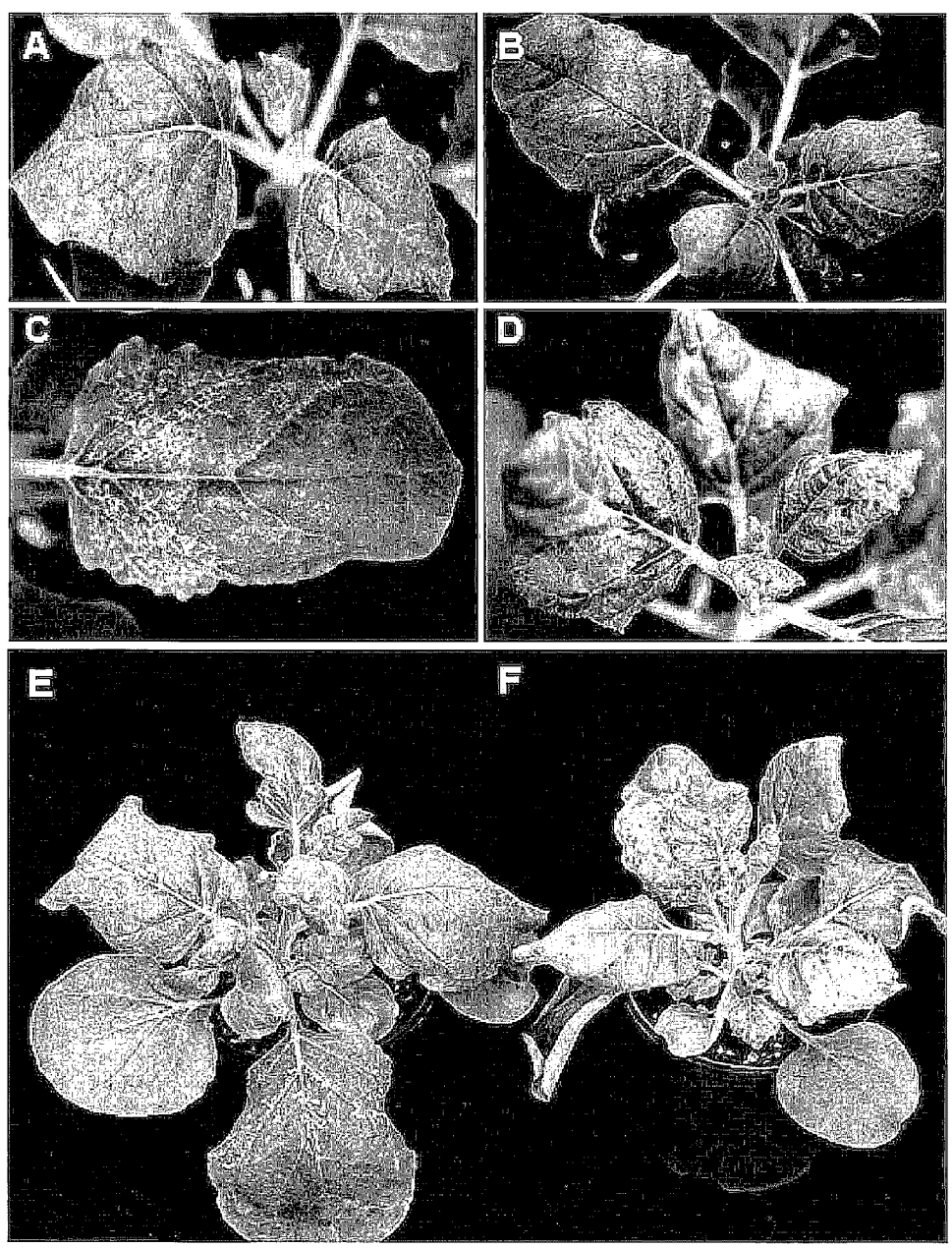

To analyze infectivity of SP6PepMoV-Vb1clone, Sac II-cut full-length cDNA clone was used as templates for in vitro transcription. Capped in vitro transcripts generated pPep-MoV-Vb1 and putative full-length PCR product of PepMoV-Vb1 were infected onto N. benthamiana using mechanically inoculation method (FIG. 13). pPepMoV-Vb1 full-length clone was systemically infectious when inoculated onto N. benthamiana, whereas PCR directed in vitro transcript was not infectious onto N. benthamiana. Symptoms induced 3-5 dpi (days post-inoculation; depending on greenhouse conditions) slight faster (1 or 2 days) than initiation of infection with PepMoV-Vb/Sap. The initial symptom of inoculated N. benthamiana with SP6PepMoV-Vb1 showed severe vein clearing in upper leaves at 4 dpi. No significant symptom differences between pSP6PepMoV-Vb1 and PepMoV-Vb in upper leaves of N. benthamiana were observed. In vitro transcripts of PepMoV-Vb1 were able to develop typical vein banding, severe mosaic symptom, leaf malformation, leaf distortion and yellowing on N. benthamiana (FIG. 14).

5. Confirmation of Infectivity of SP6PepMoV-Vb1 Clone

Figure 15:
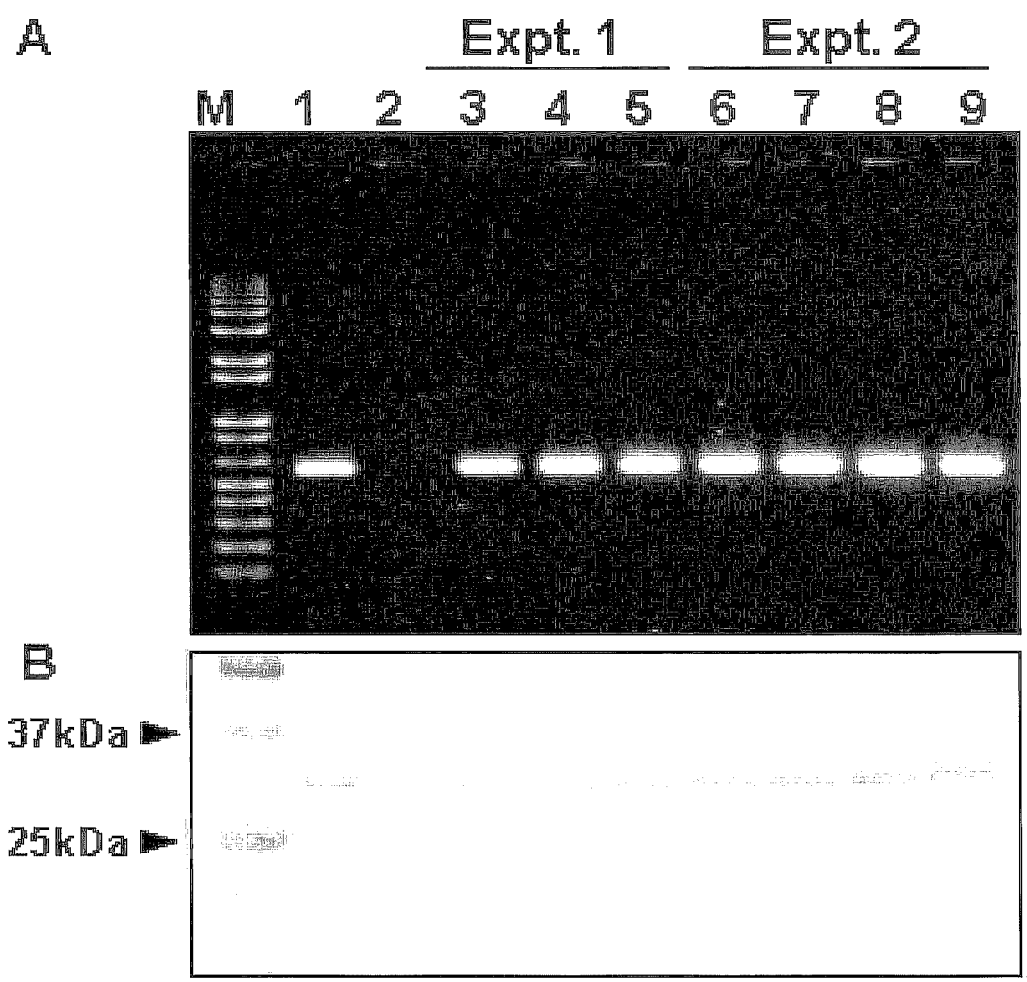

To confirm infectivity of pSP6PepMoV-Vb1, in vitro transcription of pSP6PepMoV-Vb1 was repeated several times and each transcript was inoculated onto N. benthamiana plants. pSP6PepMoV-Vb1 inoculated N. benthamiana plants were analyzed by RT-PCR (FIG. 15A) and Western blot (FIG. 15B) with PepMoV-CP specific primer and antiserum against PepMoV-Vb to confirm infection of the virus, respectively. RT-PCR product and protein corresponding to the expected size of PepMoV-CP were detected in extracted samples from the pSP6PepMoV-Vb1-infected leaf tissues. No signal was detected in samples from Mock treated plants (FIG. 15).

Figure 16:
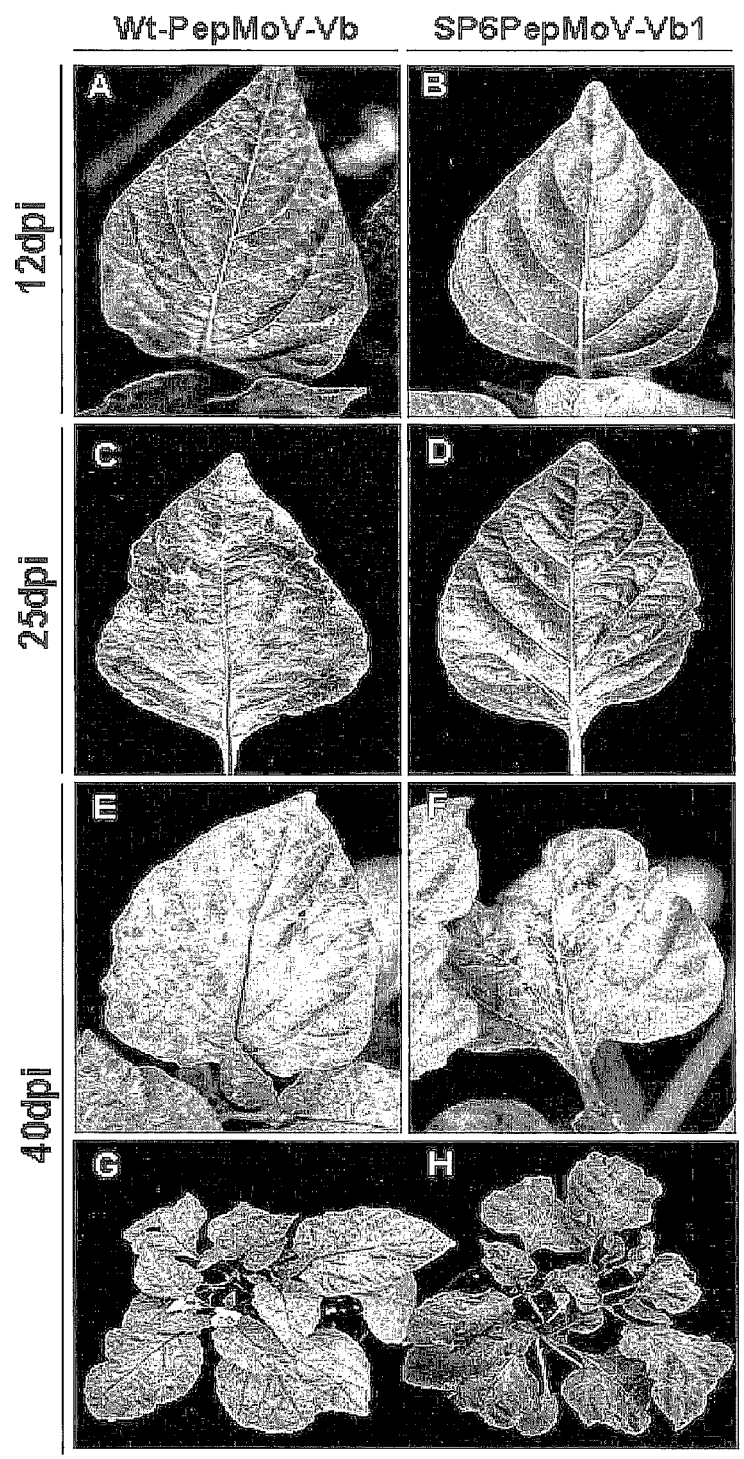
Figure 17:
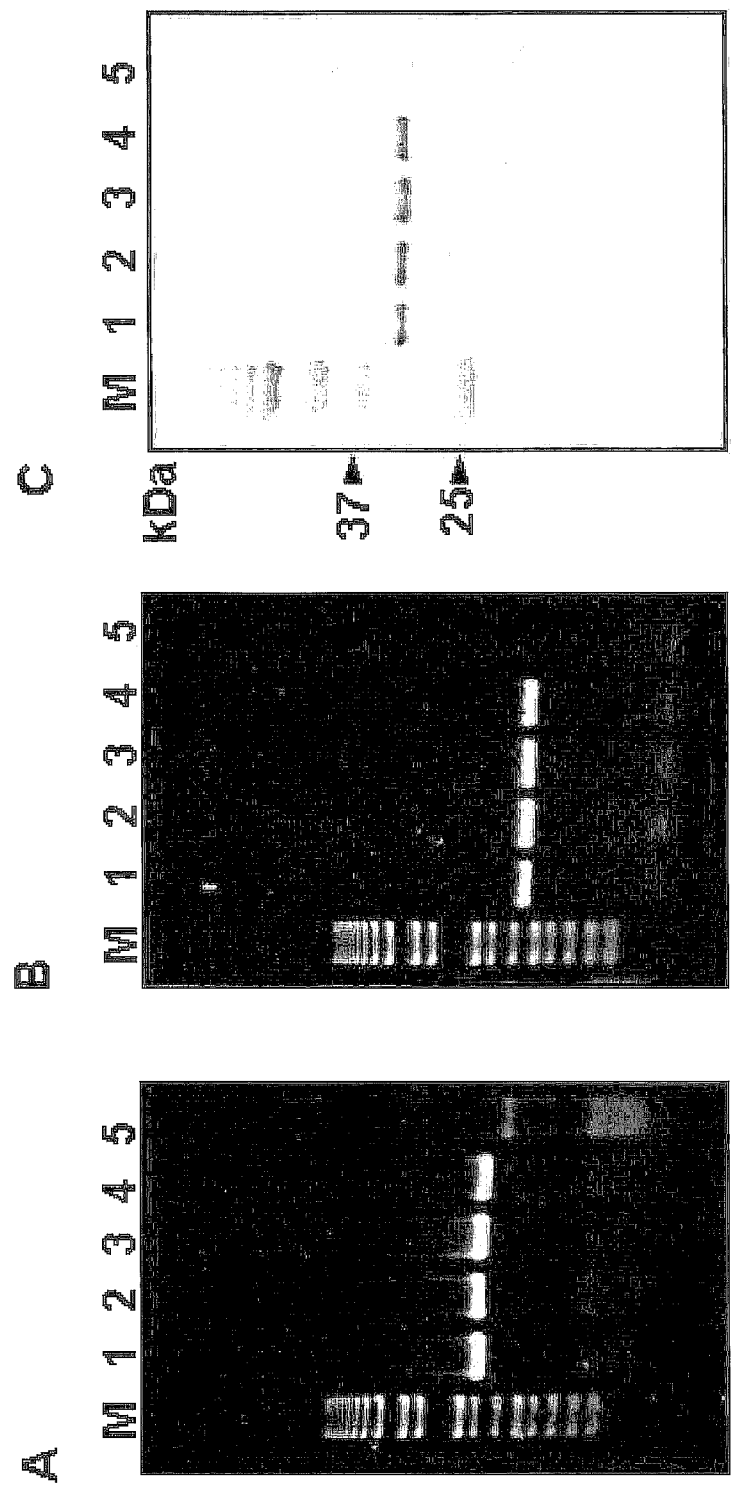

In addition, N. benthamiana plants showing symptoms of viral infection after inoculation with in vitro transcript of SP6PepMoV-Vb1 was used as a source of inocula to inoculate new sets of N. benthamiana and pepper plants. In order to confirm that the infectivity of pSP6PepMoV-Vb1 in pepper plants, the crude sap from leaf tissues of infected N. benthamiana inoculated onto ECW pepper. Typical symptoms of PepMoV-Vb infection appeared on plants of N. benthamiana as well as pepper plants inoculated with crude sap derived from SP6PepMoV-Vb1 at 3 and 4 dpi respectively. They were showed severe mosaic and malformation symptom to the upper leaves of peppers about 12 days after inoculation (FIG. 15B). In pepper plants, the virus produced typical mottle, severe mosaic symptoms and leaf distortion (FIGS. 16D, 16F and 16H). This test repeated the inoculation several times on more than five N, benthamiana plants, and still infectivity of SP6PepMoV-Vb1 was highly infectious. All plants were analyzed by RT-PCR with specific primer pairs of PepMoV-CP (FIG. 17A) or PepMoV-VPg (FIG. 17B) and western blot with antiserum against PepMoV-Vb to confirm infection of the virus in virus inoculated leaves and noninoculated upper leaves of N. benthamiana. By immunoblotting analysis, a 30 kDa protein corresponding to the CP of PepMoV was detected in the plants infected by the in vitro transcripts derived from SP6PepMoV-Vb1 (FIG. 17C). This is the first report on infectious full-length cDNA cloning of PepMoV isolated from pepper plants.

6. Construction of the a Novel Viral Vector Based on SP6PepMoV-Vb1 Genome

A highly infectious cDNA clone of SP6PepMoV-Vb1 was applied as a viral vector. The pSP6PepMoV-Vb1/GFP was based on the genome of PepMoV-Vb1. A schematic diagram of construct made is shown FIG. 3. The GFP gene (turboGFP) encoding green fluorescent protein was inserted between the cistrons for NIb and CP in pSP6PepMoV-Vb1 by two-step fusion PCR. The inserted GFP in the polyprotein was flanked by the proteolytic cleavage sites recognized by the viral NIa proteinase (YEVHHQ/SS). Finally, the fusion PCR product was cloned pGEM T-Easy vector (FIG. 3B). The NIb::GFP::CP fragment of two-step fusion PCR product was dehydrolyzed with EcoN I-Sal I and ligated into EcoN I-Sal I treated pSP6PepMoV-Vb1, creating the recombinant plasmid pSP6PepMoV-Vb1/GFP.

Figure 18:
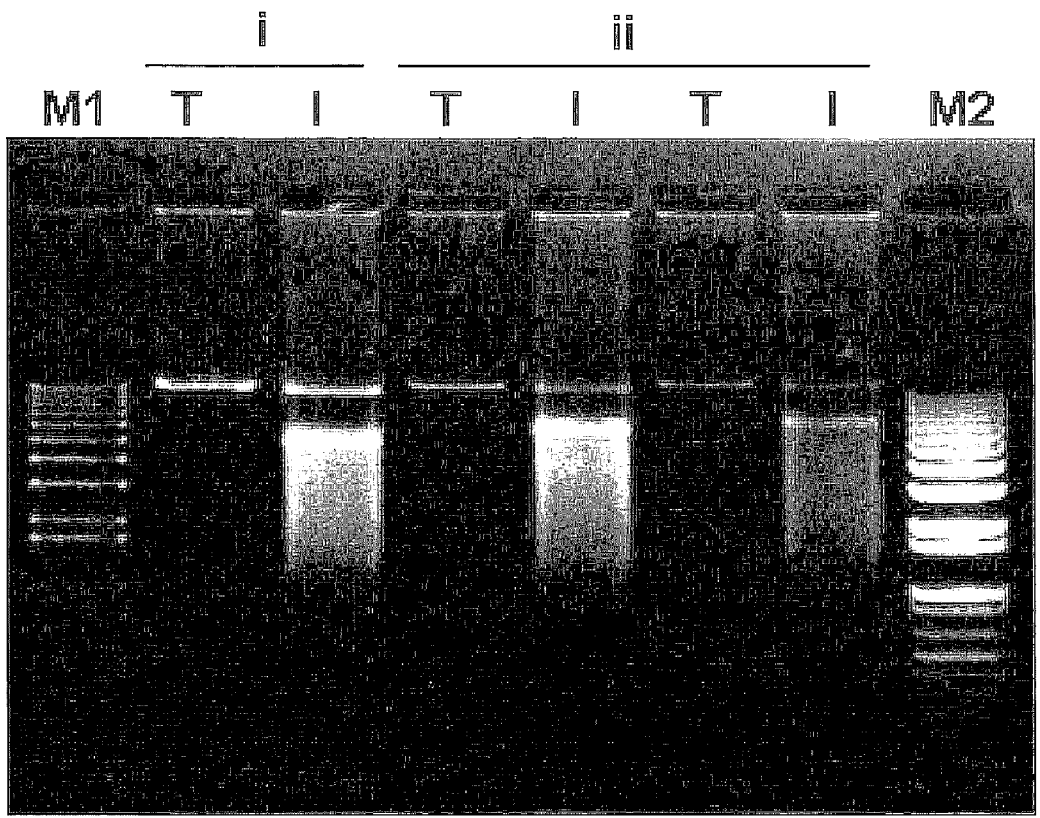
Figure 19:
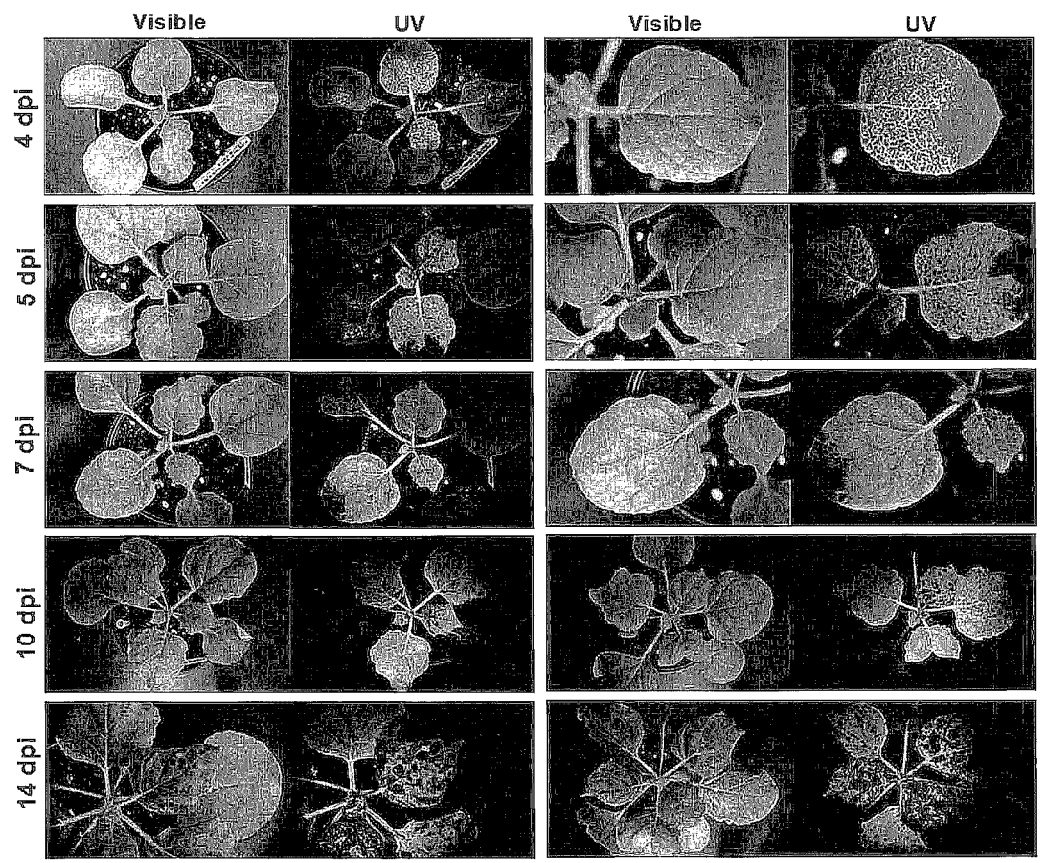
Figure 20:
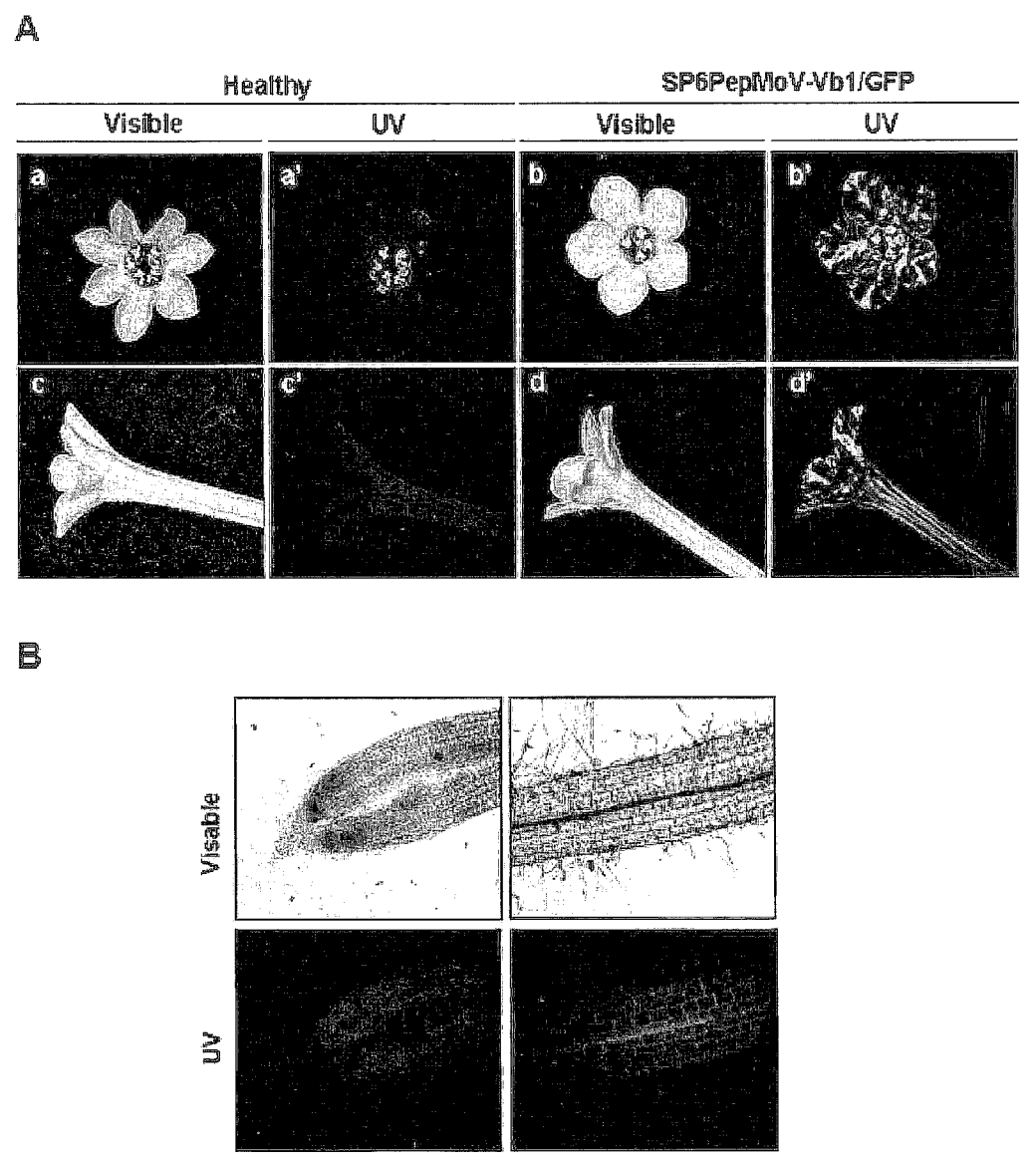

7. Infection of N. benthamiana with pSP6PepMoV-Vb1/GFP and Systemic Expression of the GFP Gene Sac II-treated full-length cDNA clone inserted GFP gene, pSP6PepMoV-Vb1/GFP, was used as template for in vitro transcription as same method applied pSP6PepMoV-Vb1 in the present invention. In vitro generated transcripts of pSP6PepMoV-Vb1/GFP and pSP6PepMoV-Vb1 were inoculated onto N. benthamiana plants (FIG. 18). The inoculated N. benthamiana plants could detect systemically infected to PepMoV-Vb1/GFP through GFP fluorescent at 4 dpi (FIG. 19). While there was no green fluorescence in leaves infected with the pSP6PepMoV-Vb1. Symptoms were the similar as those induced by pSP6PepMoV-Vb1. This result indicated that pSP6PepMoV-Vb1/GFP was also as infectious as pSP6PepMoV-Vb1. The systemically infected leaves displayed severe mosaic symptoms and leaves malformation (FIG. 19). In addition, under UV irradiation, green fluorescence signal could be detected before virus symptom was emerged from infected plants of PepMoV-Vb1/GFP at 3 dpi. Subsequently, fluorescent area enlarged and saturated whole plant along the vein (FIG. 19). The GFP expression could detect faster than virus visual symptom emergence in infected plants by PepMoV-Vb1/GFP. The GFP fluorescence also was observed at root tissue as well as flower of *N. benthamiana* (FIG. 20). To assess the GFP insertion in the symptomatic lesions were showed in inoculated first true leave at 3 dpi. The pSP6PepMoV-Vb1/GFP induced local circular fluorescence sign on inoculation leaves of the systemic host pepper plant at 3 dpi. The fluorescence moved to downward of stem and then these signals spread toward upper leaf veins along the stem and petiole. Gradually, local florescence induced by initial infection of PepMoV-Vb1/GFP developed to upper leaves under the UV light spread to upper leaves systemically. Finally, GFP fluorescence induced by the pSP6PepMoV-Vb1/GFP developed to whole plant systemically. During systemic spreading of GFP signs, local circular fluorescence still could be detected in infection leaves. The pSP6PepMoV-Vb1/GFP also can be employed as a host system for generating viral progeny by initial inoculation for subsequent experiments with other hosts. These circular fluorescent sign has been spread along the leaf veins (Table 5).

TABLE 5

Host ranges and symptomatological analyses of SP6PepMoV-Vb1/GFP

| | Symptom | | | |
|---|---|---|---|---|
| | Inoculated leaves | | Upper leaves | |
| Plant species | Visible symptoms | fluorescence | Visible symptoms | fluorescence |
| *Nicotiana benthamiana* | — | — | sM, Mal, VB | SF |
| *N. tabacum* cv. Xanthi-nc | — | CSF | mM | SF, CSF |
| *N. tabacum* cv. Samsun NN | — | CSF | mM | SF, CSF |
| *N. tabacum* cv. Samsun nn | — | CSF | mM | SF, CSF |
| *Capsicum annuum* L. P915 | — | CSF | sM, Mal | SF |
| *Capsicum annuum* ECW | — | CSF | sM, Mal | SF |
| *Capsicum annuum* Avelar | — | — | — | — |
| *Solanum lycopersicon* | — | — | — | — |
| *Chenopodium amaranticolor* | — | — | — | — |
| *C. pepo* cv. Black Beauty | — | — | — | — |

Figure 21:
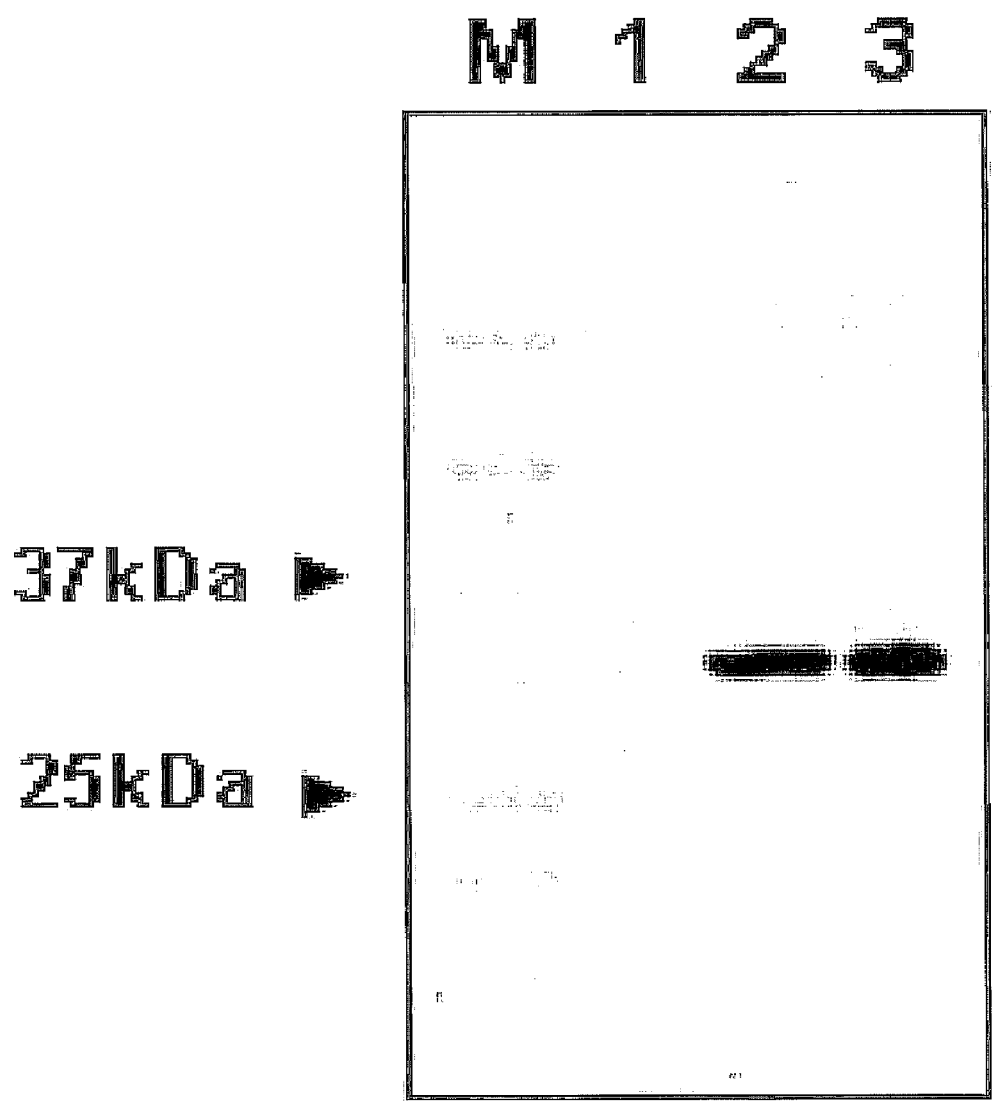
Figure 22:
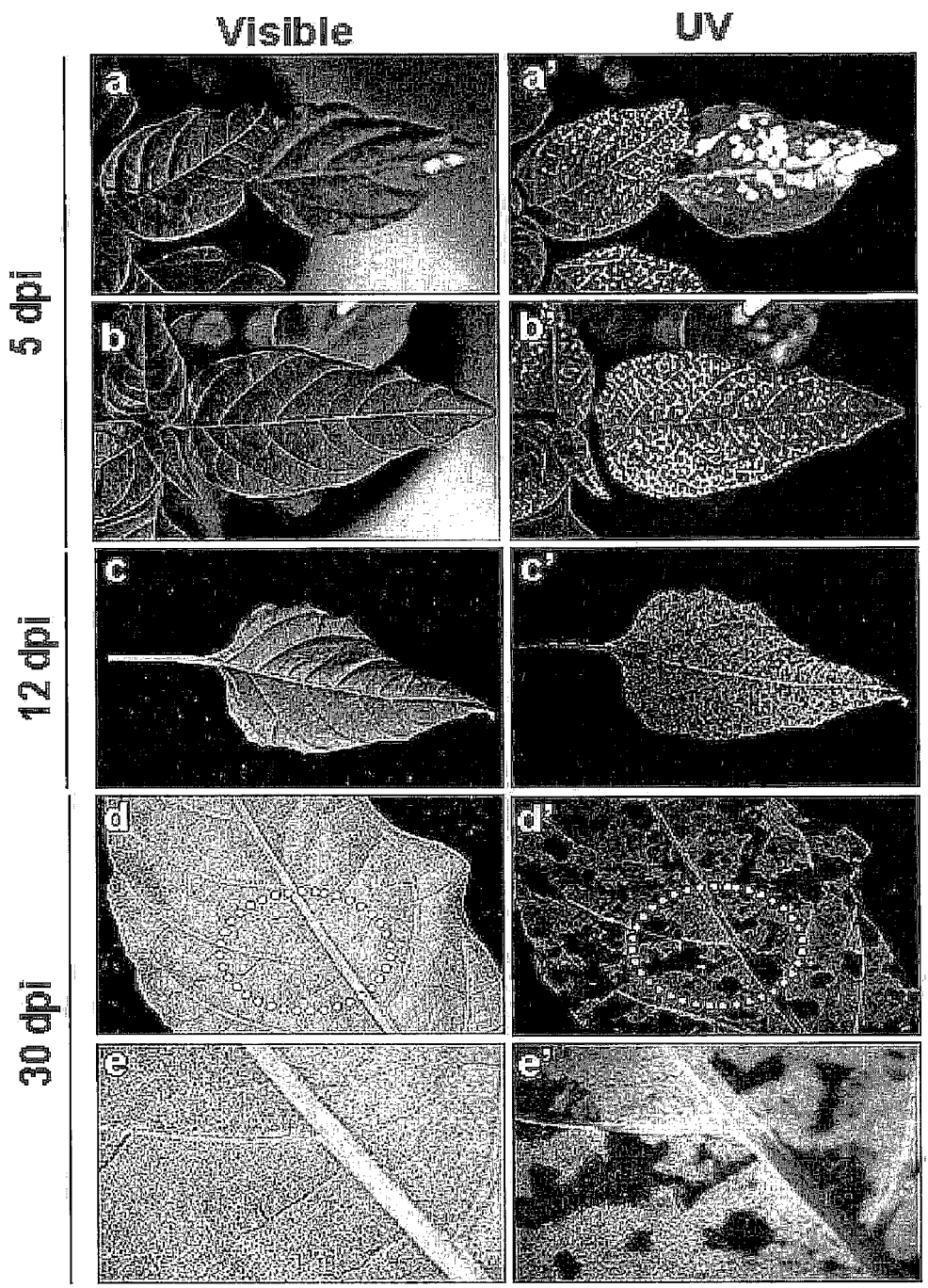
Figure 23:
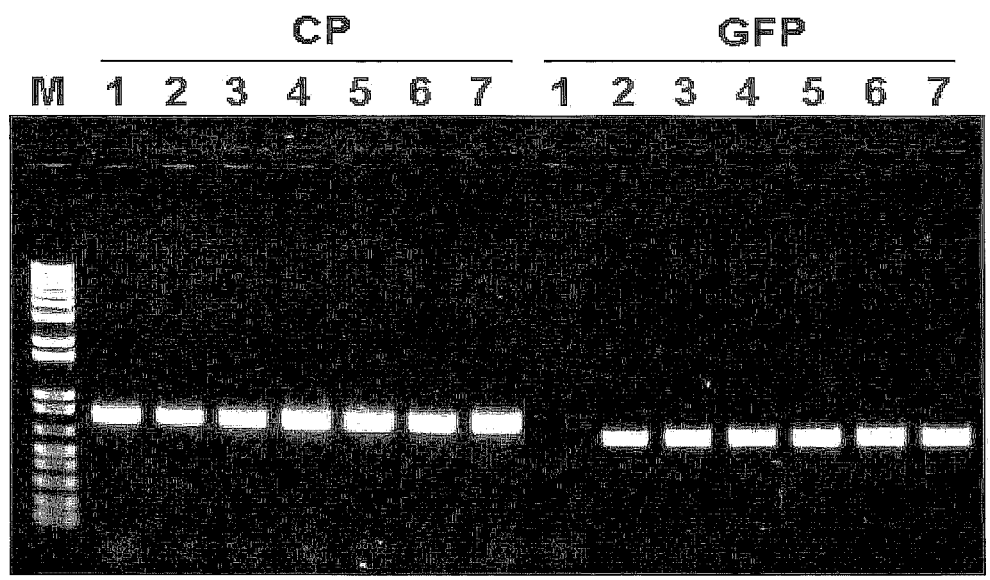
Figure 24:
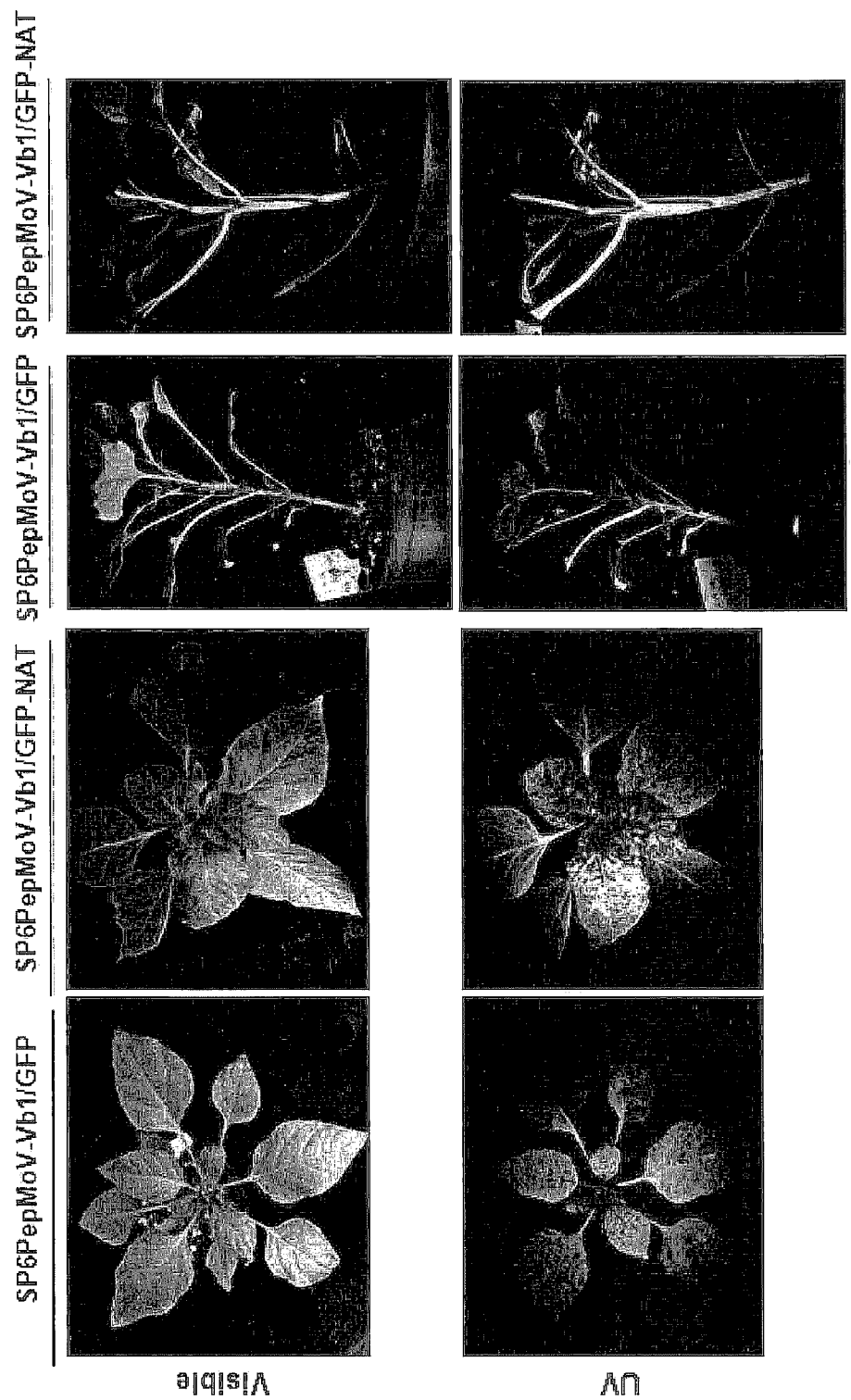

Abbreviation:
mM, mild mosaic;
sM, severe mosaic;
Y, yellow;
Mal, malformation;
VB, vein bending;
CSF, circular systemic fluorescence;
SF, systemic fluorescence;
—, non-infected.

tissues was confirmed by RT-PCR of the RNA from progeny viruses isolated from the systemically infected upper leaves, and subjected to RT-PCR with three different primer sets to detect the PepMoV-CP, GFP and GFP sequence in the recombinant PepMoV-Vb1 RNA. PCR products of the expected size were detected, suggesting stable preservation of GFP sequence in recombinant viral genome (FIG. 4). The leaves of *N. benthamiana* systemically infected with PepMoV-Vb1/GFP were performed western blot analyses using an anti-PepMoV-Vb-CP and anti-turboGFP (avrogen) results showed that GFP have been precisely excised from the viral polyprotein with the viral proteases NIa (FIG. 21)

8. Host Range Study of pSP6PepMoV-Vb1/GFP

To determine the host range of PepMoV-Vb1/GFP, infectivity of pSP6PepMoV-Vb1/GFP was assayed by mechanical inoculation onto several plants including plants of *C. amaranticolor, Solanum lycopersicon, N. tabacum* cv. *Xanthinc, N. tabacum* cv. Samsun NN, *N. tabacum* cv. Samsun nn and *Capsicum annuum*. Plants inoculated with progeny derived from pSP6PepMoV-Vb1/GFP. Pepper plants (*C. annuum* L.) inoculated with PepMoV-Vb1/GFP progeny derived from pSP6PepMoV-Vb1/GFP infected plant. chlorotic fluorescent 9. Analysis of Stability and Passage Experiments of pSP6PepMoV-Vb1/GFP To monitor the genetic stability of vector carrying inserted GFP gene in more detail and to understand the structural fate of GFP in active PepMoV-Vb1 recombinants, RT-PCR analyses were carried out on host plants, after initial infection and also after several successive passages. The stability of pSP6PepMoV-Vb1/GFP was verified with time after initial infection and after every successive trans-inoculation of active viral progeny on new individual hosts. PepMoV-Vb1/GFP progeny were passaged through *N. benthamiana* more than 3 times by mechanical inoculation at 7 days interval until one month. For each passage, the existence and stability of the recombinant virus were monitored using green fluorescence and RT-PCR In the plants of *N. benthamiana*, inoculated with the SP6PepMoV-Vb1/GFP progeny, severe mosaic and leaf malformation symptoms were consistently observed on young leaves. These symptoms were similar with those of the plants showing symptoms with the SP6PepMoV-Vb1. Inserted GFP was stable in SP6PepMoV-Vb1-based vector for at least 30 dpi (FIG. 23). No observed difference in the appearance of symptoms and those were as severe as for the wild-type virus. Furthermore, we did not notice any difference in expression level and stability at either insertion points.

During the test not detected any deletion or escape of foreign gene so far, the pSP6PepMoV/GFP is expected very stable until end of plant life. Thus, the incorporation of GFP in the viral genome did not affect the ability of PepMoV-Vb1 to infect plants. This is the first developed the PepMoV viral vector to look at the expression of GFP.

10. Analysis of Stability and Passage Experiments of pSP6PepMoV-Vb1/GFP

In vitro transcription was performed using Sac II-restricted SP6PepMoV-Vb1/GFP-NAT as a template and the resulting transcripts were inoculated in *N. benthamiana*. To comparatively analyze the expression of the present SP6PepMoV-Vb1/GFP and symptoms, and aphid transition, the transcripts using SP6PepMoV-Vb1/GFP constructs were also inoculated and analyzed in *N. benthamiana* (FIG. 24).

By detecting GFP expression and symptoms in a naked eye, *N. benthamiana* plants inoculated with SP6PepMoV-Vb1/GFP-NAT were same to the symptoms of those inoculated with SP6PepMoV-Vb1/GFP. In addition, GFP expression was highly expressed in leaves and stems and systemically spread by moving to upper leaves. These results suggested that the novel-designed SP6PepMoV-Vb1/GFP-NAT possesses an infectivity to be useful as a virus vector and a capability to express the foreign gene, GFP.

11. Detection Analysis of Aphid infectivity to pSP6PepMoV-Vb1/GFP-NAT Vector

To examine the infectivity transition of SP6PepMoV-Vb1/GFP-NAT by aphids, virus-mediated detection experiments were carried out in *N. benthamiana* infected with SP6PepMoV-Vb1/GFP-NAT using wingless adult insects of *Aphis gossypii* and *Myzus persicae*. The expression of GFP (a reporter protein) mediated by aphid was tested, resulting in no expression of GFP by aphid mediation. It could be appreciated that the present SP6PepMoV-Vb1/GFP-NAT vector exhibits a possibility to exclude aphid-mediated problems and has a high value to be practically applied as a plant virus vector.

The present invention was supported by the grants from Biogreen21 program of Rural Development Administration (project number: 20070301034010), Plant Signal Transduction Network Center of Korea Science and Engineering Foundation (project number: R11-2003-008-02002-0) and Biogreen21 program of Rural Development Administration (project number: 20080401034055008020O).

REFERENCES

Ahlquist, P. et al. 1984. Proc. Nail. Acad. Sci. USA 81: 7066-7070.
An, G. et al. 1988. Plant Mol Biol Manual A3: 1-19.
Anandalakshmi R. et al. 1998. Proc. Natl. Acad. Sci. USA 95: 13079-13084.
Anonymous. 1998. Journal of Plant Pathol. 80: 133-149.
Arazi, T. et al. 2001. J. Biotechnol. 87: 67-82.
Bao, Y. et al. In "Abstract of the XIth International Congress of Virology", 304: 9-13, Sydney, Australia.
Baulcombe, D. C. 1999. Curr. Opin. Plant. Biol. 2: 109-113.
Baulcombe, D. C. 1999. Arch. Virol. Suppl. 15: 189-201.
Baulcombe D. C. 2002. Trends Microbiol. 10: 306-308.
Boccard, F. and Baulcombe, D. C. 1993. Virology 193: 563-578.
Boyer, J. C. and Haenn, A. L. 1994. Virology 198: 415-426.
Brigneti G. et al. 1998. EMBO J. 17: 6739-6746.
Brigneti G. et al. 2004. Plant J. 39: 264-272.
Brunt, A. et al. 1996. Viruses of Plants: Descriptions and Lists from the VIDE Database. C.A.B. International, U.K., 1484 pp.
Canto, T. et al. 1997. Virology 237: 237-248.
Canto, T. and Palukaitis, R, 1998. Virology 250: 325-336.
Canto, T., and Palukaitis, P. 1999. Mol. Plant-Microbe Interact. 12: 985-993.
Caranta C. et al. Theor. Appl. Genet. 94: 431-438.
Carrington, J. C. and Freed, D. D. 1990. J. Virol. 64: 1659-1597.
Carrington, J. C. et al. 1993. J. Virol. 67: 6995-7000.
Chen B. and Francki R. I. B. 1990. J. Gen. Virol. 71: 939-944.
Chen, J. et al. 1996. Virology 226: 198-204.
Chen J. C. et al. 2004. Plant Mol. Biol. 55: 521-530.
Chiang, C. H. and Yeh, S. D. 1997. Bot. Bull. Acad. Sin. 38: 153-163.
Cillo, F. et al. 2002. J. Virol 76: 10654-10664
Choi, I. R. et al. 2000. Plant J. 23: 547-555.
Choi, S. K. et al. 1999. J. Virol. Methods 83: 67-73.
Choi, S. K. et al. 2004. Plant Pathol. J. 20: 212-219.
Choi, S. K. et al. 2003. Virus Res. 97: 1-6.
Chung, E. et al. 2004. Mol. Cells 17: 377-380.
Dagless, E. M. et al. 1997. Arch. Virol. 142: 183-191.
Dawson W. O. and Hilf M. E. 1992. Annu. Rev. Plant. Physiol. Plant Mol. Biol. 43: 527-555.
Deom, C. M. et al. 1997. Protoplasma 19: 1-8.
Ding, S. W. et al. 1994. Virology 198: 593-601.
Ding S. W. et al. 1995. EMBO J. 14: 5762-5772.
Ding, S. W. 2000. Current Opin. Biotechnol. 11: 152-156.
Dolja, V. V. et al. 1991. Virology 184: 79-86.
Dolja, V. V. et al. 1992. Proc. Natl. Acad. Sci. USA 89: 10208-10212.
Domier, L. L. et al. 1989. Proc. Natl. Acad. Sci. USA 86: 3509-3513.
Donson J. et al. 1991. Proc. Natl. Acad. Sci. USA 88: 7204-7208.
Dougherty, W. G. and Carrington, J. C. 1988. Annual Review of Phytopathology 26: 123-143.
Du, Z. Y. et al. 2007. J. Gen. Virol. 88: 2596-2604.
Fakhfakh, H. et al. 1996. J. Gen. Virol. 77: 519-523.
Fire, A. et al. 1998. Nature 391: 806-811.
Fitzmaurice, W. P. et al. 2002. OMICS. 6: 137-151.
Flasinski, S. et al. 1996. Gene 171: 299-300.
Fraser R. S. S. 1990. Annu. Rev. Phytopathol. 28: 179-200.
Fu, D. Q. et al. 2005. The Plant Journal 43: 299-308.
Gallitelli D. 2000. Virus Res. 71: 9-21.
Gal-On, A. et al. 1991. J. Gen. Virol. 72: 2639-2644.
Gal-On, A. et al. 1994. Virology 187: 499-507.
Gal-On, A. et al. 1995. J. Gen. Virol. 76: 3223-3227.
Gera A et al. 1979. Phytopathology 69: 396-399.
German-Retana, S. et al. 2000. Mol. Plant. Microbe Interact. 13: 316-324.
Ghabrial, S. A. et al. 1990 J. Gen. Virol. 71: 1921-1927.
Green, S. K. and Kim, J. S. 1991. AVRDC Tech Bull. No. 18, Shanhua, Taiwan.
Green, S. K. and Kim, J. S. 1991. AVRDC Tech Bull. No. 20, Shanhua, Taiwan.
Habili N. and Symons R. H. 1989. Nucleic Acid Res. 17: 9543-9555.
Hadden J. F. and Black L. L. 1987. Abstracts of the Annual Meeting of The American Phytopathological Society, Southern Division, 1-4 Feb. 1987, Nasheville, USA. Phytopathology 77: 641.
Hadden J. H. and Black L. L. 1989. AVRDC, Taiwan. pp 189-199.
Hamilton A. J. and Baulcombe D. C. 1999. Science 286: 950-952.

Hayes, R. J. and Buck, K. W. 1990. Cell 63: 363-368.
Hong, Y. and Hunt, A. G., 1996. Virology 226: 146-151.
Hsu, C. H. et al. 2004. J. Allergy Clin. Immunol. 13: 1079-1085.
Hull, R. 2002. Mattews 'Plant virology' (4th Ed), Academic press. London.
Ingelbrecht, I. et al. 1994. Proc. Natl. Acad. Sci. USA 22: 10502-10506.
Ishihama A. and Barbier P. 1994. Arch. Virol. 134: 235-258.
Jakab, G. et al. 1997. J. Gen. Viro. 78: 3141-3145.
Johansen, I. E. 1996. Proc. Natl. Acad. Sci. USA 93: 12400-12405.
Johansen L. K. and Carrington J. C. 2001. Plant Physiol. 126: 930-938.
Kamachi, S. et al. 2007. Plant Cell Rep. 26: 1283-1288.
Kaplan, I. B. et al. 1997. Virology 230: 343-349.
Kasschau K. D. et al. 1997. Virology 228: 251-262.
Kasschau K. D. and Carrington J. C. 2001. Virology 285: 71-81.
Kadare, G. et al. 1997. J. Virol. 71: 2583-2590.
Kim, C. H. and Palukaitis, P. 1997. EMBO J. 16: 4060-4068.
Klump, W. M. et al. 1990. J. Virol. 64: 1573-1583.
Kumagai, M. H. et al. 1993. Proc. Natl. Acad. Sci. USA 90: 427-430.
Kumagai, M. H. et al. 1995. Proc. Natl. Acad. Sci. USA 92: 1679-1683.
Kumagai, M. H. et al. 1998. Plant 3.14: 305-315.
Lainn, S. et al. 1990. Nucl. Acids Res. 18: 7003-7006.
Lama, J., and Carrasco, L. 1992. J. Biol. Chem. 267: 15932-15937.
Langenberg, W. G. and Zhang, L., 1997. J. Struct. Biol. 118: 243-247.
Lapidot M. et al. 1997. Plant Dis. 81: 185-188.
Lin, H. X. et al. 2004. J. Virol. 78: 6666-6675.
Lin, S. S. et al. 2001. Bot. Bull. Acad. Sin. 42: 243-250.
Lin, S. S. et al. 2002. Bot. Bull. Acad. Sin. 43: 261-269.
Lindbo, J. A. et al. 2003. Plant Cell 5: 1749-1759.
Liu, Y. et al. 2002a. Plant J. 31: 777-786.
Liu, Y. et al. 2002b. Plant J. 30: 415-429.
Llave C. et al. 2002. Proc. Natl. Acad. Sci. USA 97: 13401-13406.
López-Moya J. J., and Garcia J. A. 2000. Virus Res. 68: 99-107.
Lot, H. and Kaper, J. M. 1976. Virology 74: 223-226.
Maia, I. G. et al. 1996. J. Gen. Virol. 77: 1335-1341.
Maiss, E. et al. 1989. J. Gen. Virol. 70: 513-524.
Maiss, E. et al. 1992. J. Gen. Virol. 73: 709-713.
Marsh, L. E. et al. Virology 172: 415-427.
Martin, M. T. and Gelie, B. 1997. European Journal of Plant Pathology 103: 427-431.
McCormick, A. A. et al. 1999. Proc. Natl. Acad. Sci. USA 96: 703-708.
McGarvey, P. et al. 1995. J. Gen. Virol. 76: 2257-2270.
Mette M. F. et al. 2000. EMBO J. 19: 5194-5201.
Mlotshwa, S. et al. 2002. Virus Genes 15: 45-57.
Monma, S, and Sakata, Y. 1997. J. Jpn. Soc. Hortic. Sci. 65: 769-776.
Napoli, C. et al. 1990. Plant Cell 2: 279-289.
Nelson, M. R. and Wheeler, R. E. 1978. Phytopathology 68: 979-984.
Nelson, M. R. et al. 1982. CMI/AAB Descriptions of Plant Viruses No. 253.
Nelson, R. S. and Van Bel, A. J. E. 1998. Prog. Bot. 59: 476-533.
Nicola-Negri, E. D. et al. 2005. Transgenic Research 14: 989-994.
Nicolas, O. et al. 1996. Arch. Virol. 141: 1535-1552.
Nono-Womdim R. et al. 1993a. Ann. Appl. Biol. 122: 49-56.
Nono-Womdim R. et al. 1993b. J. Phytopathol. 137: 125-132.
Olsen. B. S. and Johansen, I. E. 2001. Arch. Virol. 146: 15-25.
O'Reilly, E. K. and Kao, C. C. 1998. Virology 252: 287-303.
Palukaitis, P. et al. 1992. Adv. Virus Res. 41: 281-348.
Palukaitis, P. and Garcia-Arenal, F. 2003. Adv. Virus Res. 62: 241-323.
Pandolfini, T. et al. 2003. BMC Biotechnology 3: 7.
Peart, J. R. et al. 2002. Plant J. 29: 569-579.
Peden, K. W. C. and Symons, R. H. 1979. Virology 53: 487-492.
Peng, Y.-h. et al. 1998. J. Gen. Virol. 79: 897-904.
Plisson, C. et al. 2003. J Biol. Chem. 278: 23753-23761.
Purcifull D. E. et al. 1973. Virology 55: 275-279.
Purcifull D. E. et al. 1975. Phytopathology 65: 559-562.
Puurand, U. et al. 1996. Virus Res. 40: 135-140.
Rajamaki, M. L. and Valkonen, J. P., 1999. Mol. Plant. Microbe Interact. 12: 1074-1081.
Ratcliff, F. G. et al. 1999. Plant Cell 11: 1207-1216.
Ratcliff, F. G. et al. 2001. Plant J. 25: 237-245.
Riechmann, J. L. et al. 1990. Virology 177: 710-716.
Riechmann, J. L. et al. 1992. Journal of General Virology 73: 1-16.
Riechmann, J. L. et al. 1995. J. Gen. Virol. 76: 951-956.
Ritzenthaler, C. 2005. Curr Opin Biotechnol. 16: 118-122.
Rizzo, T. M. and Palukaitis, P. 1990. Mol. Gen. Genet. 222: 249-256.
Rizos, H. et al. 1992. J. Gen. Virol. 73: 2099-2103.
Robaglia, C. et al. 1989. J. Gen. Virol, 70: 935-947.
Roossinck, M. J. et al. 1999. J. Virol. 73: 6752-6758.
Roossinck M. J. 2002. J. Virol. 76: 3382-3387.
Ruiz, T. et al. 1998. Plant Cell 10: 937-946.
Ryu, K. H. et al. 1998. Mol. Plant-Microbe Interact. 11: 351-357.
Salanki, K. et al. 1994. Virus Res. 33: 281-289.
Sambrook, J. et al. 1989. Molecular Cloning: A Laboratory Manual, 2nd ed. Cold Spring Harbor Laboratory Press, New York.
Sanchez, F. et al. 1998. Virus Res. 55: 207-219.
Sanger, F. et al. 1977. Proc. Natl. Acad. Sci. USA 74: 5463-5467.
Schaad, M. C. et al. 1997. EMBO J. 16: 4049-4059.
Schweizer H. P., 2008, Genomic Methods, 25: S633-S641.
Shahabuddin, M. et al. 1988. Virology 163: 635-637.
Shi, B. J. et al. 2002. Mol. Plant. Microbe Interact 15: 947-955.
Shi, B. J. et al. 2003. Mol. Plant. Microbe Interact 16: 261-267.
Shin, R. et al. 2002a. Transgenic Res.11: 215-219.
Shin, R. et al. 2002b. Mol. Plant. Microbe Interact. 15: 983-989.
Shukla, D. D. and Ward, C. W. 1989. Adv Virus Res. 36: 273-314.
Shukla, D. D. et al. 1991. Canadian J. Plant Pathol. 13: 178-191.
Smith N. A. et al. 2000. Nature 407: 319-20.
Soards, A. J. et al. 2002. Mol. Plant. Microbe Interact 15: 647-653.
Takahashi, Y. et al. 1997. Virus Genes 14: 235-243.
Tacahashi, Y. and Uyeda I. 1999. Virology 265: 147-152.
Takeshita, M. et al. 1998. Arch. Virol. 143: 1109-1117.
Tenllado, F. and Diaz-ruiz J. R. 2001. J. Virol. 75: 12288-12297.
Tenllado, F. et al. 2003. BMC Biotechnology 3: 3.
Tenllado F. et al. 2004. Virus Res. 102: 85-96.
Thornbury, D. W. et al. 1985. Virology 144: 260-267.
Tobin, G. J. et al. 1989. Cell 59: 511-519.

Turpen, T. H. 1999. Philos Trans R Soc Lond Biol 0.354: 665-673.
Uhlin, B. E. et al. 1979. Gene 6: 91-106.
Urcuqui-Inchima et al. 1999. J. Gen. Virol. 80: 2809-2812.
Van der Krol, A. R. et al. 1990. Plant Cell 2: 291-299.
Van der Krol, A. R. et al. 1990. Plant Mol. Biol. 14: 457-466.
Vance, V. and Vaucheret, H. 2001. Science 292: 2277-2280.
Vance V. B et al. 1992. Arch. Virol. [Suppl 5]: 337-345.
Vazquez Rovere C. et al. 2002. Curr. Opin. Biotechnol. 13: 167-172.
Verchot, J. and Carrington, J. C. 1995. Journal of Virology 69: 1582-1590.
Villalon, B. 1981. Plant Dis. 65: 557-562.
Voinnet O. et al. 2000. Cell 103: 157-167.
Wang, Y. et al. 2000. Virus Genes. 20: 11-17.
Ward C. W., and Shukla D. D. 1991. Intervirology 32: 269-296.
Yang, S. J. et al. 1998. Arch. Virol. 143: 2443-2451.
Zaitlin, M. and Hull, R. 1987. Annu. Rev. Plant Physiol. 38: 291-315.
Zhao, M. M. et al. 2006. Acta Biochimica et Biophysica Sinica 38: 22-28.
Zitter T. A. 1972. Plant Dis Rep. 56: 586-590.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A pepper mottle virus-derived plant infectious nucleic acid molecule comprising the nucleotide sequence of SEQ ID NO:1, except that the nucleic acid molecule has a substituted nucleotide at nucleotide 8584 of SEQ ID NO:1 to remove aphid-mediated infectivity, in which the substituted nucleotide at nucleotide 8584 is a nucleotide A base.

2. A recombinant vector, comprising (i) the nucleotide sequence according to claim 1, and (ii) a promoter operatively linked to the nucleotide sequence, wherein the recombinant vector further comprises a sequence encoding a green fluorescent protein (GFP).

3. The recombinant vector according to claim 2, wherein the promoter comprises an SP6 promoter, T7 promoter, T3 promoter, PM promoter, maize-ubiquitin promoter, Cauliflower mosaic virus (CaMV)-35S promoter, Nopalin synthase (nos) promoter, Figwort mosaic virus 35S promoter, Sugarcane bacilliform virus promoter, commelina yellow mottle virus promoter, photo-inducible promoter of small subunit of Ribulose-1,5-bis-phosphate carboxylase (ss-RUBISCO), cytosolic triosphosphate isomerase (TPI) promoter in rice, adenine phosphoribosyltransferase (APRT) or octopine synthase promoter in *Arabidopsis*.

4. The recombinant vector according to claim 3, wherein the promoter is an SP6 promoter.

5. A cell transformed or infected with the plant infectious nucleic acid molecule according to claim 1 or its transcript.

6. A plant transformed or infected with the plant infectious nucleic acid molecule according to claim 1 or its transcript.

* * * * *